United States Patent
Coe et al.

(10) Patent No.: US 7,465,743 B2
(45) Date of Patent: Dec. 16, 2008

(54) PYRAZOLO[3,4-B]PYRIDINE COMPOUNDS, AND THEIR USE AS PDE4 INHIBITORS

(75) Inventors: Diane Mary Coe, Stevenage (GB); Caroline Mary Cook, Stevenage (GB); Anthony William James Cooper, Stevenage (GB); Christopher David Edlin, Stevenage (GB); Julie Nicole Hamblin, Stevenage (GB); Martin Redpath Johnson, Stevenage (GB); Paul Spencer Jones, Stevenage (GB); Mika Kristian Lindvall, Emeryville, CA (US); Charlotte Jane Mitchell, Stevenage (GB); Alison Judith Redgrave, Stevenage (GB); John Edward Robinson, Stevenage (GB)

(73) Assignee: Glaxo Group Limited, Middlesex (GB)

( * ) Notice: Subject to any disclaimer, the term of this patent is extended or adjusted under 35 U.S.C. 154(b) by 223 days.

(21) Appl. No.: 10/598,944

(22) PCT Filed: Mar. 15, 2005

(86) PCT No.: PCT/GB2005/000976

§ 371 (c)(1),
(2), (4) Date: Sep. 15, 2006

(87) PCT Pub. No.: WO2005/090353

PCT Pub. Date: Sep. 29, 2005

(65) Prior Publication Data

US 2007/0167485 A1 Jul. 19, 2007

(30) Foreign Application Priority Data

Mar. 16, 2004 (GB) .................................. 0405937.4

(51) Int. Cl.
A01N 43/42 (2006.01)
A61K 31/44 (2006.01)
C07D 471/02 (2006.01)
C07D 491/02 (2006.01)
C07D 498/02 (2006.01)
C07D 513/02 (2006.01)
C07D 515/02 (2006.01)

(52) U.S. Cl. ...................... 514/303; 546/120
(58) Field of Classification Search ................. 546/120; 514/303
See application file for complete search history.

(56) References Cited

U.S. PATENT DOCUMENTS 3,840,546 A 10/1974 Hoehn et al.
3,925,388 A 12/1975 Hoehn et al.
4,072,681 A * 2/1978 Denzel et al. ............... 544/251

OTHER PUBLICATIONS

Hohn H et al: "Potential Antidiabetic Agents. Pyrazolo '3,4-b!pyridines" Journal of Medicinal Chemistry, American_Chemical Society. Washington, US, vol. 16, No. 12, 1973, pp. 1340-1346, XP002097814, ISSN: 0022-2623, p. 1343; compound 37.
Patent Abstracts of Japan, vol. 2002, No. 05, May 3, 2002-& JP 2002 020386 A (ON0 Pharmaceut Co Ltd), Jan. 23, 2002 cited in the application abstract.

* cited by examiner

Primary Examiner—D. Margaret Seaman
Assistant Examiner—Niloofar Rahmani
(74) Attorney, Agent, or Firm—James M. Kanagy; Stephen Venetianer; Charles M. Kinzig

(57) ABSTRACT

The invention relates to a compound of formula (I) or a salt thereof:

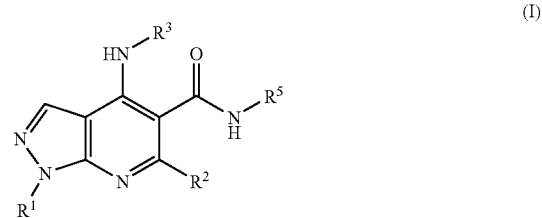

(I)

wherein: $R^1$ is Et, n-Pr, i-Pr, $C_2$fluoroalkyl, or —$CH_2CH_2OH$; $R^2$ is H, Me, Et, n-Pr, i-Pr, $C_{1-2}$fluoroalkyl, cyclopropyl or (cyclopropyl)methyl-; and $NHR^3$ has the sub-formula (nhr3):

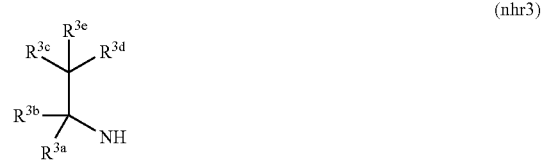

(nhr3)

wherein $R^{3a}$ is methyl or ethyl; $R^{3b}$ is H, methyl or ethyl; $R^{3c}$ is H, methyl or ethyl, $R^{3d}$ is H, methyl or ethyl, and $R^{3e}$ is H or methyl,
provided that: (a) $R^{3b}$ is methyl or ethyl; and/or (b) $R^{3c}$ and $R^{3d}$ are independently methyl or ethyl; and provided that: (c) when $R^{3c}$ is ethyl and/or when $R^{3d}$ is ethyl and/or when $R^{3e}$ is methyl, then: $R^{3a}$ is methyl and/or $R^{3b}$ is hydrogen or methyl.

These compounds are PDE4 inhibitors.

24 Claims, No Drawings

PYRAZOLO[3,4-B]PYRIDINE COMPOUNDS, AND THEIR USE AS PDE4 INHIBITORS

This application claims the benefit of International Application No. PCT/GB2005/000976, filed 15 Mar. 2005, which claims the priority of GB0405937.4 filed 16 Mar. 2004.

The present invention relates to pyrazolo[3,4-b]pyridine compounds, processes for their preparation, intermediates usable in these processes, and pharmaceutical compositions containing the compounds. The invention also relates to the use of the pyrazolo[3,4-b]pyridine compounds in therapy, for example as inhibitors of phosphodiesterase type IV (PDE4) and/or for the treatment and/or prophylaxis of inflammatory and/or allergic diseases such as chronic obstructive pulmonary disease (COPD), asthma, rheumatoid arthritis or allergic rhinitis.

BACKGROUND TO THE INVENTION

U.S. Pat. Nos. 3,979,399, 3,840,546, and 3,966,746 (E.R. Squibb & Sons) disclose 4-amino pyrazolo[3,4-b]pyridine-5-carboxamide compounds of the following formula and salts thereof:

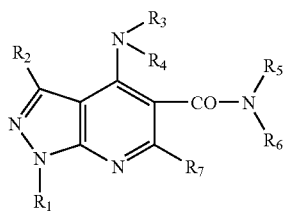

In U.S. Pat. No. 3,979,399, the 4-amino group $NR_3R_4$ can be an acyclic amino group wherein $R_3$ and $R_4$ may each be hydrogen, lower alkyl, lower alkenyl, lower alkanoyl, phenyl, substituted phenyl, phenyl-lower alkyl, di-lower alkyl amino-lower alkyl, benzoyl, substituted benzoyl, phenyl-lower alkanoyl, substituted phenyl-lower alkanoyl, lower alkanesulfonyl, benzenesulfonyl, or substituted benzenesulfonyl. $NR_3R_4$ can alternatively be a 3, 4, 5 or 6 membered heterocyclic group optionally including an additional heteroatom such as N, O or S. In preferred embodiments, $R_3$ is lower alkyl, most preferably butyl and/or $R_4$ is hydrogen; or $R_3$ and $R_4$ together with the nitrogen to which they are attached form a 5 or 6 membered heterocyclic such as pyrrolidino, piperidino or piperazino. In the 5-carboxamide group $C(O)NR_5R_6$, $NR_5R_6$ can be an acyclic amino group wherein $R_5$ and $R_6$ may each be hydrogen, lower alkyl, alkoxy lower alkyl, dialkoxy lower alkyl, or di-loweralkylamino-lower alkyl; or $NR_5R_6$ can be heterocyclic containing 5, 6 or 7 members in which an additional heteroatom such as N, O or S may optionally be included. In U.S. Pat. No. 3,979,399, the 1-substituent (on the pyrazolo-1-nitrogen) $R_1$ is hydrogen, lower alkyl, phenyl, phenyl-lower alkyl, or cycloalkyl; preferably hydrogen or lower alkyl; most preferably hydrogen or ethyl. The 3-substituent $R_2$ is hydrogen, lower alkyl or phenyl; preferably hydrogen or lower alkyl; most preferably hydrogen or methyl. The 6-substituent $R_7$ is H, lower alkyl or phenyl, most preferably H or methyl. In U.S. Pat. No. 3,979,399, lower alkyl and lower alkenyl are defined as including straight or branched chain hydrocarbon groups containing 1 to 8 carbon atoms; examples of the type of group contemplated in U.S. Pat. No. 3,979,399 being methyl, ethyl, propyl, isopropyl, butyl, t-butyl, etc. and corresponding compounds having one double bond.

In U.S. Pat. No. 3,979,399, Example 1 is 4-butylamino-1-ethyl-pyrazolo[3,4-b]pyridine-5-(N-butyl)carboxamide hydrochloride, and Example 19 is the compound wherein $R_1$ is $(CH_3)_2CH—$, $R_2$ is H, $R_3$ is $—CH(CH_3)C_2H_5$, $R_4$ is H, $R_5$ is Ph, and $R_6$ and $R_7$ are H.

The compounds of U.S. Pat. No. 3,979,399 are disclosed therein as being central nervous system depressants useful as ataractic, analgesic and hypotensive agents, e.g. for oral or parenteral administration.

U.S. Pat. Nos. 3,925,388, 3,856,799, 3,833,594 and 3,755,340 (E.R. Squibb & Sons) disclose 4-amino derivatives of pyrazolo[3,4-b]pyridine-5-carboxylic acids and esters. The 4-amino group $NR_3R_4$ can be an acyclic amino group wherein $R_3$ and $R_4$ may each be hydrogen, lower alkyl (e.g. butyl), phenyl, etc.; $NR_3R_4$ can alternatively be a 5-6-membered heterocyclic group in which an additional nitrogen is present such as pyrrolidino, piperidino, pyrazolyl, pyrimidinyl, pyridazinyl or piperazinyl. The compounds are mentioned as being central nervous system depressants useful as ataractic agents or tranquilizers, as having antiinflammatory and analgesic properties. The compounds are mentioned as increasing the intracellular concentration of adenosine-3',5'-cyclic monophosphate and for alleviating the symptoms of asthma.

H. Hoehn et al., *J. Heterocycl. Chem.*, 1972, 9(2), 235-253 discloses a series of 1H-pyrazolo[3,4-b]pyridine-5-carboxylic acid derivatives with 4-hydroxy, 4-chloro, 4-alkoxy, 4-hydrazino, and 4-amino substituents.

CA 1003419, CH 553 799 and T. Denzel, *Archiv der Pharmazie*, 1974, 307(3), 177-186 disclose 4,5-disubstituted 1H-pyrazolo[3,4-b]pyridines unsubstituted at the 1-position.

Japanese laid-open patent application JP-2002-20386-A (Ono Yakuhin Kogyo K K) published on 23 Jan. 2002 discloses pyrazolopyridine compounds of the following formula:

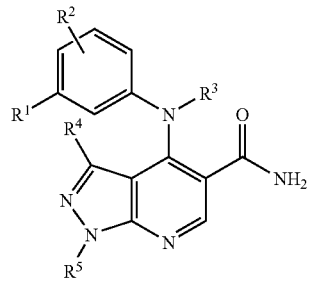

JP-2002-20386-A
(Ono)

wherein $R^1$ denotes 1) a group $—OR^6$, 2) a group $—SR^7$, 3) a C2-8 alkynyl group, 4) a nitro group, 5) a cyano group, 6) a C1-8 alkyl group substituted by a hydroxy group or a C1-8 alkoxy group, 7) a phenyl group, 8) a group $—C(O)R^8$, 9) a group $—SO_2NR^9R^{10}$, 10) a group $—NR^{11}SO_2R^{12}$, 11) a group $—NR^{13}C(O)R^{14}$ or 12) a group $—CH=NR^{15}$. $R^6$ and $R^7$ denote i) a hydrogen atom, ii) a C1-8 alkyl group, iii) a C1-8 alkyl group substituted by a C1-8 alkoxy group, iv) a trihalomethyl group, v) a C3-7 cycloalkyl group, vi) a C1-8 alkyl group substituted by a phenyl group or vii) a 3-15 membered mono-, di- or tricyclic hetero ring containing 1-4 nitrogen atoms, 1-3 oxygen atoms and/or 1-3 sulphur atoms. $R^2$ denotes 1) a hydrogen atom or 2) a C1-8 alkoxy group. $R^3$ denotes 1) a hydrogen atom or 2) a C1-8 alkyl group. $R^4$ denotes 1) a hydrogen atom, 2) a C1-8 alkyl group, 3) a C3-7 cycloalkyl group, 4) a C1-8 alkyl group substituted by a C3-7 cycloalkyl group, 5) a phenyl group which may be substituted by 1-3 halogen atoms or 6) a 3-15 membered mono-, di- or tricyclic hetero ring containing 1-4 nitrogen atoms, 1-3 oxygen atoms and/or 1-3 sulphur atoms. $R^5$ denotes 1) a hydrogen atom, 2) a C1-8 alkyl group, 3) a C3-7 cycloalkyl group, 4) a C1-8 alkyl group substituted by a C3-7 cycloalkyl group or 5) a phenyl group which may be substituted by 1-3 substituents. In group $R^3$, a hydrogen atom is preferred. In group $R^4$, methyl, ethyl, cyclopropyl, cyclobutyl or cyclopentyl are preferred. The compounds of JP-2002-20386-A are stated as having PDE4 inhibitory activity and as being useful in the prevention and/or treatment of inflammatory diseases and many other diseases.

1,3-Dimethyl-4-(arylamino)-pyrazolo[3,4-b]pyridines with a 5-C(O)NH$_2$ substituent similar or identical to those in JP-2002-20386-A were disclosed as orally active PDE4 inhibitors by authors from Ono Pharmaceutical Co. in: H. Ochiai et al., *Bioorg. Med. Chem. Lett.*, 5 Jan. 2004 issue, vol. 14(1), pp. 29-32 (available on or before 4 Dec. 2003 from the Web version of the journal: "articles in press").

EP 0 076 035 A1 (ICI Americas) discloses pyrazolo[3,4-b]pyridine derivatives as central nervous system depressants useful as tranquilizers or ataractic agents for the relief of anxiety and tension states.

The compound cartazolate, ethyl 4-(n-butylamino)-1-ethyl-1H-pyrazolo[3,4-b]-pyridine-5-carboxylate, is known. J. W. Daly et al., *Med. Chem. Res.*, 1994, 4, 293-306 and D. Shi et al., *Drug Development Research*, 1997, 42, 41-56 disclose a series of 4-(amino)substituted 1H-pyrazolo[3,4-b]pyridine-5-carboxylic acid derivatives, including ethyl 4-cyclopentylamino-1-methyl-1H-pyrazolo[3,4-b]pyridine-5-carboxylate, and their affinities and antagonist activities at $A_1$- and $A_{2A}$-adenosine receptors, and the latter paper discloses their affinities at various binding sites of the GABA$_A$-receptor channel. S. Schenone et al., *Bioorg. Med. Chem. Lett.*, 2001, 11, 2529-2531, and F. Bondavalli et al., *J. Med. Chem.*, 2002, vol. 45 (Issue 22, 24 Oct. 2002, allegedly published on Web Sep. 24, 2002), pp. 4875-4887 disclose a series of 4-amino-1-(2-chloro-2-phenylethyl)-1H-pyrazolo[3,4-b] pyridine-5-carboxylic acid ethyl esters as $A_1$-adenosine receptor ligands.

WO 02/060900 A2 appears to disclose, as MCP-1 antagonists for treatment of allergic, inflammatory or autoimmune disorders or diseases, a series of bicyclic heterocyclic compounds with a —C(O)—NR$^4$—C(O)—NR$^5$R$^6$ substituent, including isoxazolo[5,4-b]pyridines and 1H-pyrazolo[3,4-b] pyridines (named as pyrazolo[5,4-b]pyridines) with the —C(O)—NR$^4$—C(O)—NR$^5$R$^6$ group as the 5-substituent and optionally substituted at the 1-, 3-, 4-, and/or 6-positions. Bicyclic heterocyclic compounds with a —C(O)NH$_2$ substituent instead of the —C(O)—NR$^4$—C(O)—NR$^5$R$^6$ substituent are alleged to be disclosed in WO 02/060900 as intermediates in the synthesis of the —C(O)—NR$^4$—C(O)—NR$^5$R$^6$ substituted compounds.

WO 00/15222 (Bristol-Myers Squibb) discloses inter alia pyrazolo[3,4-b]pyridines having either a C(O)—X$_1$ group at the 5-position and a group E$_1$ at the 4-position of the ring system or C(O)—X$_2$ group at the 5-position and a group E$_2$ at the 4-position of the ring system. X$_1$ and X$_2$ are —OR or —NRR. E$_1$ is —NH-A$_1$-cycloalkyl, —NH-A$_1$-substituted cycloalkyl, —NH-A$_1$-heterocyclo, —NH-A$_1$-heteroaryl, et al. E$_2$ is —NH-A$_1$-alkoxy, —NH-A$_1$-CO$_2$alkyl, —NH-A$_1$-N(R$^{15}$)(R$^{16}$), —NH-A$_1$-aryl or —NH-A$_1$-substituted aryl. A$_1$ is an alkylene or substituted alkylene bridge of 1 to 10 carbons. The compounds are disclosed as being useful as inhibitors of cGMP phosphodiesterase, especially PDE type V, and in the treatment of various cGMP-associated conditions such as erectile dysfunction. 4-alkylamino-pyrazolo[3,4-b]pyridines and/or PDE4 inhibitory activity do not appear to be disclosed in WO 00/15222.

Copending patent application PCT/EP03/11814, filed on 12 Sep. 2003 in the name of Glaxo Group Limited and incorporated herein by reference, discloses pyrazolo[3,4-b]pyridine compounds or salts thereof with a 4-NHR$^3$ group and a 5-C(O)—X group, according to this formula (I):

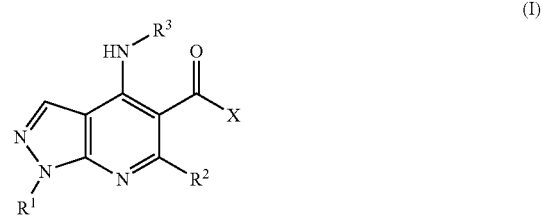

(I)

wherein:
R$^1$ is C$_{1-4}$alkyl, C$_{1-3}$fluoroalkyl, —CH$_2$CH$_2$OH or —CH$_2$CH$_2$CO$_2$C$_{1-2}$alkyl;
R$^2$ is a hydrogen atom (H), methyl or C$_1$ fluoroalkyl;
R$^3$ is optionally substituted C$_{3-8}$cycloalkyl or optionally substituted mono-unsaturated-C$_{5-7}$cycloalkenyl or an optionally substituted heterocyclic group of sub-formula (aa), (bb) or (cc);

(aa)

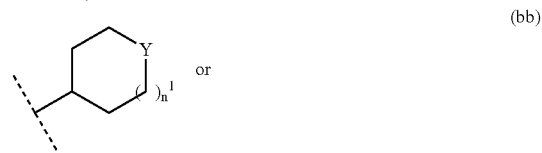

(bb)

(cc)

in which n$^1$ and n$^2$ independently are 1 or 2; and in which Y is O, S, SO$_2$, or NR$^{10}$;
or R$^3$ is a bicyclic group (dd) or (ee):

(dd)

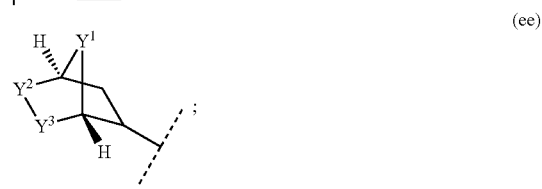

(ee)

and wherein X is $NR^4R^5$ or $OR^{5a}$.

In PCT/EP03/11814, $R^4$ is a hydrogen atom (H); $C_{1-6}$alkyl; $C_{1-3}$fluoroalkyl; or $C_{2-6}$alkyl substituted by one substituent $R^{11}$.

In PCT/EP03/11814, $R^5$ can be: a hydrogen atom (H); $C_{1-8}$alkyl; $C_{1-8}$ fluoroalkyl; $C_{3-8}$cycloalkyl optionally substituted by a $C_{1-2}$alkyl group; —$(CH_2)_n{}^4$—$C_{3-8}$cycloalkyl optionally substituted, in the —$(CH_2)_n{}^4$— moiety or in the $C_{3-8}$cycloalkyl moiety, by a $C_{1-2}$alkyl group, wherein $n^4$ is 1, 2 or 3; $C_{2-6}$alkyl substituted by one or two independent substituents $R^{11}$; —$(CH_2)_n{}^{11}$—$C(O)R^{16}$; —$(CH_2)_n{}^{12}$—$C(O)NR^{12}R^{13}$; —$CHR^{19}$—$C(O)NR^{12}R^{13}$; —$(CH_2)_n{}^{12}$—$C(O)OR^{16}$; —$(CH_2)_n{}^{12}$—$C(O)OH$; —$CHR^{19}$—$C(O)OR^{16}$; —$CHR^{19}$—$C(O)OH$; —$(CH_2)_n{}^{12}$—$SO_2$—$NR^{12}R^{13}$; —$(CH_2)_n{}^{12}$—$SO_2R^{16}$; or —$(CH_2)_n{}^{12}$—$CN$; —$(CH_2)_n{}^{13}$-Het; or optionally substituted phenyl. Alternatively, in PCT/EP03/11814, $R^5$ can have the sub-formula (x), (y), (y1) or (z):

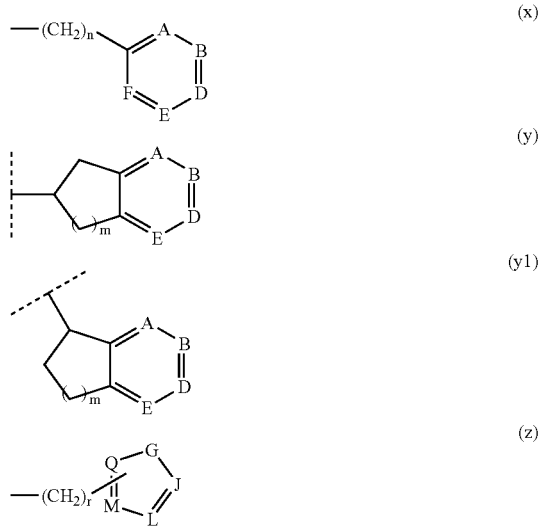

wherein in sub-formula (x), n=0, 1 or 2; in sub-formula (y) and (y1), m=1 or 2; and in sub-formula (z), r=0, 1 or 2; and wherein in sub-formula (x) and (y) and (y1), none, one or two of A, B, D, E and F are independently nitrogen or nitrogen-oxide ($N^+$—$O^-$) provided that no more than one of A, B, D, E and F is nitrogen-oxide, and the remaining of A, B, D, E and F are independently CH or $CR^6$; and provided that when n is 0 in sub-formula (x) then one or two of A, B, D, E and F are independently nitrogen or nitrogen-oxide ($N^+$—$O^-$) and no more than one of A, B, D, E and F is nitrogen-oxide;

In PCT/EP03/11814, each $R^6$, independently of any other $R^6$ present, is: a halogen atom; $C_{1-6}$alkyl; $C_{1-4}$fluoroalkyl; $C_{1-4}$alkoxy; $C_{1-2}$fluoroalkoxy; $C_{3-6}$cycloalkyloxy; —$C(O)R^{16a}$; —$C(O)OR^{30}$; —$S(O)_2$—$R^{16a}$; $R^{16a}$—$S(O)_2$—$NR^{15a}$—; $R^7R^8N$—$S(O)_2$—; $C_{1-2}$alkyl-$C(O)$—$R^{15a}N$—$S(O)_2$—; $C_{1-4}$alkyl-$S(O)$—; Ph-$S(O)$—; $R^7R^8N$—$CO$—; —$NR^{15}$—$C(O)R^{16}$; $R^7R^8N$; OH; $C_{1-4}$alkoxymethyl; $C_{1-4}$alkoxyethyl; $C_{1-2}$alkyl-$S(O)_2$—$CH_2$—; $R^7R^8N$—$S(O)_2$—$CH_2$—; $C_{1-2}$alkyl-$S(O)_2$—$NR^{15a}$—$CH_2$—; —$CH_2$—OH; —$CH_2CH_2$—OH; —$CH_2$—$NR^7R^8$; —$CH_2$—$CH_2$—$NR^7R^8$; —$CH_2$—$C(O)OR^{30}$; —$CH_2$—$C(O)$—$NR^7R^8$; —$CH_2$—$NR^{15a}$—$C(O)$—$C_{1-3}$alkyl; —$(CH^2)_n{}^{14}$-$Het^1$ where $n^{14}$ is 0 or 1; cyano (CN); $Ar^{5b}$; or phenyl, pyridinyl or pyrimidinyl wherein the phenyl, pyridinyl or pyrimidinyl independently are optionally substituted by one or two of fluoro, chloro, $C_{1-2}$alkyl, $C_1$ fluoroalkyl, $C_{1-2}$alkoxy or $C_1$ fluoroalkoxy;

or two adjacent $R^6$ taken together can be —O—$(CMe_2)$—O— or —O—$(CH_2)_n{}^{14}$—O— where $n^{14}$ is 1 or 2.

In PCT/EP03/11814, in sub-formula (z), G is O or S or $NR^9$ wherein $R^9$ is a hydrogen atom (H), $C_{1-4}$alkyl or $C_{1-4}$fluoroalkyl; none, one, two or three of J, L, M and Q are nitrogen; and the remaining of J, L, M and Q are independently CH or $CR^6$ where $R^6$, independently of any other $R^6$ present, is as defined therein.

The pyrazolo[3,4-b]pyridine compounds of formula (I) and salts thereof disclosed in PCT/EP03/11814 are disclosed as being inhibitors of phosphodiesterase type IV (PDE4), and as being useful for the treatment and/or prophylaxis of an inflammatory and/or allergic diseases such as chronic obstructive pulmonary disease (COPD), asthma, rheumatoid arthritis, or allergic rhinitis.

THE INVENTION

We have now found new pyrazolo[3,4-b]pyridine 5-carboxamide compounds, having a certain type of (branched-alkyl)amino substituent at the 4-position of the pyrazolo[3,4-b]pyridine ring system, which inhibit phosphodiesterase type IV (PDE4).

We have also found that the Examples disclosed herein, which are 4-(branched-alkyl)amino pyrazolo[3,4-b]pyridine 5-carboxamides according to the present invention, are more potent PDE4 inhibitors than PDE5 inhibitors (i.e. they are PDE4-selective inhibitors compared to PDE5 inhibition). The Examples disclosed herein according to the present invention also appear to have a higher level of selectivity for PDE4 inhibition over (undesirable) PDE5 inhibition, i.e. a higher PDE4-PDE5 selectivity, than that of Example 1 or Example 19 of U.S. Pat. No. 3,979,399 (E.R. Squibb & Sons).

The present invention therefore provides a compound of formula (I) or a salt thereof (in particular, a pharmaceutically acceptable salt thereof):

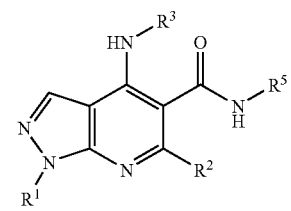

(I)

wherein:
$R^1$ is ethyl, n-propyl, isopropyl, $C_2$fluoroalkyl, or —$CH_2CH_2OH$;
$R^2$ is a hydrogen atom (H), methyl, ethyl, n-propyl, isopropyl, $C_{1-2}$fluoroalkyl, cyclopropyl or (cyclopropyl)methyl-;
$NHR^3$ has the sub-formula (nhr3):

(nhr3)

wherein, in sub-formula (nhr3), the —NH— connection point of the NHR$^3$ group to the bicyclic ring system of formula (I) is underlined, and wherein R$^{3a}$ is methyl or ethyl;

R$^{3b}$ is a hydrogen atom (H), methyl or ethyl,

R$^{3c}$ is a hydrogen atom (H), methyl or ethyl,

R$^{3d}$ is a hydrogen atom (H), methyl or ethyl, and

R$^{3e}$ is a hydrogen atom (H) or methyl, provided that:

(a) R$^{3b}$ is methyl or ethyl; and/or (b) R$^{3c}$ and R$^{3d}$ are independently methyl or ethyl;

and provided that:

(c) when R$^{3c}$ is ethyl and/or when R$^{3d}$ is ethyl and/or when R$^{3e}$ is methyl, then: R$^{3a}$ is methyl and/or R$^{3b}$ is a hydrogen atom (H) or methyl;

and wherein:

R$^5$ is C$_{3-8}$alkyl; C$_{3-8}$cycloalkyl optionally substituted by a C$_{1-2}$alkyl group; or —(CH$_2$)$_n^4$—C$_{3-8}$cycloalkyl optionally substituted, in the —(CH$_2$)$_n^4$— moiety or in the C$_{3-8}$cycloalkyl moiety, by a C$_{1-2}$alkyl group, wherein n$^4$ is 1, 2 or 3;

or R$^5$ is C$_{2-6}$alkyl substituted by one or two independent substituents R$^{11}$;

wherein each substituent R$^{11}$, independently of any other R$^{11}$ substituent present, is: hydroxy (OH); C$_{1-6}$alkoxy; phenyloxy; benzyloxy; —NR$^{12}$R$^{13}$; —NR$^{15}$—C(O)R$^{16}$; —NR$^{15}$—C(O)—NH—R$^{15}$; or —NR$^{15}$—SO$_2$R$^{16}$; and wherein any R$^{11}$ substituent which is OH, alkoxy or —NR$^{12}$R$^{13}$ is not substituted at the carbon atom, of any R$^5$ substituted alkyl, which is bonded to the nitrogen of NHR$^5$;

or R$^5$ is —(CH$_2$)$_n^{12}$—SO$_2$—NR$^{12}$R$^{13}$ or —(CH$_2$)$_n^{12}$—SO$_2$R$^{16}$; wherein n$^{12}$ is 2, 3 or 4; or R$^5$ is —(CH$_2$)$_n^{13}$-Het wherein n$^{13}$ is 0, 1, 2, 3 or 4 and Het is a 4-, 5-, 6- or 7-membered saturated or partly-saturated heterocyclic ring containing one or two ring-hetero-atoms independently selected from O, S, and N; wherein any ring-hetero-atoms present are not bound to the —(CH$_2$)$_n^{13}$— moiety when n$^{13}$ is 1 and are not bound to the nitrogen of NHR$^5$ when n$^{13}$ is 0; wherein any ring-nitrogens which are present and which are not unsaturated (i.e. which do not partake in a double bond) are present as NR$^{17}$; and wherein one or two of the carbon ring-atoms independently are optionally substituted by C$_{1-2}$alkyl;

or R$^5$ has the sub-formula (x), (xa), (y), (y1), (z) or (za):

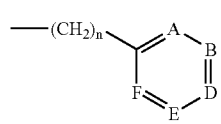

(x)

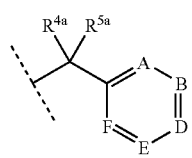

(xa)

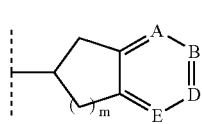

(y)

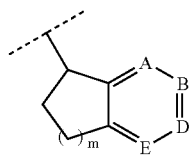

(y1)

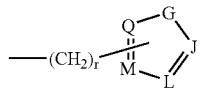

(z)

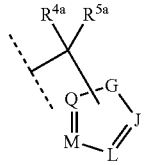

(za)

wherein in sub-formula (x), n=0, 1 or 2; in sub-formula (y) and (y1), m=1 or 2; and in sub-formula (z), r=0, 1 or 2;

wherein sub-formula (y) and (y1), independently, are optionally substituted by oxo (=O) at a ring carbon adjacent the 6-membered aromatic ring;

and wherein, in sub-formula (xa) and (za):

R$^{4a}$ is a hydrogen atom (H); methyl, ethyl, n-propyl, iso-propyl, C$_{1-2}$fluoroalkyl, cyclopropyl, —CH$_2$OR$^{4aa}$, —CH(Me)OR$^{4aa}$, or —CH$_2$CH$_2$OR$^{4aa}$, wherein R$^{4aa}$ is a hydrogen atom (H), methyl (Me), or C$_1$ fluoroalkyl such as CF$_3$ or CHF$_2$; and R$^{5a}$ is a hydrogen atom (H); C$_{1-8}$alkyl (e.g. C$_{1-6}$alkyl or C$_{1-4}$alkyl); C$_{1-3}$fluoroalkyl; C$_{3-8}$cycloalkyl optionally substituted by a C$_{1-2}$alkyl group; or —(CH$_2$)$_n^{4a}$—C$_{3-8}$cycloalkyl optionally substituted, in the —(CH$_2$)$_n^{4a}$— moiety or in the C$_{3-8}$cycloalkyl moiety, by a C$_{1-2}$alkyl group, wherein n$^{4a}$ is 1 or 2;

or R$^{5a}$ is C$_{1-4}$alkyl substituted by one substituent R$^{11a}$; wherein R$^{11a}$ is: hydroxy (OH); C$_{1-6}$alkoxy; C$_{1-2}$fluoroalkoxy; phenyloxy; (monofluoro- or difluoro-phenyl)oxy; (monomethyl- or dimethyl-phenyl)oxy; benzyloxy; NR$^{12}$R$^{13}$; NR$^{15}$—C(O)R$^{16}$; —NR$^{15}$—C(O)—NH—R$^{15}$; or —NR$^{15}$—S(O)$_2$R$^{16}$;

or R$^{5a}$ is C$_{2-4}$alkyl substituted on different carbon atoms by two hydroxy (OH) substituents;

or R$^{5a}$ is —(CH$_2$)$_n^{11a}$—C(O)R$^{16}$; —(CH$_2$)$_n^{11a}$—C(O)NR$^{12}$R$^{13}$; CHR$^{19a}$—C(O)NR$^{12}$R$^{13}$; —(CH$_2$)$_n^{11a}$—C(O)OR$^{16}$; —(CH$_2$)$_n^{11a}$—C(O)OH; —CHR$^{19a}$—C(O)OR$^{16}$; —CHR$^{19a}$—C(O)OH; —(CH$_2$)$_n^{11a}$—S(O)$_2$—NR$^{12}$R$^{13}$; —(CH$_2$)$_n^{11a}$—S(O)$_2$R$^{16}$; or —(CH$_2$)$_n^{11a}$—CN; wherein n$^{11a}$ is 0, 1, 2 or 3 (wherein for each R$^{5a}$ group n$^{11a}$ is independent of the value of n$^{11a}$ in other R$^{5a}$ groups), and wherein R$^{19a}$ is C$_{1-2}$alkyl;

or R$^{5a}$ is —(CH$_2$)$_n^{13a}$-Het$^4$, wherein n$^{13a}$ is 0, 1 or 2 and Het$^4$ is a 4-, 5-, 6- or 7-membered saturated or unsaturated heterocyclic ring, other than —NR$^{12}$R$^{13}$, containing one or two ring-hetero-atoms independently selected from O, S, and N; wherein any ring-hetero-atoms present are not bound to the —(CH$_2$)$_n^{13a}$— moiety when n$^{13a}$ is 0; wherein any ring-nitrogens which are present and which are not unsaturated (i.e. which do not partake in a double bond) and which are not connecting nitrogens (i.e. which are not nitrogens bound to the —(CH$_2$)$_n^{13a}$— moiety or to the carbon atom to which R$^{5a}$ is attached) are present as NR$^{17a}$; and wherein one or two of the carbon ring-atoms are independently optionally substituted by C$_{1-2}$alkyl;

or $R^{5a}$ is phenyl (Ph), —CH$_2$-Ph, —CHMe-Ph, —CHEt-Ph, CMe$_2$Ph, or —CH$_2$CH$_2$-Ph, wherein the phenyl ring Ph is optionally substituted with one or two substituents independently being: a halogen atom; C$_{1-4}$alkyl (e.g. C$_{1-2}$alkyl); C$_{1-2}$fluoroalkyl (e.g. trifluoromethyl); C$_{1-4}$alkoxy (e.g. C$_{1-2}$alkoxy); C$_{1-2}$fluoroalkoxy (e.g. trifluoromethoxy or difluoromethoxy); cyclopropyl; cyclopropyloxy; —C(O)—C$_{1-4}$alkyl; —C(O)OH; —C(O)—OC$_{1-4}$alkyl; C$_{1-4}$alkyl-S(O)$_2$—; C$_{1-4}$alkyl-S(O)$_2$—NR$^{8a}$—; R$^{7a}$R$^{8a}$N—S(O)$_2$—; R$^{7a}$R$^{8a}$N—C(O)—; —NR$^{8a}$—C(O)—C$_{1-4}$alkyl; R$^{7a}$R$^{8a}$N; OH; nitro (—NO$_2$); or cyano (—CN);

or $R^{4a}$ and $R^{5a}$ taken together are —(CH$_2$)$_{p^1}$— or —(CH$_2$)$_{p^3}$—X$^5$—(CH$_2$)$_{p^4}$—, in which: X$^5$ is O or NR$^{17a}$; p$^1$=2, 3, 4, 5 or 6, and p$^3$ and p$^4$ independently are 1, 2 or 3 provided that if p$^3$ is 3 then p$^4$ is 1 or 2 and if p$^4$ is 3 then p$^3$ is 1 or 2;

provided that at least one of R$^{4a}$ and R$^{5a}$ is not a hydrogen atom (H);

and wherein, in sub-formula (x) and in sub-formula (xa):

A is C—R$^{6A}$, nitrogen (N) or nitrogen-oxide (N$^+$—O$^-$),
B is C—R$^{6B}$, nitrogen (N) or nitrogen-oxide (N$^+$—O$^-$),
D is C—R$^{6D}$, nitrogen (N) or nitrogen-oxide (N$^+$—O$^-$),
E is C—R$^{6E}$, nitrogen (N) or nitrogen-oxide (N$^+$—O$^-$),
F is C—R$^{6F}$, nitrogen (N) or nitrogen-oxide (N$^+$—O$^-$),
wherein, R$^{6A}$, R$^{6B}$, R$^{6D}$, R$^{6E}$ and R$^{6F}$ independently are: a hydrogen atom (H), a halogen atom; C$_{1-6}$alkyl (e.g. C$_{1-4}$alkyl or C$_{1-2}$alkyl); C$_{1-4}$fluoroalkyl (e.g. C$_{1-2}$fluoroalkyl); C$_{3-6}$cycloalkyl; C$_{1-4}$alkoxy (e.g. C$_{1-2}$alkoxy); C$_{1-2}$fluoroalkoxy; C$_{3-6}$cycloalkyloxy; —C(O)R$^{16a}$; —C(O)OR$^{30}$; —S(O)$^2$—R$^{16a}$ (e.g. C$_{1-2}$alkyl-S(O)$_2$—); R$^{16a}$—S(O)$_2$—NR$^{15a}$— (e.g. C$_{1-2}$alkyl-S(O)$_2$—NH—); R$^7$R$^8$N—S(O)$_2$—; C$_{1-2}$alkyl-C(O)—R$^{15a}$N—S(O)$_2$—; C$_{1-4}$alkyl-S(O)—, Ph-S(O)—, R$^7$R$^8$N—CO—; —NR$^{15a}$—C(O)R$^{16a}$; R$^7$R$^8$N; nitro (—NO$_2$); OH (including any tautomer thereof); C$_{1-4}$alkoxymethyl; C$_{1-4}$alkoxyethyl; C$_{1-2}$alkyl-S(O)$_2$—CH$_2$—; R$^7$R$^8$N—S(O)$_2$—CH$_2$—; C$_{1-2}$alkyl-S(O)$_2$—NR$^{15a}$—CH$_2$—; —CH$_2$—OH; —CH$_2$CH$_2$—OH; —CH$_2$—NR$^7$R$^8$; —CH$_2$—CH$_2$—NR$^7$R$^8$; —CH$_2$—C(O)OR$^{30}$; —CH$_2$—C(O)—NR$^7$R$^8$; —CH$_2$—NR$^{15a}$—C(O)—C$_{1-3}$alkyl; —(CH$_2$)$_n$$^{14}$-Het$^1$ where n$^{14}$ is 0 or 1; cyano (—CN); Ar$^{5b}$; or phenyl, pyridinyl or pyrimidinyl wherein the phenyl, pyridinyl or pyrimidinyl independently are optionally substituted by one or two of fluoro, chloro, C$_{1-2}$alkyl, C$_1$ fluoroalkyl, C$_{1-2}$alkoxy or C$_1$ fluoroalkoxy;

and/or two adjacent groups selected from R$^{6A}$, R$^{6B}$, R$^{6D}$, R$^{6E}$ and R$^{6F}$ are taken together and are: —CH═CH—CH═CH$_2$—, —(CH$_2$)$_n$$^{14a}$— where n$^{14a}$ is 3, 4 or 5 (e.g. 3 or 4), —O—(CMe$_2$)—O—, —O—(CH$_2$)$_n$$^{14b}$—O— where n$^{14b}$ is 1 or 2; —CH═CH—NR$^{15b}$—; —N═CH—NR$^{15b}$—; —CH═N—NR$^{15b}$—; —N═N—NR$^{15b}$—; —CH═CH—O—; —N═CH—O—; —CH═CH—S—; or —N═CH—S—; wherein R$^{15b}$ is H or C$_{1-2}$alkyl;

provided that:
at least two of A, B, D, E and F are independently C—H (carbon-hydrogen), C—F (carbon-fluorine), nitrogen (N), or nitrogen-oxide (N$^+$—O$^-$);
and no more than two of A, B, D, E and F are independently nitrogen or nitrogen-oxide (N$^+$—O$^-$),
and no more than one of A, B, D, E and F is nitrogen-oxide (N$^+$—O$^-$);

and wherein, in sub-formula (z) and in sub-formula (za):
G is O or S or NR$^9$ wherein R$^9$ is a hydrogen atom (H), C$_{1-4}$alkyl, or C$_{1-2}$fluoroalkyl;
J is C—R$^{6J}$, C-[connection point to formula (I)], or nitrogen (N),
L is C—R$^{6L}$, C-[connection point to formula (I)], or nitrogen (N),
M is C—R$^{6M}$, C-[connection point to formula (I)], or nitrogen (N),
Q is C—R$^{6Q}$, C-[connection point to formula (I)], or nitrogen (N),
wherein, R$^{6J}$, R$^{6L}$, R$^{6M}$ and R$^{6Q}$ independently are: a hydrogen atom (H), a halogen atom; C$_{1-4}$alkyl (e.g. C$_{1-2}$alkyl); C$_{1-3}$fluoroalkyl (e.g. C$_{1-2}$fluoroalkyl); C$_{3-6}$cycloalkyl; C$_{1-4}$alkoxy (e.g. C$_{1-2}$alkoxy); C$_{1-2}$fluoroalkoxy; C$_{3-6}$cycloalkyloxy; OH (including any tautomer thereof); or phenyl optionally substituted by one or two substituents independently being fluoro, chloro, C$_{1-2}$alkyl, C$_1$ fluoroalkyl, C$_{1-2}$alkoxy or C$_1$ fluoroalkoxy;

provided that:
at least two of J, L, M and Q are independently C—H, C—F, C—C$_{1-2}$alkyl (e.g. C-Me), C-[connection point to formula (I)], or nitrogen (N);
and no more than three of J, L, M and Q are nitrogen (N);
and wherein:

R$^7$ and R$^8$ are independently a hydrogen atom (H); C$_{1-4}$alkyl (e.g. C$_{1-2}$alkyl such as methyl); C$_{3-6}$cycloalkyl; or phenyl optionally substituted by one or two substituents independently being: fluoro, chloro, C$_{1-2}$alkyl, C$_1$ fluoroalkyl, C$_{1-2}$alkoxy or C$_1$ fluoroalkoxy;

or R$^7$ and R$^8$ together are —(CH$_2$)$_n$$^6$— or —C(O)—(CH$_2$)$_n$$^7$— or —C(O)—(CH$_2$)$_n$$^{10}$—C(O)— or —(CH$_2$)$_n$$^8$—X$^7$—(CH$_2$)$_n$$^9$— or —C(O)—X$^7$—(CH$_2$)$_n$$^{10}$— in which: n$^6$ is 3, 4, 5 or 6, n$^7$ is 2, 3, 4, or 5, n$^8$ and n$^9$ and n$^{10}$ independently are 2 or 3, and X$^7$ is O or NR$^{14}$;

R$^{7a}$ is a hydrogen atom (H) or C$_{1-4}$alkyl;
R$^{8a}$ is a hydrogen atom (H) or methyl;
R$^{12}$ and R$^{13}$ (independent of any other R$^{12}$ or R$^{13}$) independently are H; C$_{1-4}$alkyl (e.g. C$_{1-2}$alkyl); C$_{3-6}$cycloalkyl; or phenyl optionally substituted by one or two substituents independently being: fluoro, chloro, C$_{1-2}$alkyl, C$_1$fluoroalkyl, C$_{1-2}$alkoxy or C$_1$ fluoroalkoxy;

or R$^{12}$ and R$^{13}$ (independent of any other R$^{12}$ or R$^{13}$) together are —(CH$_2$)$_n$$^{6a}$— or —C(O)—(CH$_2$)$_n$$^{7a}$— or —C(O)—(CH$_2$)$_n$$^{10a}$—C(O)— or —(CH$_2$)$_n$$^{8a}$—X$^{12}$—(CH$_2$)$_n$$^{9a}$— or —C(O)—X$^{12}$—(CH$_2$)$_n$$^{10a}$— in which: n$^{6a}$ is 3, 4, 5 or 6, n$^{7a}$ is 2, 3, 4, or 5, n$^{8a}$ and n$^{9a}$ and n$^{10a}$ independently are 2 or 3 and X$^{12}$ is O or NR$^{14a}$;

R$^{14}$, R$^{14a}$ and R$^{17a}$ (independent of any other R$^{14}$, R$^{14a}$ or R$^{17a}$) independently are: a hydrogen atom (H); C$_{1-4}$alkyl (e.g. C$_{1-2}$alkyl); C$_{1-2}$fluoroalkyl (e.g. CF$_3$); cyclopropyl; —C(O)—C$_{1-4}$alkyl (e.g. —C(O)Me); —C(O)NR$^{7a}$R$^{8a}$ (e.g. —C(O)NH$_2$); or —S(O)$_2$—C$_{1-4}$alkyl (e.g. —S(O)$_2$Me);

R$^{15}$, independent of any other R$^{15}$, is a hydrogen atom (H); C$_{1-4}$alkyl (e.g. $^t$Bu or C$_{1-2}$alkyl e.g. methyl); C$_{3-6}$cycloalkyl; or phenyl optionally substituted by one or two substituents independently being: a halogen atom, C$_{1-2}$alkyl, C$_1$ fluoroalkyl, C$_{1-2}$alkoxy or C$_1$ fluoroalkoxy;

R$^{15a}$, independent of any other R$^{15a}$, is a hydrogen atom (H) or C$_{1-4}$alkyl;

R$^{16}$, independent of any other R$^{16}$, is: C$_{1-4}$alkyl (e.g. C$_{1-2}$alkyl); C$_{3-6}$cycloalkyl (e.g. C$_{5-6}$cycloalkyl); C$_{3-6}$cycloalkyl-CH$_2$— (e.g. C$_{5-6}$cycloalkyl-CH$_2$—); or phenyl or benzyl, wherein the phenyl and benzyl are independently optionally substituted on their ring by one or two substituents independently being fluoro, chloro, methyl, C$_1$ fluoroalkyl, methoxy or C$_1$ fluoroalkoxy;

R$^{16a}$, independent of any other R$^{16a}$, is:
C$_{1-6}$alkyl (e.g. C$_{1-4}$alkyl or C$_{1-2}$alkyl);
C$_{3-6}$cycloalkyl (e.g. C$_{5-6}$cycloalkyl) optionally substituted by one oxo (═O), OH or C$_{1-2}$alkyl substituent (e.g. optionally substituted at the 3- or 4-position of a C$_{5-6}$cycloalkyl ring; and/or preferably unsubstituted C$_{3-6}$cycloalkyl);

$C_{3-6}$cycloalkyl-$CH_2$— (e.g. $C_{5-6}$cycloalkyl-$CH_2$—);

pyridinyl (e.g. pyridin-2-yl) optionally substituted on a ring carbon atom by one of: a halogen atom, $C_{1-2}$alkyl, $C_1$ fluoroalkyl, $C_{1-2}$alkoxy or $C_1$ fluoroalkoxy;

$Ar^{5c}$;

phenyl optionally substituted by one or two substituents independently being: a halogen atom, $C_{1-2}$alkyl, $C_1$ fluoroalkyl, $C_{1-2}$alkoxy or $C_1$ fluoroalkoxy;

benzyl optionally substituted on its ring by one or two substituents independently being: a halogen atom, $C_{1-2}$alkyl, $C_1$ fluoroalkyl, $C_{1-2}$alkoxy or $C_1$ fluoroalkoxy; or a 4-, 5-, 6- or 7-membered saturated heterocyclic ring connected at a ring-carbon and containing one or two ring-hetero-atoms independently selected from O, S, and N; wherein any ring-nitrogens which are present are present as $NR^{27}$ where $R^{27}$ is H, $C_{1-2}$alkyl or —C(O)Me; and wherein the ring is optionally substituted at carbon by one $C_{1-2}$alkyl or oxo (=O) substituent, provided that any oxo (=O) substituent is substituted at a ring-carbon atom bonded to a ring-nitrogen;

$R^{17}$, independent of any other $R^{17}$, is a hydrogen atom (H); $C_{1-4}$alkyl (e.g. $C_{1-2}$alkyl); $C_{1-2}$fluoroalkyl; $C_{3-6}$cycloalkyl; —$(CH_2)_p^6$—C(O)$R^{16}$ wherein $p^6$ is 0, 1, 2 or 3 (preferably $p^6$ is 0); —$(CH_2)_p^6$—C(O)$NR^{12}R^{13}$; —$(CH_2)_p^6$—C(O)O$R^{16}$; —$(CH_2)_p^6$—C(O)OH; —SO$_2R^{16}$; —C(O)—$CH_2$—$NR^{12}R^{13}$; —C(O)—$CH_2$—$NR^{15a}$—C(O)—$C_{1-3}$alkyl; —C(O)—$CH_2$—O—$C_{1-3}$alkyl; or phenyl or benzyl wherein the phenyl or benzyl is optionally substituted on their ring by one or two substituents independently being: a halogen atom, $C_{1-2}$alkyl, $C_1$ fluoroalkyl, $C_{1-2}$alkoxy or $C_1$ fluoroalkoxy;

$R^{30}$, independent of any other $R^{30}$, is a hydrogen atom (H), $C_{1-4}$alkyl or $C_{3-6}$cycloalkyl;

$Ar^{5b}$ and $Ar^{5c}$ independently is/are a 5-membered aromatic heterocyclic ring containing one O, S or $NR^{15a}$ in the 5-membered ring, wherein the 5-membered ring can optionally additionally contain one or two N atoms, and wherein the heterocyclic ring is optionally substituted on a ring carbon atom by one of: a halogen atom, $C_{1-2}$alkyl, $C_1$ fluoroalkyl, —$CH_2$OH, —$CH_2$—O$C_{1-2}$alkyl, OH (including the keto tautomer thereof) or —$CH_2$—$NR^{28}R^{29}$ wherein $R^{28}$ and $R^{29}$ independently are H or methyl; and $Het^1$, independent of any other $Het^1$, is a 4-, 5-, 6- or 7-membered saturated heterocyclic ring connected at a ring-carbon and containing one or two ring-hetero-atoms independently selected from O, S, and N; wherein any ring-nitrogens which are present are present as $NR^{31}$ where $R^{31}$ is H, $C_{1-2}$alkyl or —C(O)Me; and wherein the ring is optionally substituted at carbon by one $C_{1-2}$alkyl or oxo (=O) substituent, provided that any oxo (=O) substituent is substituted at a ring-carbon atom bonded to a ring-nitrogen.

In compounds, for example in the compounds of formula (I) (or formula (IA) or formula (IB), see later), an "alkyl" group or moiety may be straight-chain or branched. Alkyl groups, for example $C_{1-8}$alkyl or $C_{1-6}$alkyl or $C_{1-4}$alkyl or $C_{1-3}$alkyl or $C_{1-2}$alkyl, which may be employed include $C_{1-6}$alkyl or $C_{1-4}$alkyl or $C_{1-3}$alkyl or $C_{1-2}$alkyl such as methyl, ethyl, n-propyl, n-butyl, n-pentyl, or n-hexyl or any branched isomers thereof such as isopropyl, t-butyl, sec-butyl, isobutyl, 3-methylbutan-2-yl, 2-ethylbutan-1-yl, or the like.

A corresponding meaning is intended for "alkoxy", "alkylene", and like terms derived from alkyl. For example, "alkoxy" such as $C_{1-6}$alkoxy or $C_{1-4}$alkoxy or $C_{1-2}$alkoxy includes methoxy, ethoxy, propyloxy, and oxy derivatives of the alkyls listed above. "Alkylsulfonyl" such as $C_{1-4}$alkylsulfonyl includes methylsulfonyl (methanesulfonyl), ethylsulfonyl, and others derived from the alkyls listed above. "Alkylsulfonyloxy" such as $C_{1-4}$alkylsulfonyloxy includes methanesulfonyloxy (methylsulfonyloxy), ethanesulfonyloxy, et al. "Cycloalkyl", for example $C_{3-8}$cycloalkyl, includes cyclopropyl, cyclobutyl, cyclopentyl, cyclohexyl, cycloheptyl, cyclooctyl, and the like. Preferably, a $C_{3-8}$cycloalkyl group is $C_{3-6}$cycloalkyl or $C_{5-6}$cycloalkyl, that is contains a 3-6 membered or 5-6 membered carbocyclic ring.

"Fluoroalkyl" includes alkyl groups with one, two, three, four, five or more fluorine substituents, for example $C_{1-4}$fluoroalkyl or $C_{1-3}$fluoroalkyl or $C_{1-2}$fluoroalkyl such as monofluoromethyl, difluoromethyl, trifluoromethyl, pentafluoroethyl, 2,2,2-trifluoroethyl ($CF_3CH_2$—), 2,2-difluoroethyl ($CHF_2CH_2$—), 2-fluoroethyl ($CH_2FCH_2$—), etc. "Fluoroalkoxy" includes $C_{1-4}$fluoroalkoxy or $C_{1-2}$fluoroalkoxy such as trifluoromethoxy, pentafluoroethoxy, monofluoromethoxy, difluoromethoxy, etc. "Fluoroalkylsulfonyl" such as $C_{1-4}$fluoroalkylsulfonyl includes trifluoromethanesulfonyl, pentafluoroethylsulfonyl, etc. A halogen atom ("halo") present in compounds, for example in the compounds of formula (I), means a fluorine, chlorine, bromine or iodine atom ("fluoro", "chloro", "bromo" or "iodo"), for example fluoro, chloro or bromo.

When the specification states that atom or moiety A is "bonded" or "attached" to atom or moiety B, it means that atom/moiety A is directly bonded to atom/moiety B usually by means of a covalent bond or a double covalent bond, and excludes A being indirectly attached to B via one or more intermediate atoms/moieties (e.g. excludes A-C—B); unless it is clear from the context that another meaning is intended.

When $R^1$ is $C_2$fluoroalkyl it can be pentafluoroethyl or more preferably $C_1$ fluoroalkyl-$CH_2$— such as 2,2,2-trifluoroethyl ($CF_3CH_2$—), 2,2-difluoroethyl ($CHF_2CH_2$—), or 2-fluoroethyl ($CH_2FCH_2$—).

Preferably, $R^1$ is ethyl, n-propyl, $C_2$fluoroalkyl (e.g. $C_1$ fluoroalkyl-$CH_2$— such as $CF_3$—$CH_2$—) or —$CH_2CH_2OH$; for example ethyl, n-propyl or —$CH_2CH_2OH$. Yet more preferably, $R^1$ is ethyl or $C_2$fluoroalkyl. $R^1$ is most preferably ethyl.

Suitably, $R^2$ is a hydrogen atom (H), methyl or ethyl; more suitably a hydrogen atom (H) or methyl; still more suitably a hydrogen atom (H).

Suitably, $R^{3a}$ is methyl.

Suitably, $R^{3b}$ is a hydrogen atom (H) or methyl, for example a hydrogen atom (H).

Preferably, $R^{3e}$ is a hydrogen atom (H).

Suitably, when $R^{3c}$ is ethyl and/or when $R^{3d}$ is ethyl and/or when $R^{3e}$ is methyl, then: $R^{3a}$ is methyl and $R^{3b}$ is a hydrogen atom (H) or methyl.

Suitably, when $R^{3c}$ and/or $R^{3d}$ are independently methyl or ethyl and/or when $R^{3e}$ is methyl, then: $R^{3a}$ is methyl and/or $R^{3b}$ is a hydrogen atom (H) or methyl.

According to one embodiment of the invention, (a), $R^{3b}$ is methyl or ethyl. In this embodiment (a), suitably: $R^{3c}$ and/or $R^{3d}$ independently can be a hydrogen atom (H) or methyl (e.g. H); and/or $R^{3e}$ can be a hydrogen atom (H); and/or $R^{3a}$ and/or $R^{3b}$ can be methyl.

In this embodiment (a), $R^{3c}$, $R^{3d}$ and $R^{3e}$ can for example be hydrogen atoms (H). In this case, $R^{3a}$ and $R^{3b}$ are preferably methyl. In other words, in embodiment (a), $R^3$ is preferably t-butyl (i.e. $NHR^3$ is t-butylamino,

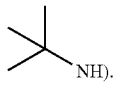

This t-butylamino group has been found to confer good PDE4B/PDE5 selectivity in the Examples disclosed herein.

In a preferable embodiment of the invention, (b), $R^{3c}$ and $R^{3d}$ are independently methyl or ethyl. (This does not exclude the possibility of embodiment (a) also occurring). In this embodiment (b), suitably: $R^{3a}$ is methyl; and/or $R^{3b}$ is a hydrogen atom (H) or methyl (e.g. H); and/or $R^{3c}$ and/or $R^{3d}$ are methyl; and/or $R^{3e}$ is a hydrogen atom (H).

In this embodiment (b), more suitably: $R^{3a}$ is methyl; and $R^{3b}$ and $R^{3e}$ are hydrogen atoms (H). In this case, one or both of $R^{3c}$ and $R^{3d}$ are suitably methyl.

In embodiment (b), preferably, $R^{3a}$, $R^{3c}$ and $R^{3d}$ are methyl; and $R^{3b}$ and $R^{3e}$ are a hydrogen atoms (H). In other words, in embodiment (b), $R^3$ is preferably 1,2-dimethylpropyl (that is, $NHR^3$ is (1,2-dimethylpropyl)amino which is

Preferably, $NHR^3$ has the sub-formula (nhr3a):

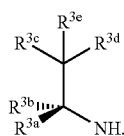

(nhr3a)

Sub-formula (nhr3a) means that more than 50% of the compound or salt present has the stereochemistry shown at the carbon atom bearing the $R^{3a}$ and $R^{3b}$ groups.

Preferably, in sub-formula (nhr3a), the stereochemistry at the carbon atom bearing the $R^{3a}$ and $R^{3b}$ groups is such that there is an enantiomeric excess (e.e.) of 50% or more at the carbon atom bearing the $R^{3a}$ and $R^{3b}$ groups (ignoring the stereochemistry at any other carbon atoms). More preferably, the enantiomeric excess (e.e.) is 70% or more or 80% or more, still more preferably 90% or more, yet more preferably 95% or more, at the carbon atom bearing the $R^{3a}$ and $R^{3b}$ groups (ignoring the stereochemistry at any other carbon atoms).

"Enantiomeric excess" (e.e.) is defined as the percentage of the major isomer present minus the percentage of the minor isomer present (ignoring the stereochemistry at any other carbon atoms). For example, if 95% of major isomer is present and 5% of the minor isomer is present, then the e.e. would be 90%.

Therefore, in embodiment (b), where $R^{3c}$ and $R^{3d}$ are independently methyl or ethyl, $NHR^3$ preferably has the sub-formula (nhr3a). In embodiment (b) and with sub-formula (nhr3a), more preferably $R^{3b}$ is a hydrogen atom (H). In embodiment (b) and with sub-formula (nhr3a), suitably, $R^{3a}$ can be methyl; and/or $R^{3c}$ can be methyl; and/or $R^{3d}$ can be methyl; and/or $R^{3e}$ can be a hydrogen atom (H).

In embodiment (b) and with sub-formula (nhr3a), most preferably, $R^{3a}$ is methyl; $R^{3b}$ is a hydrogen atom (H), $R^{3c}$ and $R^{3d}$ are methyl; and $R^{3e}$ is a hydrogen atom (H). In this case, $NHR^3$ has the following sub-formula:

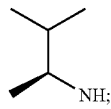

i.e. $NHR^3$ is [(1S)-1,2-dimethylpropyl]amino. (This is the S-isomer). This group has been found to confer good PDE4B/PDE5 selectivity in the Examples disclosed herein.

In another less preferred embodiment, $NHR^3$ has the following sub-formula:

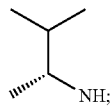

i.e. $NHR^3$ is [(1R)-1,2-dimethylpropyl]amino. (This is the R-isomer). This group has been found to confer PDE4B/PDE5 selectivity in the Examples disclosed herein, but to a lesser extent than in the Examples containing the corresponding S-isomer group.

Where $R^5$ is $C_{3-8}$alkyl, then preferably it is $C_{4-7}$alkyl and/or $C_{3-6}$alkyl, for example $C_6$alkyl such as 2-ethylbutyl. Where $R^5$ is $C_{3-8}$cycloalkyl (e.g. $C_{3-6}$cycloalkyl) optionally substituted by a $C_{1-2}$alkyl group, then preferably the $C_{3-8}$cycloalkyl is not substituted at the ring-carbon bonded to the nitrogen of $NR^4R^5$. Where $R^5$ is optionally substituted $C_{3-8}$cycloalkyl, then more preferably it is $C_{3-8}$cycloalkyl (i.e. unsubstituted), e.g. $C_{3-6}$cycloalkyl (i.e. unsubstituted).

When $R^5$ is optionally substituted $-(CH_2)_{n^4}-C_{3-8}$cycloalkyl wherein $n^4$ is 1, 2 or 3, then $n^4$ is preferably 1 or 2 or more preferably 1, and/or preferably $R^5$ is optionally substituted $-(CH_2)_{n^4}-C_{5-6}$cycloalkyl or optionally substituted $-(CH_2)_{n^4}-C_6$cycloalkyl. When $R^5$ is optionally substituted $-(CH_2)_{n^4}-C_{3-8}$cycloalkyl, preferably it is not substituted. Most preferably $R^5$ is (cyclohexyl)methyl-, that is $-CH_2$-cyclohexyl.

When $R^5$ is $C_{2-6}$alkyl substituted by one or two independent substituents $R^{11}$, it is preferable that $R^5$ is $C_{2-4}$alkyl (e.g. $C_{2-3}$alkyl) substituted by one or two independent substituents $R^{11}$. When $R^5$ is $C_{2-6}$alkyl (e.g. $C_{2-4}$alkyl or $C_{2-3}$alkyl) substituted by one or two independent substituents $R^{11}$, it is preferable that $R^5$ is $C_{2-6}$alkyl (e.g. $C_{2-4}$alkyl or $C_{2-3}$alkyl) substituted by one substituent $R^{11}$. It is more preferable that $R^5$ is $-(CH_2)_{n^5}-R^{11}$ wherein $n^5$ is 2, 3 or 4. Preferably $n^5$ is 2 or 3, more preferably 2.

Preferably, each substituent $R^{11}$, independently of any other $R^{11}$ substituent present, is: $C_{1-6}$alkoxy (e.g. $C_{1-4}$alkoxy such as t-butyloxy, ethoxy or methoxy), $-NR^{15}-C(O)-NH-R^{15}$, or $-NR^{15}-SO_2R^{16}$; most preferably $-NR^{15}-SO_2R^{16}$.

When $R^5$ is $-(CH_2)_{n^{12}}-SO_2-NR^{12}R^{13}$ or $-(CH_2)_{n^{12}}-SO_2R^{16}$, then suitably $n^{12}$ is 1 or 2. Preferably, $R^5$ is not $-(CH_2)_{n^{12}}-SO_2-NR^{12}R^{13}$ or $-(CH_2)_{n^{12}}-SO_2R^{16}$.

When $R^5$ is $-(CH_2)_{n^{13}}$-Het, it is preferable that $n^{13}$ is 0, 1 or 2, more preferably 0 or 1.

Preferably, Het is a 5- or 6-membered saturated or partly-saturated heterocyclic ring and/or preferably is a 4-, 5-, 6- or 7-membered saturated heterocyclic ring. Preferably, the heterocyclic ring Het contains one ring-hetero-atom selected from O, S and N. Preferably, the carbon ring-atoms in Het are not substituted. Het is most preferably one of:

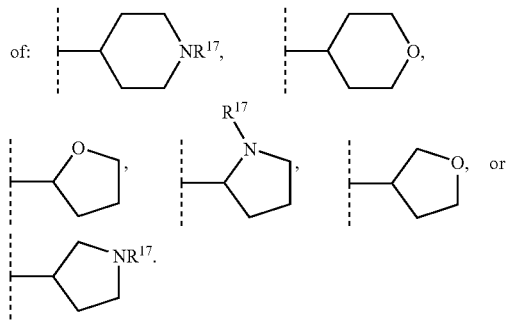

Overall for $R^5$, it is preferable that $R^5$ is $C_{3-8}$alkyl; $C_{3-6}$cycloalkyl (e.g. $C_{5-6}$cycloalkyl); ($C_{5-6}$cycloalkyl)methyl-; —$(CH_2)_{n^5}$—$R^{11}$ wherein $n^5$ is 2 or 3 and $R^{11}$ is —$NR^{15}$—$SO_2R^{16}$; or $R^5$ has the sub-formula (x), (xa), (y), (y1), (z) or (za).

In general, it is preferable that $R^5$ has the sub-formula (x), (xa), (y), (y1), (z) or (za).

When $R^5$ has the sub-formula (x), (xa), (y), (y1), (z) or (za), then preferably $R^5$ has the sub-formula (x), (xa), (y) or (z). More preferably $R^5$ has the sub-formula (x), (xa) or (y), still more preferably (x) or (xa).

Preferably, n is 0 or 1. More preferably, n=1.

Preferably, m=1.

Preferably, r=0 or 1, more preferably 1.

Preferably, in sub-formula (x) and/or in sub-formula (xa), at least three (more preferably at least four) of A, B, D, E and F are independently C—H (carbon-hydrogen), C—F (carbon-fluorine), nitrogen (N), or nitrogen-oxide ($N^+$—$O^-$).

Preferably, in sub-formula (x) and/or in sub-formula (xa), at least two or at least three or at least four of A, B, D, E and F are C—H.

Preferably, in sub-formula (x) and/or in sub-formula (xa), no more than one (more preferably none) of A, B, D, E and F are independently nitrogen or nitrogen-oxide ($N^+$—$O^-$).

Preferably, in sub-formula (x) and/or in sub-formula (xa), none of A, B, D, E and F are nitrogen-oxide ($N^+$—$O^-$).

When $R^5$ has the sub-formula (x), then this is —$(CH_2)_n$—$Ar^X$, wherein $Ar^X$ is

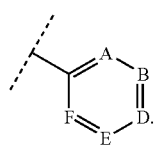

When $R^5$ has the sub-formula (xa), then this is —$(CR^{4a}R^{5a})$—$Ar^X$, wherein $Ar^X$ is

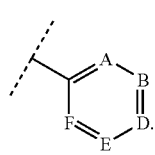

Preferably, $R^5$ has the sub-formula (x) which is —$(CH_2)_n$—$Ar^X$, or has the sub-formula (xa) which is —$(CR^{4a}R^{5a})$—$Ar^X$, and $Ar^X$ has the sub-formula (x1), (x2), (x3), (x4), (x5), (x6), (x7), (x8), (x9), (x10), (x11), (x12), (x13), (x14), (x15) or (x16):

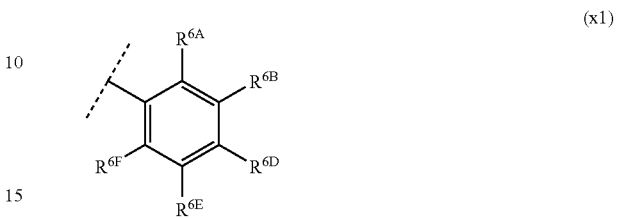

(x1)

(x2)

(x3)

(x4)

(x5)

(x6)

(x7)

(x8)

(x9)

-continued

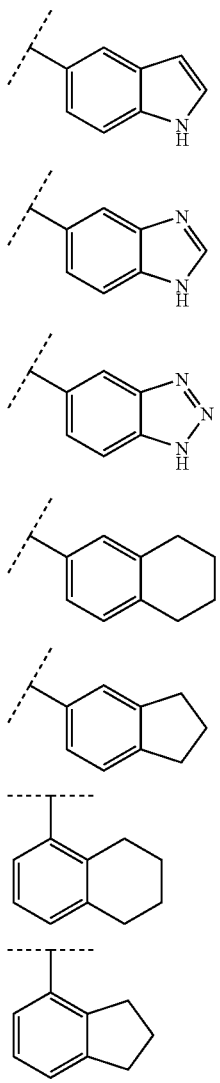

More preferably, $Ar^X$ has the sub-formula (x1), (x2), (x3), (x8), (x13), or (x14). Still more preferably, $Ar^X$ has the sub-formula (x1), (x8), (x13), or (x14). Most preferably, $Ar^X$ has the sub-formula (x1).

In sub-formula (x) and/or in sub-formula (xa), preferably, $R^{6A}$, $R^{6B}$, $R^{6D}$, $R^{6E}$ and/or $R^{6F}$, independently of each other, are: a hydrogen atom (H), a fluorine, chlorine, bromine or iodine atom, methyl, ethyl, n-propyl, isopropyl, $C_4$alkyl, trifluoromethyl, —$CH_2OH$, methoxy, ethoxy, n-propoxy, isopropoxy, $C_1$ fluoroalkoxy (e.g. trifluoromethoxy or difluoromethoxy), cyclohexyloxy; cyclopentyloxy; nitro (—$NO_2$), OH, $C_{1-3}$alkylS(O)$_2$—(such as MeS(O)$_2$—), $C_{1-3}$alkylS(O)$_2$—NH— such as Me-S(O)$_2$—NH—, Me$_2$N—S(O)$_2$—, $H_2N$—S(O)$_2$—, —$CONH_2$, —CONHMe, —C(O)OH, cyano (—CN), NMe$_2$, or $C_{1-2}$alkyl-S(O)$_2$—$CH_2$— such as Me-S(O)$_2$—$CH_2$—.

More preferably, $R^{6A}$, $R^{6B}$, $R^{6D}$, $R^{6E}$ and/or $R^{6F}$, independently of each other, are: is a hydrogen atom (H), a fluorine, chlorine, bromine or iodine atom, methyl, ethyl, n-propyl, isobutyl, trifluoromethyl, —$CH_2OH$, methoxy, ethoxy, n-propoxy, isopropoxy, $C_1$ fluoroalkoxy (e.g. trifluoromethoxy or difluoromethoxy), nitro (—$NO_2$), OH, $C_{1-3}$alkylS(O)$_2$— such as MeS(O)$_2$—, $C_{1-2}$alkylS(O)$_2$—NH— such as Me-S(O)$_2$—NH—, —$CONH_2$, cyano (—CN), or $C_{1-2}$alkylS(O)$_2$—$CH_2$— such as Me-S(O)$_2$—$CH_2$—.

Still more preferably, $R^{6A}$, $R^{6B}$, $R^{6D}$, $R^{6E}$ and/or $R^{6F}$, independently of each other, are: a hydrogen atom (H), a fluorine, chlorine or bromine atom, methyl, ethyl, n-propyl, isopropyl, trifluoromethyl, —$CH_2OH$, methoxy, ethoxy, n-propoxy, difluoromethoxy, nitro (—$NO_2$), OH, MeS(O)$_2$—, Me-S(O)$_2$—NH— or Me-S(O)$_2$—$CH_2$—.

When two adjacent groups selected from $R^{6A}$, $R^{6B}$, $R^{6D}$, $R^{6E}$ and $R^{6F}$ are taken together, then, preferably, when taken together they are: —CH=CH—CH=CH$_2$—, —(CH$_2$)$_n{}^{14a}$— where $n^{14a}$ is 3, 4 or 5 (e.g. 3 or 4), —O—(CMe$_2$)—O—, —O—(CH$_2$)$_n{}^{14b}$—O—where $n^{14b}$ is 1 or 2; —CH=CH—NR$^{15b}$—; —N=CH—NR$^{15b}$—; —N=N—NR$^{15b}$ wherein $R^{15b}$ is H or $C_{1-2}$alkyl (preferably $R^{15b}$ is H). More preferably, in this embodiment, two adjacent groups selected from $R^{6A}$, $R^{6B}$, $R^{6D}$, $R^{6E}$ and $R^{6F}$ are taken together and are: —CH=CH—CH=CH$_2$— or —(CH$_2$)$_n{}^{14a}$— where $n^{14a}$ is 3, 4 or 5 (e.g. 3 or 4).

In sub-formula (x) and/or in sub-formula (xa), suitably, one, two or three of $R^{6B}$, $R^{6D}$ and $R^{6E}$ are other than a hydrogen atom (H).

In sub-formula (x) and/or in sub-formula (xa), for mono-substitution of the ring, then the one substituent selected from $R^{6A}$, $R^{6B}$, $R^{6D}$, $R^{6E}$ and $R^{6F}$ can for example be present at the 2-, 3- or 4-position with respect to the —(CR$^4$R$^5$)— side-chain (i.e. D is CR$^{6D}$ where $R^{6D}$ is other than H). Where there is disubstitution, then 3,4-disubstitution 2,4-disubstitution or 2,3-disubstitution is preferred.

In one preferable embodiment, $Ar^X$ is: phenyl, monoalkyl-phenyl-, mono(fluoroalkyl)-phenyl-, monohalo-phenyl-, monoalkoxy-phenyl-, mono(fluoroalkoxy)-phenyl-, mono(N,N-dimethylamino)-phenyl-, mono(methyl-SO$_2$—NH—)-phenyl-, mono(methyl-SO$_2$—)-phenyl-, dialkyl-phenyl-, monoalkyl-monohalo-phenyl-, mono(fluoroalkyl)-monohalo-phenyl-, dihalo-phenyl-, dihalo-monoalkyl-phenyl-, dihalo-mono(hydroxymethyl)-phenyl-, or dialkoxy-phenyl-, such as 3,4-dimethoxy-phenyl-. The substituents can preferably be further defined, as defined in preferable embodiments herein.

In one preferable embodiment, $Ar^X$ is: monoalkyl-phenyl-, mono(fluoroalkyl)-phenyl-, monohalo-phenyl-, monoalkoxy-phenyl-, mono(fluoroalkoxy)-phenyl-, mono(N,N-dimethylamino)-phenyl-, dialkyl-phenyl-, monoalkyl-monohalo-phenyl-, dihalo-phenyl- or dihalo-monoalkyl-phenyl- or dihalo-mono(hydroxymethyl)-phenyl-.

More preferably, in this embodiment, $Ar^X$ is:

mono$C_{1-4}$alkyl-phenyl- or mono$C_{1-3}$alkyl-phenyl- such as 4-$C_{1-4}$alkyl-phenyl- (e.g. 4-$C_{1-3}$alkyl-phenyl-) or 2-$C_{1-2}$alkyl-phenyl-;

monoC1 fluoroalkyl-phenyl- such as 4-$C_1$ fluoroalkyl-phenyl-;

mono$C_{1-3}$alkoxy-phenyl- such as 4-$C_{1-3}$alkoxy-phenyl-;

mono($C_1$ fluoroalkoxy)-phenyl- such as 4-$C_1$ fluoroalkoxy-phenyl-;

di$C_{1-3}$alkyl-phenyl- or di$C_{1-2}$alkyl-phenyl- or dimethyl-phenyl- such as 3,4-dimethyl-phenyl-, 2,4-dimethyl-phenyl-, 3,5-dimethyl-phenyl-, 2,3-dimethyl-phenyl- or 2,5-dimethyl-phenyl-; more preferably 3,4-dimethyl-phenyl- or 2,4-dimethyl-phenyl-;

mono$C_{1-4}$alkyl-monohalo-phenyl- such as mono$C_{1-2}$alkyl-monohalo-phenyl- or mono$C_{1-2}$alkyl-monochloro-phenyl-, for example 4-methyl-3-chloro-phenyl-, 3-methyl-4-chloro-phenyl-, 2-methyl-4-chloro-phenyl-;

dihalo-phenyl- such as 2-chloro-4-fluorophenyl- or 2,4-difluoro-phenyl- or 4-bromo-2-fluorophenyl- or preferably 4-chloro-2-fluorophenyl-; for example dichloro-phenyl- such as 3,4-dichloro-phenyl- or 2,4-dichloro-phenyl- or 2,6-dichloro-phenyl- or preferably 2,3-dichloro-phenyl-;

dihalo-mono$C_{1-2}$alkyl-phenyl- e.g. 2,4-dichloro-6-methyl-phenyl-; or dihalo-mono(hydroxymethyl)-phenyl- such as 2,3-dichloro-6-(hydroxymethyl)-phenyl-.

In one preferable embodiment, $R^5$ has the sub-formula (x) and is: benzyl, (monoalkyl-phenyl)methyl, [mono(fluoroalkyl)-phenyl]methyl, (monohalo-phenyl)methyl, (monoalkoxy-phenyl)methyl, [mono(fluoroalkoxy)-phenyl]methyl, [mono(N,N-dimethylamino)-phenyl]methyl, [mono(methyl-$SO_2$—NH—)-phenyl]methyl, [mono(methyl-$SO_2$—)-phenyl]methyl, (dialkyl-phenyl)methyl, (monoalkyl-monohalo-phenyl)methyl, [mono(fluoroalkyl)-monohalo-phenyl]methyl, (dihalo-phenyl)methyl, (dihalo-monoalkyl-phenyl)methyl, [dihalo-mono(hydroxymethyl)-phenyl]methyl, or (dialkoxy-phenyl)methyl such as (3,4-dimethoxy-phenyl)methyl. The substituents can preferably be further defined, as defined in preferable embodiments herein.

In one preferable embodiment, $R^5$ is of sub-formula (x) and is: (monoalkyl-phenyl)methyl, [mono(fluoroalkyl)-phenyl]methyl, (monohalo-phenyl)methyl, (monoalkoxy-phenyl)methyl, [mono(fluoroalkoxy)-phenyl]methyl, [mono(N,N-dimethylamino)-phenyl]methyl, (dialkyl-phenyl)methyl, (monoalkyl-monohalo-phenyl)methyl, (dihalo-phenyl)methyl or (dihalo-monoalkyl-phenyl)methyl or [dihalo-mono(hydroxymethyl)-phenyl]methyl. More preferably, in this embodiment, $R^5$ is:

(mono$C_{1-4}$alkyl-phenyl)methyl or (mono$C_{1-3}$alkyl-phenyl)methyl such as (4-$C_{1-4}$alkyl-phenyl)methyl;

(mono$C_1$ fluoroalkyl-phenyl)methyl such as (4-$C_1$ fluoroalkyl-phenyl)methyl;

(mono$C_{1-3}$alkoxy-phenyl)methyl or (mono$C_{1-2}$alkoxy-phenyl)methyl such as (4-$C_{1-3}$alkoxy-phenyl)methyl;

[mono($C_1$ fluoroalkoxy)-phenyl]methyl such as (4-$C_1$ fluoroalkoxy-phenyl)methyl;

(di$C_{1-2}$alkyl-phenyl)methyl or (dimethyl-phenyl)methyl such as (3,4-dimethyl-phenyl)methyl, (2,4-dimethyl-phenyl)methyl, (3,5-dimethyl-phenyl)methyl, (2,3-dimethyl-phenyl)methyl or (2,5-dimethyl-phenyl)methyl; more preferably (3,4-dimethyl-phenyl)methyl or (2,4-dimethyl-phenyl)methyl;

(mono$C_{1-4}$alkyl-monohalo-phenyl)methyl such as (mono$C_{1-2}$alkyl-monohalo-phenyl)methyl or (mono $C_{1-2}$alkyl-monohalo-phenyl)methyl or (mono$C_{1-2}$alkyl-monochloro-phenyl)methyl such as (4-methyl-3-chloro-phenyl)methyl, (3-methyl-4-chloro-phenyl)methyl, (2-methyl-4-chloro-phenyl)methyl;

(dihalo-phenyl)methyl such as (2-chloro-4-fluorophenyl)methyl or (2,4-difluoro-phenyl)methyl or (4-bromo-2-fluorophenyl)methyl or preferably (4-chloro-2-fluorophenyl)methyl; for example (dichloro-phenyl)methyl such as (3,4-dichloro-phenyl)methyl or (2,4-dichloro-phenyl)methyl or (2,6-dichloro-phenyl)methyl or preferably (2,3-dichloro-phenyl)methyl;

(dihalo-mono$C_{1-2}$alkyl-phenyl)methyl e.g. (2,4-dichloro-6-methyl-phenyl)methyl; or

[dihalo-mono(hydroxymethyl)-phenyl]methyl such as [2,3-dichloro-6-(hydroxymethyl)-phenyl]methyl.

Sub-formula (y) and (y1), independently, can be (optionally) substituted by oxo (=O) at a ring carbon adjacent the 6-membered aromatic ring. For example, sub-formula (y) can optionally be

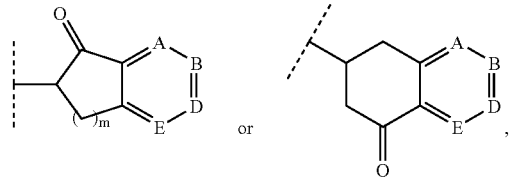

or sub-formula (y1) can optionally be

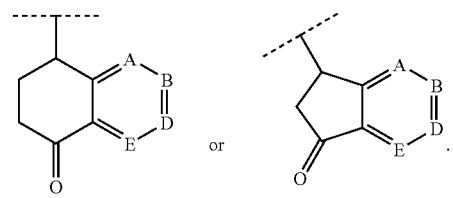

Suitably, sub-formula (y) can be

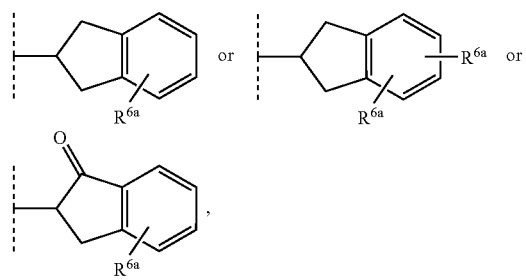

wherein $R^{6a}$ is one of $R^{6A}$, $R^{6B}$, $R^{6D}$, $R^{6E}$ and $R^{6F}$, as defined herein; more suitably hydrogen, fluoro or chloro. Suitably, sub-formula (y) is not substituted by oxo (=O) at the carbon between the 6-membered aromatic ring and the carbon bonded to the nitrogen of $NHR^5$.

Suitably, sub-formula (y1) can be:

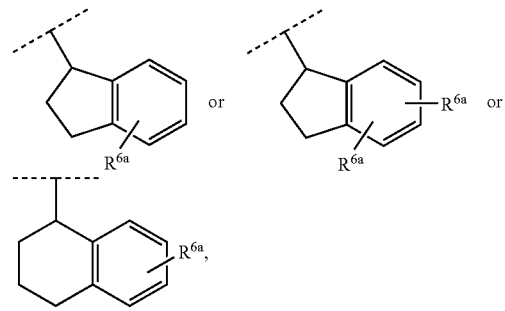

wherein $R^{6a}$ is one of $R^{6A}$, $R^{6B}$, $R^{6D}$, $R^{6E}$ and $R^{6F}$, preferably hydrogen.

In an alternative embodiment, $R^5$ has the sub-formula (z) or (za).

Preferably r is 1. Preferably, $R^9$ is a hydrogen atom (H) or methyl.

Suitably, one (or preferably none) of J, L, M or Q is $CR^6$.

Preferably, in sub-formula (z) and/or in sub-formula (za), $R^{6J}$, $R^{6L}$, $R^{6M}$ and/or $R^{6Q}$ independently are: OH (including any keto tautomer thereof), or more preferably H, $C_{1-2}$alkyl (e.g. methyl) or $C_1$ fluoroalkyl.

Preferably, in sub-formula (z) and/or in sub-formula (za), at least three (for example all) of J, L, M and Q are independently C—H, C—F, C—$C_{1-2}$alkyl (e.g. C-Me), C-[connection point to formula (I)], or nitrogen (N); or at least three (for example all) of J, L, M and Q are independently C—H, C—$C_{1-2}$alkyl (e.g. C-Me), C-[connection point to formula (I)], or nitrogen (N).

Preferably, in sub-formula (z) and/or in sub-formula (za), no more than two (for example no more than one) of J, L, M and Q are nitrogen (N).

Suitably, Q is C-[connection point to formula (I)].

When $R^5$ has the sub-formula (z), then this is —$(CH_2)_r$—$Ar^Z$, wherein $Ar^Z$ is

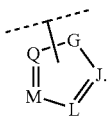

When $R^5$ has the sub-formula (za), then this is —$(CR^{4a}R^{5a})$—$Ar^Z$, wherein $Ar^Z$ is

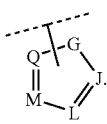

When $Ar^Z$ has the sub-formula (z) and/or in sub-formula (za), then sub-formula (z) and/or in sub-formula (za) can suitably be one of the following:

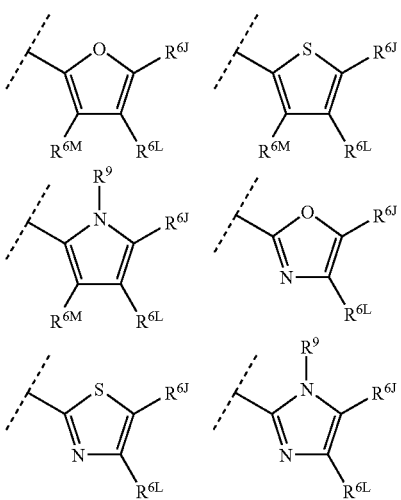

Where $R^{4a}$ is $C_{1-2}$fluoroalkyl, then it can be $C_1$ fluoroalkyl such as monofluoromethyl, difluoromethyl or trifluoromethyl.

$R^{4aa}$ can suitably be a hydrogen atom (H) or methyl (Me), more suitably H.

$R^{4a}$ can for example be a hydrogen atom (H); methyl, ethyl, $C_1$ fluoroalkyl, —$CH_2OH$, —$CH(Me)OH$, —$CH_2CH_2OH$, or —$CH_2OMe$; or preferably a hydrogen atom (H), methyl, ethyl, —$CH_2OH$, or —$CH_2OMe$. More preferably, $R^{4a}$ is methyl, ethyl, —$CH_2OH$, or —$CH_2OMe$; for example methyl, ethyl, or —$CH_2OH$. Most preferably, $R^{4a}$ is ethyl or methyl.

When $R^{5a}$ is $C_{1-4}$alkyl substituted by one substituent $R^{11a}$ or $R^5$ is $C_{2-4}$alkyl (e.g. ethyl or n-propyl) substituted on different carbon atoms by two OH substituents, it is preferable that $R^{5a}$ is $C_{1-4}$alkyl substituted by one substituent $R^{11a}$.

When $R^{5a}$ is $C_{1-4}$alkyl substituted by one substituent $R^{11a}$, it is suitable that $R^{5a}$ is $C_{1-3}$alkyl (e.g. $C_{1-2}$alkyl) substituted by one substituent $R^{11a}$. Suitably, $R^{5a}$ is —$(CH_2)_n^{5a}$—$R^{11a}$ wherein $n^{5a}$ is 1, 2, 3 or 4 or $R^{5a}$ is —$CH(Me)$-$R^{11a}$. Preferably $n^{5a}$ is 1, 2 or 3, more preferably 1 or 2, still more preferably 1.

Suitably, $R^{11a}$ is: hydroxy (OH); $C_{1-4}$alkoxy or $C_{1-2}$alkoxy (such as t-butyloxy, ethoxy or preferably methoxy); $C_1$ fluoroalkoxy; —$NR^{12}R^{13}$; —$NR^{15}$-$C(O)R^{16}$; or —$NR^{15}$—$S(O)_2R^{16}$. Preferably, $R^{11a}$ is hydroxy (OH), $C_{1-4}$alkoxy (e.g. $C_{1-2}$alkoxy), or —$NR^{12}R^{13}$; more preferably OH, ethoxy, methoxy, $NH_2$, NHMe, NHEt, $NMe_2$, pyrrolidin-1-yl or piperidin-1-yl, still more preferably OH, methoxy, $NH_2$, NHMe or $NMe_2$.

Where $R^{5a}$ is $C_{1-8}$alkyl, then preferably it is $C_{1-6}$alkyl or $C_{1-5}$alkyl or $C_{1-4}$alkyl or $C_{1-3}$alkyl. Where $R^{5a}$ is $C_{1-3}$fluoroalkyl then preferably it is $C_{1-2}$fluoroalkyl or $C_1$ fluoroalkyl such as monofluoromethyl, difluoromethyl or trifluoromethyl. Where $R^{5a}$ is $C_{3-8}$cycloalkyl optionally substituted by a $C_{1-2}$alkyl group, then optionally the $C_{3-8}$cycloalkyl is not substituted at the connecting ring-carbon. Where $R^{5a}$ is optionally substituted $C_{3-8}$cycloalkyl, then suitably it is $C_{3-8}$cycloalkyl (i.e. unsubstituted) and/or optionally substituted $C_{3-6}$cycloalkyl such as optionally substituted cyclopropyl or optionally substituted cyclohexyl.

When $R^{5a}$ is optionally substituted —$(CH_2)_n^{4a}$—$C_{3-8}$cycloalkyl, then $n^{4a}$ is preferably 1, and/or suitably $R^{5a}$ is optionally substituted —$(CH_2)_n^{4a}$—$C_{3-6}$cycloalkyl such as optionally substituted —$(CH_2)_n^{4a}$-cyclopropyl or optionally substituted —$(CH_2)_n^{4a}$—$C_6$cycloalkyl. When $R^{5a}$ is optionally substituted —$(CH_2)_n^{4a}$—$C_{3-8}$cycloalkyl, preferably it is not substituted. For example, $R^{5a}$ can be (cyclohexyl)methyl-, that is —$CH_2$-cyclohexyl, or —$CH_2$-cyclopropyl.

When $R^{19a}$ is $C_{1-2}$alkyl, then optionally it can be methyl.

When $R^{5a}$ is —$(CH_2)_n^{11a}$—$C(O)R^{16}$; —$(CH_2)_n^{11a}$—$C(O)NR^{12}R^{13}$; —$CHR^{19a}$—$C(O)NR^{12}R^{13}$; —$(CH_2)_n^{11a}$—$C(O)OR^{16}$; —$(CH_2)_n^{11a}$—$C(O)OH$; —$CHR^{19a}$—$C(O)OR^{16}$; —$CHR^{19a}$—$C(O)OH$; —$(CH_2)_n^{11a}$—$S(O)_2$—$NR^{12}R^{13}$; —$(CH_2)_n^{11a}$—$S(O)_2R^{16}$; or —$(CH_2)_n^{11a}$—CN; then $R^{5a}$ can suitably be —$(CH_2)_n^{11a}$—$C(O)NR^{12}R^{13}$; —$(CH_2)_n^{11a}$—$C(O)OR^{16}$; —$(CH_2)_n^{11a}$—$C(O)OH$; or —$(CH_2)_n^{11a}$—CN; more suitably —$(CH_2)_n^{11a}$—$C(O)OR^{16}$ or —$(CH_2)_n^{11a}$—CN; or preferably —$(CH_2)_n^{11a}$—$C(O)OR^{16}$.

Preferably, $n^{11a}$ is 0, 1 or 2; more preferably $n^{11a}$ is 0 or 1, for example 0.

When $R^{5a}$ is —$(CH_2)_n^{13a}$-$Het^4$, $n^{13a}$ can for example be 0 or 1.

Preferably, $Het^4$ is a 5- or 6-membered saturated or unsaturated heterocyclic ring, and/or preferably $Het^4$ is a 4-, 5-, 6- or 7-membered saturated heterocyclic ring. Preferably, the heterocyclic ring $Het^4$ contains one ring-hetero-atom selected from O, S and N. Preferably, the carbon ring-atoms in $Het^4$ are not substituted. $Het^4$ can for example be:

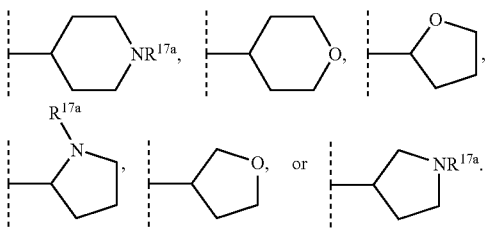

When $R^{5a}$ is phenyl (Ph), —CH$_2$-Ph, —CHMe-Ph, —CHEt-Ph, CMe$_2$Ph, or —CH$_2$CH$_2$-Ph, wherein the phenyl ring Ph is optionally substituted, then suitably Ph is optionally substituted with one of the substituents defined herein. Preferably, $R^{5a}$ is phenyl (Ph) or —CH$_2$-Ph wherein the phenyl ring Ph is optionally substituted with one or two substituents as defined herein.

When $R^{5a}$ is phenyl (Ph), —CH$_2$-Ph, —CHMe-Ph, —CHEt-Ph, CMe$_2$Ph, or —CH$_2$CH$_2$-Ph, wherein the phenyl ring Ph is optionally substituted with one or two substituents, then preferably the phenyl ring Ph is optionally substituted with one or two (e.g. one) substituents independently being: fluoro; chloro; C$_{1-2}$alkyl (e.g. methyl); C$_1$ fluoroalkyl (e.g. trifluoromethyl); C$_{1-2}$alkoxy (e.g. methoxy); or C$_1$ fluoroalkoxy (e.g. trifluoromethoxy or difluoromethoxy). Ph can be unsubstituted.

When $R^{4a}$ and $R^{5a}$ taken together are —(CH$_2$)$_p^1$— or —(CH$_2$)$_p^3$—X$^5$—(CH$_2$)$_p^4$—, in which X$^5$ is O or NR$^{17a}$; then preferably $R^{4a}$ and $R^{5a}$ taken together are —(CH$_2$)$_p^1$—. In one embodiment of the invention, $R^{4a}$ and $R^{5a}$ are not taken together to be either —(CH$_2$)$_p^1$— or —(CH$_2$)$_p^3$—X$^5$—(CH$_2$)$_p^4$—.

When $R^{4a}$ and $R^{5a}$ taken together are —(CH$_2$)$_p^1$—, then p$^1$ can for example be 2, 4, 5 or 6. p$^1$ is preferably 2, 4 or 5, more preferably 2 or 4.

When $R^{4a}$ and $R^{5a}$ taken together are —(CH$_2$)$_p^3$—(CH$_2$)$_p^4$—, in which X$^5$ is O or NR$^{17a}$; then suitably: p$^3$ is 2, and/or p$^4$ is 2, and/or one of p$^3$ and p$^4$ is 1 and the other of p$^3$ and p$^4$ is 2, and/or p$^3$ and p$^4$ are both 1. Suitably, X$^5$ is O. —(CH$_2$)$_p^3$—X$^5$—(CH$_2$)$_p^4$— can for example be —(CH$_2$)$_2$—O—(CH$_2$)$_2$—.

In one embodiment of the invention, $R^{4a}$ and $R^{5a}$ are not taken together as —(CH$_2$)$_p^1$— or —(CH$_2$)$_p^3$—X$^5$—(CH$_2$)$_p^4$—.

Suitably, $R^{7a}$ is H or C$_{1-2}$alkyl, more suitably H or methyl. Suitably, $R^{8a}$ is H.

Preferably, $R^7$ and/or $R^8$ are independently a hydrogen atom (H); C$_{1-2}$alkyl such as methyl; C$_{3-6}$cycloalkyl; or phenyl optionally substituted by one or two (e.g. one) substituents independently being: fluoro, chloro, C$_{1-2}$alkyl, C$_1$ fluoroalkyl, C$_{1-2}$alkoxy or C$_1$ fluoroalkoxy; or $R^7$ and $R^8$ together are —(CH$_2$)$_n^6$— or —(CH$_2$)$_n^8$—X$^7$—(CH$_2$)$_n^9$—wherein X$^7$ is NR$^{14}$ or preferably O.

When $R^7$ is cycloalkyl or optionally substituted phenyl, then preferably $R^8$ is neither cycloalkyl nor optionally substituted phenyl. In this case, $R^8$ can for example be H.

More preferably, $R^7$ and/or $R^8$ independently are a hydrogen atom (H) or C$_{1-2}$alkyl. It is preferable that $R^8$ is a hydrogen atom (H).

Preferably n$^6$ is 4 or 5. Preferably n$^7$ is 3 or 4. Preferably, n$^8$, n$^9$ and/or n$^{10}$ independently is/are 2.

Preferably, $R^{12}$ and/or $R^{13}$ independently are H; C$_{1-2}$alkyl such as methyl; C$_{3-6}$cycloalkyl; or phenyl optionally substituted by one or two (e.g. one) substituents independently being: fluoro, chloro, C$_{1-2}$alkyl, C$_1$ fluoroalkyl, C$_{1-2}$alkoxy or C$_1$ fluoroalkoxy; or $R^{12}$ and $R^{13}$ together are —(CH$_2$)$_n^{6a}$— or —(CH$_2$)$_n^{8a}$—X$^{12}$—(CH$_2$)$_n^{9a}$—in which X$^{12}$ is NR$^{14a}$ or preferably O.

When $R^{12}$ is cycloalkyl or optionally substituted phenyl, then preferably $R^{13}$ is neither cycloalkyl nor optionally substituted phenyl. In this case, $R^{13}$ can for example be H.

More preferably, $R^{12}$ and/or $R^{13}$ independently are a hydrogen atom (H) or C$_{1-2}$alkyl. It is preferable that $R^{13}$ is a hydrogen atom (H).

Preferably n$^{6a}$ is 4 or 5. Preferably n$^{7a}$ is 3 or 4. Preferably, n$^{8a}$, n$^{9a}$ and/or n$^{10a}$ independently is/are 2.

In one embodiment of the invention, NR$^7$R$^8$ and/or NR$^{12}$R$^{13}$, independent of other NR$^7$R$^8$ or NR$^{12}$R$^{13}$, can for example independently be

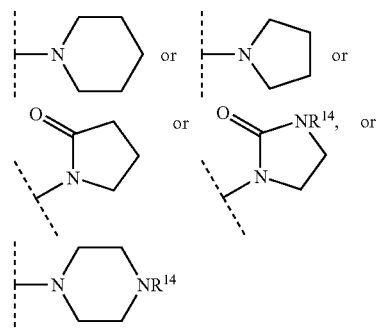

(i.e. $R^{12}$ and $R^{13}$ together or $R^7$ and $R^8$ together are —(CH$_2$)$_2$—N(R$^{14}$)—(CH$_2$)$_2$—), or

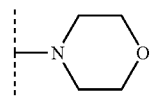

(i.e. $R^{12}$ and $R^{13}$ together or $R^7$ and $R^8$ together are —(CH$_2$)$_2$—O—(CH$_2$)$_2$—), or NMe$_2$.

Suitably, $R^{14}$, $R^{14a}$, and/or $R^{17a}$ independently are: a hydrogen atom (H); C$_{1-2}$alkyl; C$_1$ fluoroalkyl (e.g. CF$_3$); —C(O)Me; —C(O)NH$_2$; or —S(O)$_2$Me. More suitably, $R^{14}$, $R^{14a}$, and/or $R^{17a}$ independently is/are: H, C$_{1-2}$alkyl, or —C(O)Me; or for example H or C$_{1-2}$alkyl.

Suitably, $R^{15}$ is a hydrogen atom (H) or C$_{1-4}$alkyl (e.g. $^t$Bu or C$_{1-2}$alkyl e.g. methyl); more suitably, $R^{15}$ is a hydrogen atom (H).

Where $R^{15a}$, independent of other $R^{15a}$, is a hydrogen atom (H) or C$_{1-4}$alkyl, it can for example be H, $^t$Bu or C$_{1-2}$alkyl such as methyl. Suitably, $R^{15a}$, independent of other $R^{15a}$, is H or C$_{1-2}$alkyl, more preferably H.

Preferably, $R^{15b}$ is H.

Suitably, $R^{16}$ is C$_{1-4}$alkyl (e.g. C$_{1-2}$alkyl) or C$_{3-6}$cycloalkyl (e.g. C$_{5-6}$cycloalkyl); more suitably $R^{16}$ is C$_{1-4}$alkyl (e.g. C$_{1-2}$alkyl).

Preferably, $R^{16a}$ is:
C$_{1-4}$alkyl (e.g. C$_{1-2}$alkyl);
C$_{3-6}$cycloalkyl (e.g. C$_{5-6}$cycloalkyl) optionally substituted by one oxo (=O), OH or methyl substituent (e.g. optionally substituted at the 3- or 4-position of a C$_{5-6}$cycloalkyl ring; and/or preferably unsubstituted C$_{3-6}$cycloalkyl);
C$_{3-6}$cycloalkyl-CH$_2$— (e.g. C$_{5-6}$cycloalkyl-CH$_2$—);

pyridinyl (e.g. pyridin-2-yl) optionally substituted on a ring carbon atom by one of: a halogen atom, $C_{1-2}$alkyl, $C_1$ fluoroalkyl, $C_{1-2}$alkoxy or $C_1$ fluoroalkoxy;

$Ar^{5c}$;

phenyl optionally substituted by one or two substituents independently being: a halogen atom, $C_{1-2}$alkyl, $C_1$ fluoroalkyl, $C_{1-2}$alkoxy or $C_1$ fluoroalkoxy;

benzyl optionally substituted on its ring by one or two substituents independently being: a halogen atom, $C_{1-2}$alkyl, $C_1$ fluoroalkyl, $C_{1-2}$alkoxy or $C_1$ fluoroalkoxy; or a 5- or 6-membered saturated heterocyclic ring connected at a ring-carbon and containing one or two ring-heteroatoms independently selected from O, S, and N; wherein any ring-nitrogens which are present are present as $NR^{27}$ where $R^{27}$ is H, $C_{1-2}$alkyl or —C(O)Me (preferably H or $C_{1-2}$alkyl); and wherein the ring is not substituted at carbon.

More preferably, $R^{16a}$ is: $C_{1-4}$alkyl (e.g. $C_{1-2}$alkyl); unsubstituted $C_{3-6}$cycloalkyl (e.g. unsubstituted $C_{5-6}$cycloalkyl); phenyl optionally substituted by one or two substituents independently being: a halogen atom, $C_{1-2}$alkyl, $C_1$ fluoroalkyl, $C_{1-2}$alkoxy or $C_1$ fluoroalkoxy; or benzyl optionally substituted on its ring by one or two substituents independently being: a halogen atom, $C_{1-2}$alkyl, $C_1$ fluoroalkyl, $C_{1-2}$alkoxy or $C_1$ fluoroalkoxy.

Suitably, $R^{17}$, independent of any other $R^{17}$, is: a hydrogen atom (H); $C_{1-4}$alkyl (e.g. $C_{1-2}$alkyl); $C_{1-2}$fluoroalkyl (e.g. $C_1$ fluoroalkyl such as $CF_3$); cyclopropyl; —C(O)—$C_{1-4}$alkyl (e.g. —C(O)Me); —C(O)$NR^{7a}R^{8a}$ (e.g. —C(O)$NH_2$); or —S(O)$_2$—$C_{1-4}$alkyl (e.g. —S(O)$_2$Me). More suitably, $R^{17}$, independent of any other $R^{17}$, is: H, $C_{1-2}$alkyl, or —C(O)Me; or for example H or $C_{1-2}$alkyl.

Suitably, $R^{30}$, independent of other $R^{30}$, is a hydrogen atom (H) or $C_{1-4}$alkyl, for example H, t-butyl or $C_{1-2}$alkyl.

According to one preferred embodiment, when $R^5$ has the sub-formula (xa) or (za), then preferably it has the sub-formula (xaa) or (zaa) respectively, as follows:

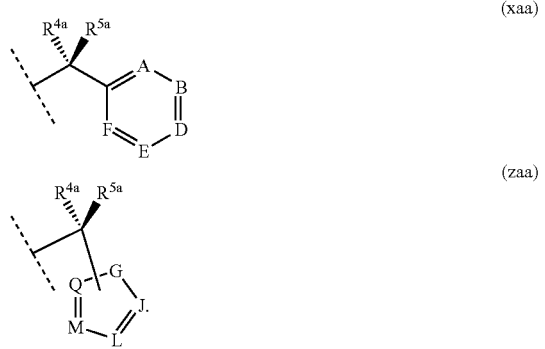

Sub-formulae (xaa) and (zaa) mean that more than 50% of the compound or salt present has the stereochemistry shown at the carbon atom bearing the $R^{4a}$ and $R^{5a}$ groups. Preferably, in sub-formulae (xaa) and (zaa), the stereochemistry at the carbon atom bearing the $R^{4a}$ and $R^{5a}$ groups is such that there is an enantiomeric excess (e.e.) of 50% or more at the carbon atom bearing the $R^{4a}$ and $R^{5a}$ groups (ignoring the stereochemistry at any other carbon atoms). More preferably, the enantiomeric excess (e.e.) is 70% or more or 80% or more, still more preferably 90% or more, yet more preferably 95% or more, at the carbon atom bearing the $R^{4a}$ and $R^{5a}$ groups (ignoring the stereochemistry at any other carbon atoms).

"Enantiomeric excess" (e.e.) is defined as the percentage of the major isomer present minus the percentage of the minor isomer present (ignoring the stereochemistry at any other carbon atoms). For example, if 95% of major isomer is present and 5% of the minor isomer is present, then the e.e. would be 90%.

When $R^5$ has the sub-formula (xaa) or (zaa), then it is preferable that $R^{4a}$ is not a hydrogen atom (H). In sub-formula (xaa) or (zaa), more preferably $R^{4a}$ is methyl, ethyl, $C_1$ fluoroalkyl (such as $CF_3$), —$CH_2OH$, or —$CH_2OMe$; still more preferably $R^{4a}$ is methyl, ethyl, $CF_3$ or —$CH_2OH$; yet more preferably $R^{4a}$ is methyl or ethyl; and most preferably $R^{4a}$ is ethyl.

When $R^5$ has the sub-formula (xaa) or (zaa), it is particularly preferable that $R^{5a}$ is a hydrogen atom (H) and $R^{4a}$ is not a hydrogen atom (H). In sub-formula (xaa) or (zaa), it is more preferable that $R^{5a}$ is a hydrogen atom (H); and $R^{4a}$ is methyl, ethyl, $C_1$ fluoroalkyl (such as $CF_3$), —$CH_2OH$, or —$CH_2OMe$ (e.g. methyl, ethyl, $CF_3$ or —$CH_2OH$). In sub-formula (xaa) or (zaa), it is most preferable that $R^{5a}$ is a hydrogen atom (H); and $R^{4a}$ is methyl or ethyl (preferably ethyl).

In sub-formula (xaa), when $R^{4a}$ is not a hydrogen atom (H), and optionally when $R^{5a}$ is a hydrogen atom (H), it is particularly preferable that $Ar^x$ (e.g. having sub-formula (x1)) is a monocycle. That is, in sub-formula (xaa) and when $R^{4a}$ is not a hydrogen atom (H), it is particularly preferable that two adjacent groups selected from $R^{6A}$, $R^{6B}$, $R^{6D}$, $R^{6E}$ and $R^{6F}$ are not taken together to form part of a second ring.

In an especially preferred embodiment, $NHR^5$ is any one of the $NHR^5$ groups defined in the structures of Examples 1 to 49, 51, and 53 to 57 hereinbelow (the connecting point generally being underlined).

It is particularly preferred that the compound of formula (I) or the salt thereof is:

N-Benzyl-4-{[(1R)-1,2-dimethylpropyl]amino}-1-ethyl-1H-pyrazolo[3,4-b]pyridine-5-carboxamide, 4-{[(1R)-1,2-Dimethylpropyl]amino}-1-ethyl-N-(4-fluorophenyl)-1H-pyrazolo[3,4-b]pyridine-5-carboxamide, 4-{[(1R)-1,2-Dimethylpropyl]amino}-1-ethyl-N-[4-(trifluoromethyl)benzyl]-1H-pyrazolo[3,4-b]pyridine-5-carboxamide, N-(2,3-Dihydro-1H-inden-2-yl)-4-{[(1R)-1,2-dimethylpropyl]amino}-1-ethyl-1H-pyrazolo[3,4-b]pyridine-5-carboxamide, 4-{[(1R)-1,2-Dimethylpropyl]amino}-1-ethyl-N-[4-(methylsulfonyl)benzyl]-1H-pyrazolo[3,4-b]pyridine-5-carboxamide, N-[4-(Difluoromethoxy)benzyl]-4-{[(1S)-1,2-dimethylpropyl]amino}-1-ethyl-1H-pyrazolo[3,4-b]pyridine-5-carboxamide, 4-{[(1S)-1,2-Dimethylpropyl]amino}-1-ethyl-N-[(2-methyl-1,3-thiazol-4-yl)methyl]-1H-pyrazolo[3,4-b]pyridine-5-carboxamide, N-[(5-Chloropyridin-2-yl)methyl]-4-{[(1S)-1,2-dimethylpropyl]amino}-1-ethyl-1H-pyrazolo[3,4-b]pyridine-5-carboxamide, N-(2-Chloro-6-fluorobenzyl)-4-{[(1S)-1,2-dimethylpropyl]amino}-1-ethyl-1H-pyrazolo[3,4-b]pyridine-5-carboxamide, 4-{[(1S)-1,2-Dimethylpropyl]amino}-1-ethyl-N-{1-[4-(methylsulfonyl)phenyl]ethyl}-1H-pyrazolo[3,4-b]pyridine-5-carboxamide, 4-{[(1S)-1,2-Dimethylpropyl]amino}-1-ethyl-N-[(6-methoxypyridin-3-yl)methyl]-1H-pyrazolo[3,4-b]pyridine-5-carboxamide, 4-{[(1S)-1,2-Dimethylpropyl]amino}-1-ethyl-N-{3-[(methylamino)carbonyl]benzyl}-1H-pyrazolo[3,4-b]pyridine-5-carboxamide,
4-{[(1S)-1,2-Dimethylpropyl]amino}-1-ethyl-N-[(1R)-1-phenylpropyl]-1H-pyrazolo[3,4-b]pyridine-5-carboxamide,
4-{[(1S)-1,2-Dimethylpropyl]amino}-N-(2,2-diphenylethyl)-1-ethyl-1H-pyrazolo[3,4-b]pyridine-5-carboxamide,
N-[2-(Dimethylamino)benzyl]-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-(4-fluorobenzyl)-1H-pyrazolo[3,4-b]pyridine-5-carboxamide,
4-{[(1S)-1,2-Dimethylpropyl]amino}-N-(diphenylmethyl)-1-ethyl-1H-pyrazolo[3,4-b]pyridine-5-carboxamide,
4-{[(1S)-1,2-Dimethylpropyl]amino}-1-ethyl-N-{4-[(methylamino)carbonyl]benzyl}-1H-pyrazolo[3,4-b]pyridine-5-carboxamide,
Methyl 4-({[(4-{[(1S)-1,2-dimethylpropyl]amino}-1-ethyl-1H-pyrazolo[3,4-b]pyridin-5-yl)carbonyl]amino}methyl)benzoate,
4-{[(1S)-1,2-Dimethylpropyl]amino}-1-ethyl-N-(4-methoxyphenyl)-1H-pyrazolo[3,4-b]pyridine-5-carboxamide,
4-{[(1S)-1,2-Dimethylpropyl]amino}-1-ethyl-N-(4-hydroxybenzyl)-1H-pyrazolo[3,4-b]pyridine-5-carboxamide,
4-{[(1S)-1,2-Dimethylpropyl]amino}-1-ethyl-N-[3-(trifluoromethyl)benzyl]-1H-pyrazolo[3,4-b]pyridine-5-carboxamide,
4-{[(1S)-1,2-Dimethylpropyl]amino}-1-ethyl-N-(4-methoxybenzyl)-1H-pyrazolo[3,4-b]pyridine-5-carboxamide,
N-(3,4-Difluorobenzyl)-4-{[(1S)-1,2-dimethylpropyl]amino}-1-ethyl-1H-pyrazolo[3,4-b]pyridine-5-carboxamide,
N-(2,6-Difluorobenzyl)-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-[(1R)-1-phenylethyl]-1H-pyrazolo[3,4-b]pyridine-5-carboxamide,
N-(2,5-Difluorobenzyl)-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-(3-fluorobenzyl)-1H-pyrazolo[3,4-b]pyridine-5-carboxamide,
4-{[(1S)-1,2-Dimethylpropyl]amino}-1-ethyl-N-[2-(trifluoromethyl)benzyl]-1H-pyrazolo[3,4-b]pyridine-5-carboxamide,
N-(5-Chloro-2,3-dihydro-1H-inden-2-yl)-4-{[(1S)-1,2-dimethylpropyl]amino}-1-ethyl-1H-pyrazolo[3,4-b]pyridine-5-carboxamide,
Methyl 3-({[(4-{[(1S)-1,2-dimethylpropyl]amino}-1-ethyl-1H-pyrazolo[3,4-b]pyridin-5-yl)carbonyl]amino}methyl)benzoate,
N-[2-(Aminocarbonyl)benzyl]-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-{4-[(methylsulfonyl)amino]benzyl}-1H-pyrazolo[3,4-b]pyridine-5-carboxamide,
4-{[(1S)-1,2-Dimethylpropyl]amino}-1-ethyl-N-{3-[(methylsulfonyl)amino]benzyl}-1H-pyrazolo [3,4-b]pyridine-5-carboxamide,
4-{[(1S)-1,2-Dimethylpropyl]amino}-1-ethyl-N-[4-(trifluoromethyl)benzyl]-1H-pyrazolo [3,4-b]pyridine-5-carboxamide,
N-(2,3-Dihydro-1H-inden-2-yl)-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-[4-(methylsulfonyl)benzyl]-1H-pyrazolo[3,4-b]pyridine-5-carboxamide,
N-Benzyl-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-(4-fluorophenyl)-1H-pyrazolo[3,4-b]pyridine-5-carboxamide,
N-[2-(Aminosulfonyl)ethyl]-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-[(6-oxo-1,6-dihydropyridin-3-yl)methyl]-1H-pyrazolo[3,4-b]pyridine-5-carboxamide,
4-{[(1S)-1,2-Dimethylpropyl]amino}-1-ethyl-N-{2-[(methylsulfonyl)amino]ethyl}-1H-pyrazolo [3,4-b]pyridine-5-carboxamide,
4-{[(1S)-1,2-Dimethylpropyl]amino}-1-ethyl-N-(tetrahydro-2H-pyran-4-yl)-1H-pyrazolo[3,4-b]pyridine-5-carboxamide,
4-{[(1S)-1,2-Dimethylpropyl]amino}-1-ethyl-N-[(1-methyl-1H-pyrazol-4-yl)methyl]-1H-pyrazolo[3,4-b]pyridine-5-carboxamide,
4-{[(1S)-1,2-Dimethylpropyl]amino}-1-ethyl-N-[3-(methylsulfonyl)benzyl]-1H-pyrazolo[3,4-b]pyridine-5-carboxamide,
4-{[(1S)-1,2-Dimethylpropyl]amino}-1-ethyl-N-(pyridin-3-ylmethyl)-1H-pyrazolo[3,4-b]pyridine-5-carboxamide,
N-[3-(Aminocarbonyl)benzyl]-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-(tetrahydrofuran-2-ylmethyl)-1H-pyrazolo[3,4-b]pyridine-5-carboxamide,
N-{4-[(Dimethylamino)sulfonyl]benzyl}-4-{[(1S)-1,2-dimethylpropyl]amino}-1-ethyl-1H-pyrazolo[3,4-b]pyridine-5-carboxamide,
4-{[(1S)-1,2-Dimethylpropyl]amino}-1-ethyl-N-(2-ethylbutyl)-1H-pyrazolo[3,4-b]pyridine-5-carboxamide,
4-(tert-Butylamino)-1-ethyl-N-benzyl-1H-pyrazolo[3,4-b]pyridine-5-carboxamide,
4-(tert-Butylamino)-1-ethyl-N-(4-fluorophenyl)-1H-pyrazolo[3,4-b]pyridine-5-carboxamide,
4-(tert-Butylamino)-1-ethyl-N-[4-(trifluoromethyl)benzyl]-1H-pyrazolo[3,4-b]pyridine-5-carboxamide,
4-(tert-Butylamino)-N-(2,3-dihydro-1H-inden-2-yl)-1-ethyl-1H-pyrazolo[3,4-b]pyridine-5-carboxamide, or
4-(tert-Butylamino)-1-ethyl-N-[4-(methylsulfonyl)benzyl]-1H-pyrazolo[3,4-b]pyridine-5-carboxamide;

or a salt thereof, e.g. a pharmaceutically acceptable salt thereof.

The structures of these specific compounds are given in Examples 1 to 49, 51, and 53 to 57 hereinafter.

Salts, Solvates, Isomers, Tautomeric Forms, Molecular Weights, Etc.

Because of their potential use in medicine, the salts of the compounds of formula (I) are preferably pharmaceutically acceptable. Suitable pharmaceutically acceptable salts can include acid or base addition salts.

A pharmaceutically acceptable acid addition salt can be formed by reaction of a compound of formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base addition salt can be formed by reaction of a compound of formula (I) with a suitable inorganic or organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration.

Other suitable pharmaceutically acceptable salts include pharmaceutically acceptable metal salts, for example pharmaceutically acceptable alkali-metal or alkaline-earth-metal salts such as sodium, potassium, calcium or magnesium salts; in particular pharmaceutically acceptable metal salts of one or more carboxylic acid moieties that may be present in the compound of formula (I).

Other non-pharmaceutically acceptable salts, eg. oxalates, may be used, for example in the isolation of compounds of the invention, and are included within the scope of this invention.

The invention includes within its scope all possible stoichiometric and non-stoichiometric forms of the salts of the compounds of formula (I).

Also included within the scope of the invention are all solvates, hydrates and complexes of compounds and salts of the invention.

Certain groups, substituents, compounds or salts included in the present invention may be present as isomers. The present invention includes within its scope all such isomers, including racemates, enantiomers and mixtures thereof.

In the compounds or salts, pharmaceutical compositions, uses, methods of treatment/prophylaxis, methods of preparing, etc. according to the present invention, where a defined isomeric configuration e.g. stereochemical configuration is described or claimed, the invention includes a mixture comprising (a) a major component of the compound or salt which is in the described or claimed configuration, together with (b) one or more minor components of the compound or salt which is/are not in the described or claimed configuration. Preferably, in such a mixture, the major component of the compound or salt which is in the described or claimed configuration represents 70% or more, or 75% or more, more preferably 85% or more, still more preferably 90% or more, yet more preferably 95% or more, yet more preferably 98% or more, of the total amount of compound or salt present in the mixture on a molarity basis.

The percentage of one isomeric/stereochemical component in a mixture of different isomeric/stereochemical components, and if appropriate enantiomeric and/or diastereomeric excesses, can be measured using techniques known in the art. Such methods include the following:

(1) Measurement using NMR (e.g. $^1$H NMR) spectroscopy in the presence of chiral agent. One can measure a nuclear magnetic resonance (NMR) spectrum (preferably a $^1$H NMR spectrum, and/or a solution-phase NMR spectrum e.g. in CDCl$_3$ or D6-DMSO solvent) of the compound/salt mixture in the presence of a suitable chiral agent which "splits" the NMR peaks of a given atom in different isomers into different peak positions. The chiral agent can be: i) an optically pure reagent which reacts with the compound/salt e.g. to form a mixture of diastereomers, ii) a chiral solvent, iii) a chiral molecule which forms a transient species (e.g. diastereomeric species) with the compound/salt, or iv) a chiral shift reagent. See e.g. J. March, "Advanced Organic Chemistry", 4th edn., 1992, pages 125-126 and refs. 138-146 cited therein. A chiral shift reagent can be a chiral lanthanide shift reagent such as tris[3-trifluoroacetyl-d-camphorato]europium-(III) or others as described in Morrill, "Lanthanide Shift Reagents in Stereochemical Analysis", VCH, New York, 1986. Whatever the chiral agent is that is used, usually, the relative integrals (intensities) for the NMR peaks of a given atom or group in different isomers can provide a measurement of the relative amounts of each isomer present.

(2) Measurement using chiral chromatography, especially on an analytical scale. A suitable chiral column which separates the different isomeric components can be used to effect separation, e.g. using gas or liquid chromatography such as HPLC, and/or e.g. on an analytical scale. The peaks for each isomer can be integrated (area under each peak); and a comparison or ratio of the integrals for the different isomers present can give a measurement of the percentage of each isomeric component present. See for example: "Chiral Chromatography", Separation Science Series Author: T. E. Beesley and R. P. W. Scott, John Wiley & Sons, Ltd., Chichester, UK, 1998, electronic Book ISBN: 0585352690, Book ISBN: 0471974277.

(3) Separation of pre-existing diastereomeric mixtures which are compounds/salts of the invention can be achieved (usually directly, without derivatisation) using separation techniques such as gas or liquid chromatography. Diastereomeric ratios and/or excesses can thereby be derived e.g. from the relative peak areas or relative separated masses.

(4) Conversion with a chiral/optically-active agent and subsequent separation of the resulting isomers, e.g. diastereomers. Conversion can be via derivatisation of a derivatisable group (e.g. —OH, —NHR) on the compound/salt with an optically-active derivatising group (e.g. optically active acid chloride or acid anhydride); or can be via formation of an acid or base addition salt of the compound by treatment of the compound with an optically-active acid or base, such as + or − di-para-toluoyl tartaric acid. After derivatisation, separation of the resulting isomers e.g. diastereomers, can be using gas or liquid chromatography (usually non-chiral); or (especially with isomeric salts) can be by selective crystallisation of a single isomeric e.g. diastereoisomeric salt. Determination of isomeric ratios and/or excesses can be using chromatography peak areas or measurement of mass of each separated isomer.

See e.g. J. March, "Advanced Organic Chemistry", 4th edn., 1992, pages 120-121 and 126, and refs. 105-115 and 147-149 cited therein.

(5) Measurement of optical activity [alpha] of mixture and comparison with optical activity of pure isomer [alpha]$_{max}$ if available (e.g. see J. March, "Advanced Organic Chemistry", 4th edn., 1992, page 125 and refs. 138-139 cited therein). This assumes a substantially linear relationship between [alpha] and concentration.

Certain of the groups, e.g. heteroaromatic ring systems, included in compounds of formula (I) or their salts may exist in one or more tautomeric forms. The present invention includes within its scope all such tautomeric forms, including mixtures.

Especially when intended for oral medicinal use, the compound of formula (I) can optionally have a molecular weight of 1000 or less, for example 800 or less, in particular 650 or less or 600 or less. Molecular weight here refers to that of the unsolvated "free base" compound, that is excluding any molecular weight contributed by any addition salts, solvent (e.g. water) molecules, etc.

Synthetic Process Routes

The following processes can be used to make the compounds of the invention:

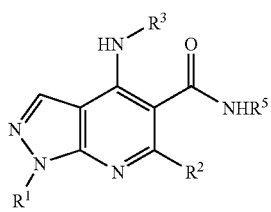

Most of the following synthetic processes following are exemplified for compounds of Formula (I) wherein $R^2$ is a hydrogen atom (H). However, some or all of these processes can also be used with appropriate modification, e.g. of starting materials and reagents, for making compounds of Formula (I) wherein $R^2$ is other than H.

Process A

Compounds of formula (I) where $X=OR^{5a}$, can be prepared according to a method, for example as described by Yu et. al. in *J. Med. Chem.*, 2001, 44, 1025-1027, by reaction of a compound of formula (II) with an amine of formula $R^3NH_2$. The reaction is preferably carried out in the presence of a base such as triethylamine or N,N-diisopropylethylamine, and/or in an organic solvent such as ethanol, dioxane or acetonitrile. The reaction may require heating e.g. to ca. 60-100° C., for example ca. 80-90° C.:

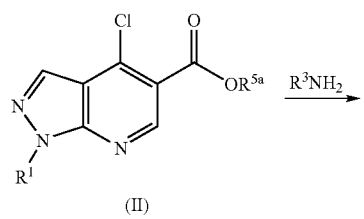

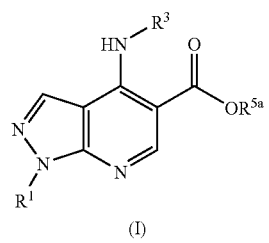

Compounds of formula (II) are also described in the above reference and can be prepared by reaction of a compound of formula (III) with, for example, diethylethoxymethylene malonate (where $R^{5a}$=Et) with heating, followed by reaction with phosphorous oxychloride, again with heating:

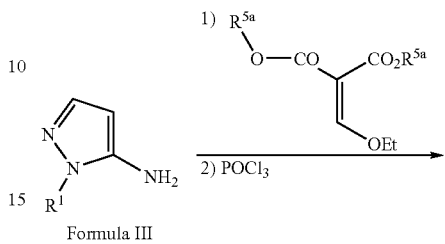

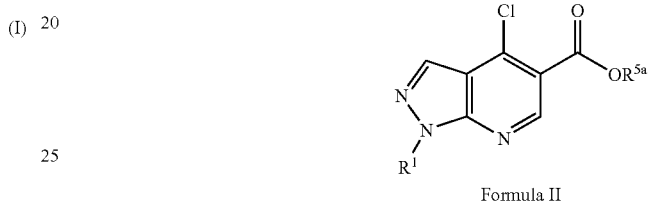

Where the desired amino pyrazole of formula (III) is not commercially available, preparation can be achieved using methods described by Dorgan et. al. in J. Chem. Soc., Perkin Trans. 1, (4), 938-42; 1980, by reaction of cyanoethylhydrazine with a suitable aldehyde of formula $R^{40}$CHO in a solvent such as ethanol, with heating, followed by reduction with, for example sodium in a solvent such as t-butanol. $R^{40}$ should be chosen so as to contain one less carbon atom than $R^1$, for example $R^{40}$=methyl will afford $R^1$=ethyl.

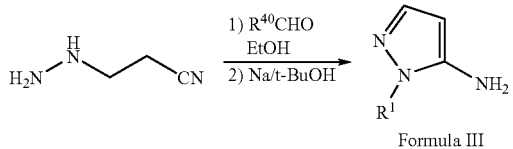

In an alternative embodiment of Process A, the 4-chloro substituent in the compound of formula (II) can be replaced by a halogen atom, such as a bromine atom or preferably a chlorine atom, in a compound of formula (IIA) as defined below. In this embodiment of Process A, the compound of formula (IIA) is reacted with the amine of formula $R^3NH_2$.

Process B

Compounds of formula (I) where $X=NHR^5$, can be prepared by reaction of a compound of formula (IV) with an amine of formula $R^3NH_2$. The reaction is preferably carried out in the presence of a base, such as triethylamine or N,N-diisopropylethylamine, and/or in an organic solvent such as ethanol, THF, dioxane or acetonitrile. The reaction may require heating, e.g. to ca. 60-100° C. or ca. 80-90° C., for example for 8-48 or 12-24 hours:

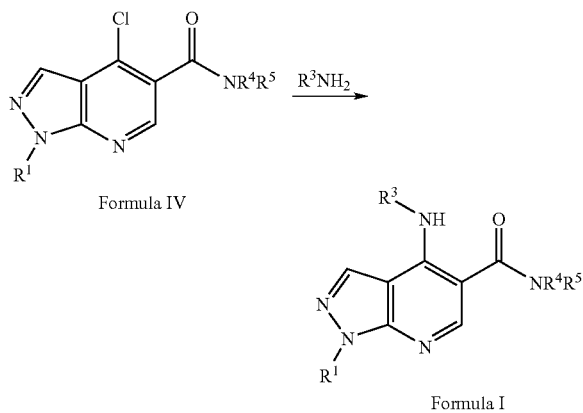

Compounds of formula (IV) can be prepared in a two step procedure as described by Bare et. al. in *J. Med. Chem.* 1989, 32, 2561-2573. This process involves, first, reaction of a compound of formula (V) with thionyl chloride (or another agent suitable for forming an acid chloride from a carboxylic acid), either in an organic solvent such as chloroform or THF, or as a neat solution. This reaction may require heating and the thus-formed intermediate may or may not be isolated. Step two involves reaction with an amine of formula $R^4R^5NH$, in an organic solvent such as THF or chloroform and may also involve the use of a base such as triethylamine or diisopropylethyl amine:

Compounds of formula (V) can be prepared by hydrolysis of an ester of formula (II) according to the method described by Yu et. al. in *J. Med. Chem.*, 2001, 44, 1025-1027. This procedure preferably involves reaction with a base such as sodium hydroxide or potassium hydroxide in a solvent e.g. an aqueous solvent such as aqueous ethanol or aqueous dioxane:

In an alternative embodiment of Process B, the 4-chloro substituent in the compound of formula (IV) can be replaced by a halogen atom, such as a bromine atom or preferably a chlorine atom, in a compound of formula (IVA) as defined below. In this embodiment of Process B, the compound of formula (IVA) is reacted with the amine of formula $R^3NH_2$.

Process C

Compounds of formula (I) can also be prepared according to a method, for example as described by Bare et. al. in *J. Med. Chem.* 1989, 32, 2561-2573, which involves reaction of a compound of formula (VI), in which —O—$R^{35}$ is a leaving group displaceable by an amine, with an amine of formula $R^3NH_2$. The —O—$R^{35}$ leaving group can be —O—$C_{1-4}$alkyl (in particular —O-Et) or —O—$S(O)_2$—$R^{37}$, wherein $R^{37}$ is $C_{1-8}$alkyl (e.g. $C_{1-4}$alkyl or $C_{1-2}$alkyl such as methyl), $C_{1-6}$fluoroalkyl (e.g. $C_{1-4}$fluoroalkyl or $C_{1-2}$fluoroalkyl such as $CF_3$ or $C_4F_9$), or phenyl wherein the phenyl is optionally substituted by one or two of independently $C_{1-2}$alkyl, halogen or $C_{1-2}$alkoxy (such as phenyl or 4-methyl-phenyl). The reaction may be carried out with or without solvent and may require heating:

Compounds of formula (VI) (also described in the above reference) can be prepared by reaction of a compound of formula (VII) with a suitable alkylating agent of formula $R^1$—X, where X is a leaving group such as halogen. The reaction is preferably carried out in the presence of a base such as potassium carbonate, in an anhydrous solvent such as DMF:

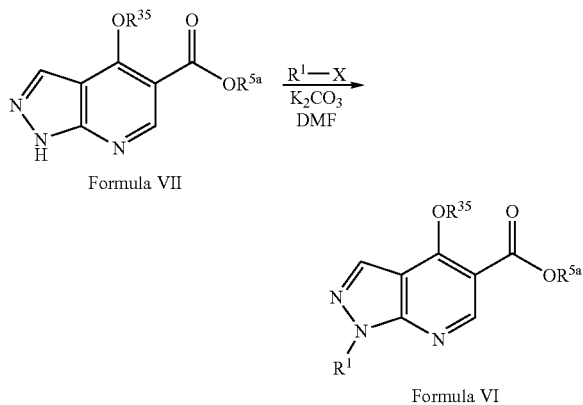

Formula VII

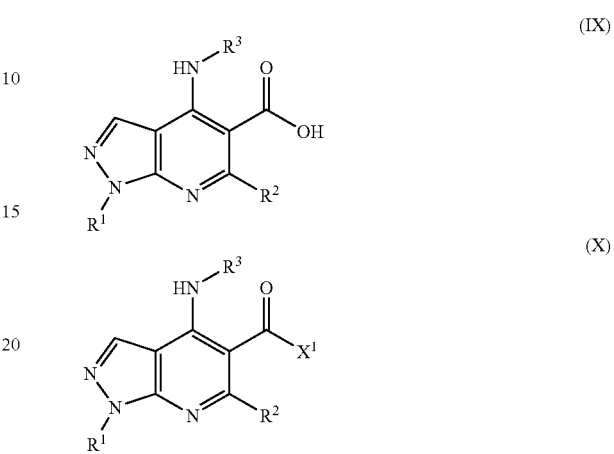

(IX)

(X)

The preparation of compounds of formula VII, e.g. where $OR^{35}$ is OEt, by oxidative cleavage of compounds of formula VIII is described by Bare et. al. in *J. Med. Chem.* 1989, 32, 2561-2573 (further referred to Zuleski et. al. in *J. Drug. Metab. Dispos.*, 1985, 13, 139).

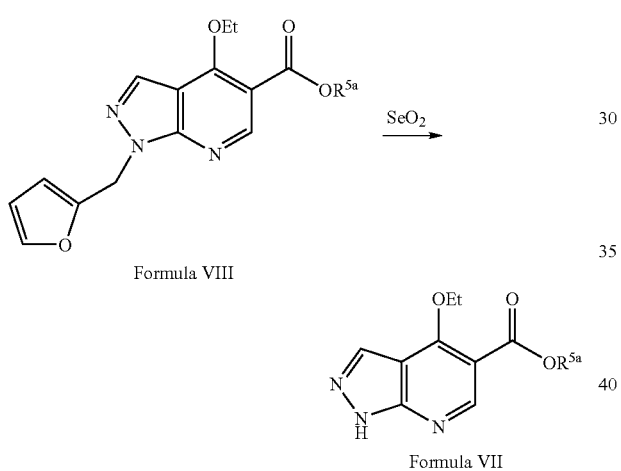

Formula VIII

Formula VII

In another embodiment of Process C, the compound of formula (VI) can be replaced by a compound of formula (VIA), wherein X is $NHR^5$ or $OR^{5a}$ as defined herein:

(VIA)

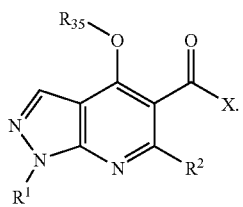

In this embodiment of Process C, the compound of formula (VIA) is reacted with the amine of formula $R^3NH_2$.

Process D

To form a compound of formula (I) wherein $X=NHR^5$, a compound of formula (I) but wherein $X=OH$ (a carboxylic acid, the compound of formula (IX) as defined below) can be converted into an activated compound of formula (I) but wherein $X=$ a leaving group $X^1$ substitutable by an amine (a compound of formula (X) as defined below, wherein $X^1$ is a leaving group substitutable by an amine); and subsequently the activated compound can be reacted with an amine of formula $R^4R^5NH$:

For example, the activated compound (the compound of formula (X)) can be the acid chloride i.e. an activated compound of formula (I) but wherein the leaving group $X^1=Cl$. This can be formed from the carboxylic acid ($X=OH$, the compound of formula (IX)) e.g. by reaction with thionyl chloride, either in an organic solvent such as chloroform or without solvent. See for example Examples 81-85. Alternatively, the activated compound (the compound of formula (X)) can be an activated ester wherein the leaving group $X^1$ is

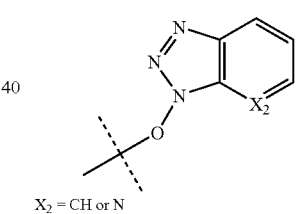

$X_2 = CH$ or $N$

The latter activated compound of formula (X) can be formed from the carboxylic acid ($X=OH$, the compound of formula (IX)) either:

(a) by reaction of the carboxylic acid with a carbodiimide such as EDC, which is 1-ethyl-3-(3'-dimethylaminopropyl) carbodiimide and is also 1-(3-dimethylaminopropyl)-3-ethylcarbodiimide, or a salt thereof e.g. hydrochloride salt, preferably followed by reaction of the resulting product with 1-hydroxybenzotriazole (HOBT); reaction (a) usually being carried out in the presence of a solvent (preferably anhydrous) such as dimethyl formamide (DMF) or acetonitrile and/or preferably under anhydrous conditions and/or usually at room temperature (e.g. about 20 to about 25° C.); or (b) by reaction with 2-(1H-benzotriazole-1-yl)-1,1,3,3-tetramethyluronium tetrafluoroborate (TBTU) or O-(7-Azabenzotriazol-1-yl)-N,N,N',N'-tetramethyluronium hexafluorophosphate (HATU), in the presence of a base such as diisopropylethylamine ($^iPr_2NEt=DIPEA$), and usually in the presence of a solvent such as dimethyl formamide (DMF) or acetonitrile and/or preferably under anhydrous conditions and/or usually at room temperature (e.g. about 20 to about 25° C.).

The carboxylic acid wherein X=OH (the compound of formula (IX) below) is usually prepared by hydrolysis of the corresponding ester of formula (I) wherein X is $OR^{5a}$. This ester can itself be prepared by any of Processes A, C, E or F as described herein.

Process D1

This is the same as Process D, but involves reaction of the activated compound of formula (X), wherein $X^1$=a leaving group substitutable by an amine (for example a leaving group as defined herein), with an amine of formula $R^4R^5NH$.

Process E

Compounds of formula (I) can be prepared by reaction of a compound of formula (XI) with an alkylating agent of formula $R^1—X^3$, where $X^3$ is a leaving group displaceable by the 1-position pyrazolopyridine nitrogen atom of the compound of formula (XI):

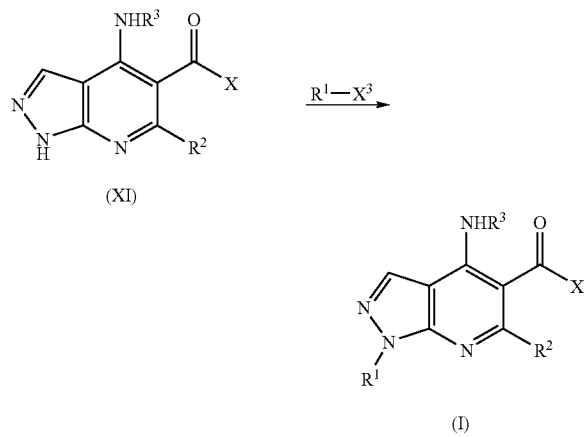

A suitable alkylating agent of formula $R^1—X^3$ can be used. For example, $X^3$ can be a halogen atom such as a chlorine atom or more preferably a bromine or iodine atom, or $X^3$ can be $—O—S(O)_2—R^{36}$ wherein $R^{36}$ is $C_{1-8}$alkyl (e.g. $C_{1-4}$alkyl or $C_{1-2}$alkyl such as methyl), $C_{1-6}$fluoroalkyl (e.g. $C_{1-4}$fluoroalkyl or $C_{1-2}$fluoroalkyl such as $CF_3$ or $C_4F_9$), or phenyl wherein the phenyl is optionally substituted by one or two of independently $C_{1-2}$alkyl, halogen or $C_{1-2}$alkoxy (such as phenyl or 4-methyl-phenyl). The reaction is preferably carried out in the presence of a base; the base can for example comprise or be potassium carbonate, sodium carbonate, sodium hydride, potassium hydride, or a basic resin or polymer such as polymer-bound 2-tert-butylimino-2-diethylamino-1,3-dimethyl-perhydro-1,3,2-diazaphosphorine. The reaction is preferably carried out in the presence of a solvent, e.g. an organic solvent such as DMF; the solvent is preferably anhydrous. Examples of alkylation Process E include Examples 183, 185, 186 and 354.

For preferable methods of making compounds of formula (XI), see for example (Reference) Examples 19-20, and Intermediates 48 and 54A.

Process F: Conversion of One Compound of Formula (I) or Salt Thereof into Another Compound of Formula (I) or Salt Thereof One compound of formula (I) or salt thereof can be converted into another compound of formula (I) or salt thereof.

This conversion preferably comprises or is one or more of the following processes F1 to F10:

F1. An oxidation process. For example, the oxidation process can comprise or be oxidation of an alcohol to a ketone (e.g. using Jones reagent, e.g. see Example 205) or oxidation of an alcohol or a ketone to a carboxylic acid. The oxidation process can e.g. comprise or be conversion of a nitrogen-containing compound of formula (I) or salt thereof to the corresponding N-oxide (e.g. using meta-chloroperoxybenzoic acid), for example conversion of a pyridine-containing compound to the corresponding pyridine N-oxide (e.g. see Examples 210-212 of PCT/EP03/11814).

F2. A reduction process, for example reduction of a ketone or a carboxylic acid to an alcohol.

F3. Acylation, for example acylation of an amine (e.g. see Examples 329-349, Example 353 of PCT/EP03/11814) or hydroxy group.

F4. Alkylation, for example alkylation of an amine or of a hydroxy group.

F5. Hydrolysis, e.g. hydrolysis of an ester to the corresponding carboxylic acid or salt thereof (e.g. see Examples 351, 488, 489, 650, 651 of PCT/EP03/11814).

F6. Deprotection, e.g. deprotection (e.g. deacylation or t-butyloxycarbonyl (BOC) removal) of an amine group (e.g. see Examples 320, (321), and (352) of PCT/EP03/11814).

F7. Formation of an ester or amide, for example from the corresponding carboxylic acid.

F8. Conversion of a ketone into the corresponding oxime (e.g. see Examples 652, 653, 654 and 680-686 of PCT/EP03/11814).

F9. Sulfonylation, e.g. sulfonamide formation by reaction of an amine with a sulfonyl halide e.g. a sulfonyl chloride (e.g. see Examples 322-328 of PCT/EP03/11814).

and/or

F10. Beckmann rearrangement of one compound of formula (I) into another compound of formula (I), preferably using cyanuric chloride (2,4,6-trichloro-1,3,5-triazine) together with a formamide such as DMF, e.g. at room temperature (see L. D. Luca, *J. Org. Chem.*, 2002, 67, 6272-6274). The Beckmann rearrangement can for example comprise conversion of a compound of formula (I) wherein $NHR^3$ is of sub-formula (o2)

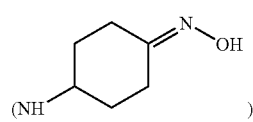

into a compound of formula (I) wherein $NHR^3$ is of sub-formula (m3)

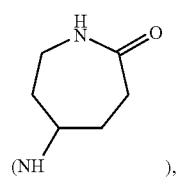

e.g. as illustrated in Examples 658 and 659 of PCT/EP03/11814, incorporated herein by reference.

An alternative process G is as follows:

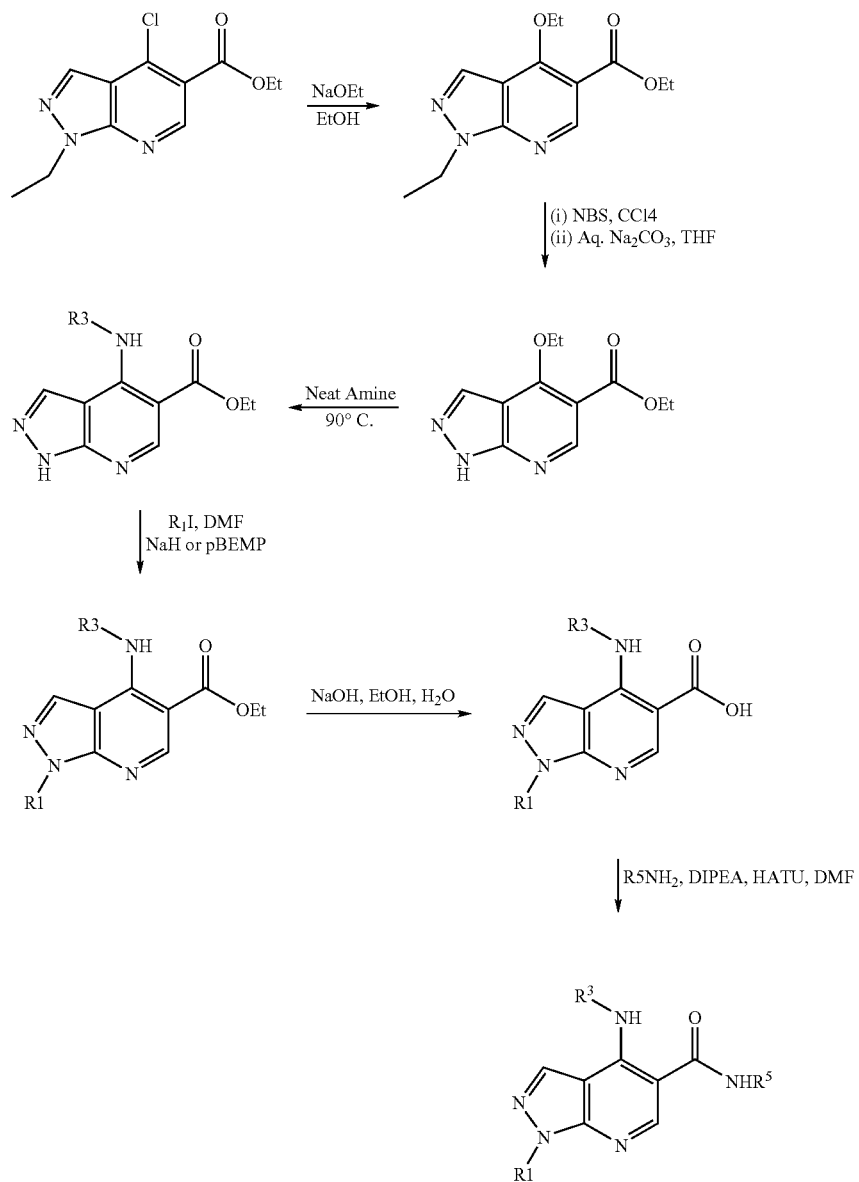

The present invention therefore also provides a method of preparing a compound of formula (I) or a salt thereof:

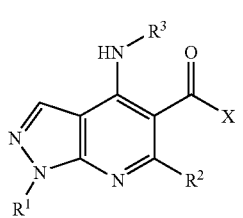
(I)

wherein $R^1$, $R^2$ and $R^3$ are as defined herein and X is $NHR^5$ or $OR^{5a}$ as defined herein, the method comprising:

(a) for a compound of formula (I) wherein $X=OR^{5a}$, reaction of a compound of formula (IIA):

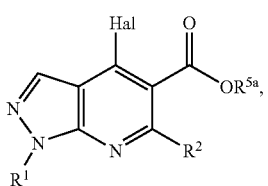
(IIA)

wherein Hal is a halogen atom (such as a bromine atom or preferably a chlorine atom), with an amine of formula $R^3NH_2$, or (b) for a compound of formula (I) wherein X=NHR⁵, reaction of a compound of formula (IVA):

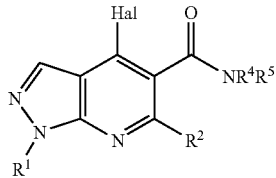

wherein Hal is a halogen atom (such as a bromine atom or preferably a chlorine atom), with an amine of formula R³NH₂, or (c) reaction of a compound of formula (VIA):

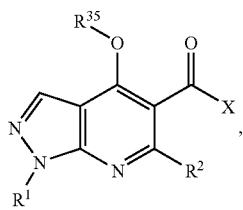

in which —O—R³⁵ is a leaving group displaceable by an amine (such as —O—C₁₋₄alkyl or —O—S(O)₂—R³⁷), with an amine of formula R³NH₂; or (d) to form a compound of formula (I) wherein X=NHR⁵, conversion of a compound of formula (IX) into an activated compound of formula (X) wherein X¹=a leaving group substitutable by an amine:

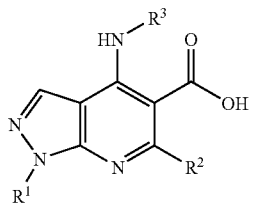

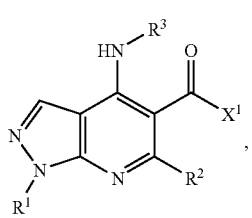

and subsequent reaction of the activated compound of formula (X) with an amine of formula R⁴R⁵NH; or (d1) to form a compound of formula (I) wherein X=NHR⁵, reaction of an activated compound of formula (X) as defined above with an amine of formula R⁴NH₂; or (e) reaction of a compound of formula (XI):

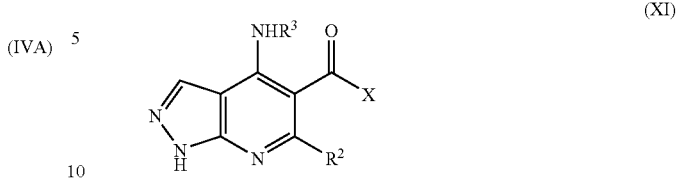

with an alkylating agent of formula R¹—X², where X² is a leaving group displaceable by the 1-position pyrazolopyridine nitrogen atom of the compound of formula (XI); or (f) conversion of one compound of formula (I) or salt thereof into another compound of formula (I) or salt thereof;

and optionally converting the compound of formula (I) into a salt thereof e.g. a pharmaceutically acceptable salt thereof.

In methods (d) and/or (d1), the activated compound of formula (X) wherein X¹=a leaving group substitutable by an amine can be the acid chloride i.e. an activated compound of formula (X) wherein X¹=Cl. Alternatively, the activated compound of formula (X) can be an activated ester wherein the leaving group X¹ is

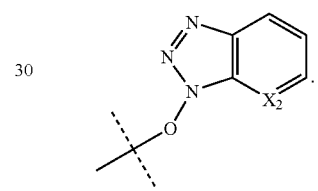

X₂ = CH or N

Preferred features of methods (a), (b), (c), (d), (d1) and (e), independently of each other, are as described above for Processes A, B, C, D, D1 and E, with all necessary changes being made.

The present invention also provides: (g) a method of preparing a pharmaceutically acceptable salt of a compound of formula (I) comprising conversion of the compound of formula (I) or a salt thereof into the desired pharmaceutically acceptable salt thereof. (See for example Examples 490, 491, 518A, 593).

The present invention also provides a compound of formula (I) or a salt thereof, prepared by a method as defined herein.

Medical Uses

The present invention also provides a compound of formula (I) or a pharmaceutically acceptable salt thereof for use as an active therapeutic substance in a mammal such as a human. The compound or salt can be for use in the treatment and/or prophylaxis of any of the diseases/conditions described herein (e.g. for use in the treatment and/or prophylaxis of an inflammatory and/or allergic disease in a mammal) and/or for use as a phosphodiesterase inhibitor e.g. for use as a phosphodiesterase 4 (PDE4) inhibitor. "Therapy" may include treatment and/or prophylaxis.

Also provided is the use of a compound of formula (I) or a pharmaceutically acceptable salt thereof in the manufacture of a medicament (e.g. pharmaceutical composition) for the treatment and/or prophylaxis of any of the diseases/conditions described herein in a mammal such as a human, e.g. for the treatment and/or prophylaxis of an inflammatory and/or allergic disease in a mammal such as a human.

Also provided is a method of treatment and/or prophylaxis of any of the diseases/conditions described herein in a mammal (e.g. human) in need thereof, e.g. a method of treatment and/or prophylaxis of an inflammatory and/or allergic disease in a mammal (e.g. human) in need thereof, which method comprises administering to the mammal (e.g. human) a therapeutically effective amount of a compound of formula (I) as herein defined or a pharmaceutically acceptable salt thereof.

Phosphodiesterase 4 inhibitors are thought to be useful in the treatment and/or prophylaxis of a variety of diseases/conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain. Ulcerative colitis and/or Crohn's disease are collectively often referred to as inflammatory bowel disease.

In the treatment and/or prophylaxis, the inflammatory and/or allergic disease is preferably chronic obstructive pulmonary disease (COPD), asthma, rheumatoid arthritis or allergic rhinitis in a mammal (e.g. human). More preferably, the treatment and/or prophylaxis is of COPD or asthma in a mammal (e.g. human).

PDE4 inhibitors are thought to be effective in the treatment of asthma (e.g. see M. A. Giembycz, *Drugs*, February 2000, 59(2), 193-212; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; and references cited in the aforementioned publications).

PDE4 inhibitors are thought to be effective in the treatment of COPD. For example, see S. L. Wolda, *Emerging Drugs*, 2000, 5(3), 309-319; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; and references cited in the aforementioned publications; and G. Krishna et al., *Expert Opinion on Investigational Drugs*, 2004, 13(3), 255-267 (see especially pp. 259-261 and refs. 102-111 and 201 therein). COPD is often characterised by the presence of airflow obstruction due to chronic bronchitis and/or emphysema (e.g., see S. L. Wolda, *Emerging Drugs*, 2000, 5(3), 309-319).

PDE4 inhibitors are thought to be effective in the treatment of allergic rhinitis (e.g. see B. M. Schmidt et al., *J Allergy & Clinical Immunology*, 108(4), 2001, 530-536).

PDE4 inhibitors are thought to be effective in the treatment of rheumatoid arthritis and multiple sclerosis (e.g. see H. J. Dyke et al., *Expert Opinion on Investigational Drugs*, January 2002, 11(1), 1-13; C. Burnouf et al., *Current Pharmaceutical Design*, 2002, 8(14), 1255-1296; and A. M. Doherty, *Current Opinion Chem. Biol.*, 1999, 3(4), 466-473; and references cited in these publications). See e.g. A. M. Doherty, *Current Opinion Chem. Biol.*, 1999, 3(4), 466-473 and references cited therein for atopic dermatitis use.

PDE4 inhibitors have been suggested as having analgesic properties and thus being effective in the treatment of pain (A. Kumar et al., *Indian J. Exp. Biol.*, 2000, 38(1), 26-30).

In the invention, the treatment and/or prophylaxis can be of cognitive impairment e.g. cognitive impairment in a neurological disorder such as Alzheimer's disease. For example, the treatment and/or prophylaxis can comprise cognitive enhancement e.g. in a neurological disorder. See for example: H. T. Zhang et al. in: *Psychopharmacology*, June 2000, 150 (3), 311-316 and *Neuropsychopharmacology*, 2000, 23(2), 198-204; and T. Egawa et al., *Japanese J. Pharmacol.*, 1997, 75(3), 275-81.

PDE4 inhibitors such as rolipram have been suggested as having antidepressant properties (e.g. J. Zhu et al., *CNS Drug Reviews*, 2001, 7(4), 387-398; O'Donnell, *Expert Opinion on Investigational Drugs*, 2000, 9(3), 621-625; and H. T. Zhang et al., *Neuropsychopharmacology*, October 2002, 27(4), 587-595).

Pharmaceutical Compositions and Dosing

For use in medicine, the compounds of the present invention are usually administered as a pharmaceutical composition.

The present invention therefore provides in a further aspect a pharmaceutical composition comprising a compound of formula (I) or a pharmaceutically acceptable salt thereof and one or more pharmaceutically acceptable carriers and/or excipients.

The pharmaceutical composition can be for use in the treatment and/or prophylaxis of any of the conditions described herein.

The invention also provides a method of preparing a pharmaceutical composition comprising a compound of formula (I), as herein defined, or a pharmaceutically acceptable salt thereof, and one or more pharmaceutically acceptable carriers and/or excipients, the method comprising mixing the compound or salt with the one or more pharmaceutically acceptable carriers and/or excipients.

The invention also provides a pharmaceutical composition prepared by said method.

The compounds of formula (I) and/or the pharmaceutical composition may be administered, for example, by oral, parenteral (e.g. intravenous, subcutaneous, or intramuscular), inhaled or nasal administration. Accordingly, the pharmaceutical composition is preferably suitable for oral, parenteral (e.g. intravenous, subcutaneous, or intramuscular), inhaled or nasal administration. More preferably, the pharmaceutical composition is suitable for inhaled or oral administration, e.g. to a mammal such as a human. Inhaled administration involves topical administration to the lung e.g. by aerosol or dry powder composition. Oral administration to a human is most preferred.

A pharmaceutical composition suitable for oral administration can be liquid or solid; for example it can be a syrup, suspension or emulsion, a tablet, a capsule or a lozenge.

A liquid formulation will generally consist of a suspension or solution of the compound or pharmaceutically acceptable salt in a suitable pharmaceutically acceptable liquid carrier(s), for example an aqueous solvent such as water, ethanol or glycerine, or a non-aqueous solvent, such as polyethylene glycol or an oil. The formulation may also contain a suspending agent, preservative, flavouring and/or colouring agent.

A pharmaceutical composition suitable for oral administration being a tablet can comprise one or more pharmaceutically acceptable carriers and/or excipients suitable for preparing tablet formulations. The carrier can for example be or include lactose, cellulose (for example microcrystalline cellulose), or mannitol. The tablet can also or instead contain one or more pharmaceutically acceptable excipients, for example a binding agent such as hydroxypropylmethylcellulose or povidone (polyvinylpyrollidone), a lubricant e.g. an alkaline earth metal stearate such as magnesium stearate, and/or a tablet disintegrant such as sodium starch glycollate, croscarmellose sodium, or crospovidone (cross-linked polyvinylpyrollidone). The pharmaceutical composition being a tablet can be prepared by a method comprising the steps of: (i) mixing the compound of formula (I), as herein defined, or a pharmaceutically acceptable salt thereof, with the one or more pharmaceutically acceptable carriers and/or excipients, (ii) compressing the resulting mixture (which is usually in powder form) into tablets, and (iii) optionally coating the tablet with a tablet film-coating material.

A pharmaceutical composition suitable for oral administration being a capsule can be prepared using encapsulation procedures. For example, pellets or powder containing the active ingredient can be prepared using a suitable pharmaceutically acceptable carrier and then filled into a hard gelatin capsule. Alternatively, a dispersion or suspension can be prepared using any suitable pharmaceutically acceptable carrier, for example an aqueous gum or an oil and the dispersion or suspension then filled into a soft gelatin capsule.

Preferably the composition is in unit dose form such as a tablet or capsule for oral administration, e.g. for oral administration to a human.

A parenteral composition can comprise a solution or suspension of the compound or pharmaceutically acceptable salt in a sterile aqueous carrier or parenterally acceptable oil. Alternatively, the solution can be lyophilised; the lyophilised parenteral pharmaceutical composition can be reconstituted with a suitable solvent just prior to administration.

Compositions for nasal or inhaled administration may conveniently be formulated as aerosols, drops, gels or dry powders.

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomizing device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted. Where the dosage form comprises an aerosol dispenser, it preferably contains a suitable propellant under pressure such as compressed air, carbon dioxide, or an organic propellant such as a chlorofluorocarbon (CFC) or hydrofluorocarbon (HFC). Suitable CFC propellants include dichlorodifluoromethane, trichlorofluoromethane and dichlorotetrafluoroethane. Suitable HFC propellants include 1,1,1,2,3,3,3-heptafluoropropane and 1,1,1,2-tetrafluoroethane. The aerosol dosage forms can also take the form of a pump-atomiser.

Particle Size Reduction of Compound of Formula (I) or Salt Thereof

For pharmaceutical compositions suitable and/or adapted for inhaled administration, it is preferred that the compound or salt of formula (I) is in a particle-size-reduced form, and more preferably the size-reduced form is obtained or obtainable by micronization. Micronisation usually involves subjecting the compound/salt to collisional and/or abrasional forces in a fast-flowing circular or spiral/vortex-shaped airstream often including a cyclone component. The preferable particle size of the size-reduced (e.g. micronised) compound or salt is defined by a D50 value of about 0.5 to about 10 microns, e.g. about 1 to about 7 microns (e.g. as measured using laser diffraction). For example, it is preferable for the compound or salt of formula (I) to have a particle size defined by: a D10 of about 0.3 to about 3 microns (e.g. about 0.5 to about 2 microns, or about 1 micron), and/or a D50 of about 0.5 to about 10 microns or about 1 to about 7 microns (e.g. about 2 to about 5 microns or about 2 to about 4 microns), and/or a D90 of about 1 to about 30 microns or about 2 to about 20 microns or about 3 to about 15 microns (e.g. about 5 to about 15 microns or about 5 to about 10 microns); for example as measured using laser diffraction.

In particle size measurements, D90, D50 and D10 respectively mean that 90%, 50% and 10% of the material is less than the micron size specified. D50 is the median particle size. DV90, DV50 and DV10 respectively mean that 90%, 50% and 10% by volume of the material is less than the micron size specified. DM90, DM50 and DM10 respectively mean that 90%, 50% and 10% by weight of the material is less than the micron size specified.

Laser diffraction measurement of particle size can use a dry method (wherein a suspension of the compound/salt in an airflow crosses the laser beam) or a wet method [wherein a suspension of the compound/salt in a liquid dispersing medium, such as isooctane or (e.g. if compound is soluble in isooctane) 0.1% Tween 80 in water, crosses the laser beam]. With laser diffraction, particle size is preferably calculated using the Fraunhofer calculation; and/or preferably a Malvern Mastersizer or Sympatec apparatus is used for measurement. For example, particle size measurement and/or analysis by laser diffraction can use any or all of (preferably all of) the following: a Malvern Mastersizer longbed version, a dispersing medium of 0.1% Tween 80 in water, a stir rate of ca. 1500 rpm, ca. 3 mins sonification prior to final dispersion and analysis, a 300 RF (Reverse Fourier) lens, and/or the Fraunhofer calculation with Malvern software.

An illustrative non-limiting example of a small-scale micronization process is now given:

Micronisation Example

Purpose: To micronize a compound of formula (I) or salt thereof, usually in an amount of approximately 600-1000 mg thereof, using a Jetpharma MC1 micronizer.

The parent (unmicronised) and micronised materials are analyzed for particle size by laser diffraction and crystallinity by PXRD.

Equipment and Material

| Equipment/material | Description and specification |
|---|---|
| Jetpharma MC1 Micronizer | Nitrogen supply: Air tank with 275 psi rate tubing |
| Analytical balance | Sartorius Analytical |
| Top loader balance | Mettler PM400 |
| Digital Caliper | VWR Electronic caliper |
| Vibrational spatula | Auto-spat Dispenser |
| Materials to be micronised | a compound of formula (I) or salt thereof |

The Jetpharma MC1 Micronizer comprises a horizontal disc-shaped milling housing having: a tubular compound inlet (e.g. angled at ca. 30 degrees to the horizontal) for entry of a suspension of unmicronised compound of formula (I) or salt in a gasflow, a separate gas inlet for entry of gases, a gas outlet for exit of gases, and a collection vessel for collecting micronised material. The milling housing has two chambers: (a) an outer annular chamber in gaseous connection with the gas inlet, the chamber being for receiving pressurised gas (e.g. air or nitrogen), and (b) a disc-shaped inner milling chamber within and coaxial with the outer chamber for micronising the input compound/salt, the two chambers being separated by an annular wall. The annular wall (ring R) has a plurality of narrow-bored holes connecting the inner and outer chambers and circumferentially-spaced-apart around the annular wall. The holes opening into the inner chamber are directed at an angle (directed part-way between radially and tangentially), and in use act as nozzles directing pressurised gas at high velocity from the outer chamber into the inner chamber and in an inwardly-spiral path (vortex) around the inner chamber (cyclone). The compound inlet is in gaseous communication with the inner chamber via a nozzle directed tangentially to the inner chamber, within and near to the annular wall/ring R. Upper and lower broad-diameter exit vents in the central axis of the inner milling chamber connect to (a) (lower exit) the collection vessel which has no air outlet, and (b) (upper exit) the gas outlet which leads to a collection bag, filter and a gas exhaust. Inside and coaxial with the tubular compound inlet and longitudinally-movable within it is positioned a venturi inlet (V) for entry of gases. The compound inlet also has a bifurcation connecting to an upwardly-directed material inlet port for inputting material.

In use, the narrow head of the venturi inlet (V) is preferably positioned below and slightly forward of the material inlet port so that when the venturi delivers pressurised gas (e.g. air or nitrogen) the feed material is sucked from the material inlet port into the gasstream thorough the compound inlet and is accelerated into the inner milling chamber tangentially at a subsonic speed. Inside the milling chamber the material is further accelerated to a supersonic speed by the hole/nozzle system around the ring (R) (annular wall) of the milling chamber. The nozzles are slightly angled so that the acceleration pattern of the material is in the form of an inwardly-directed vortex or cyclone. The material inside the milling chamber circulates rapidly and particle collisions occur during the process, causing larger particles to fracture into smaller ones. "Centrifugal" acceleration in the vortex causes the larger particles to remain at the periphery of the inner chamber while progressively smaller particles move closer to the center until they exit the milling chamber, generally through the lower exit, at low pressure and low velocity. The particles that exit the milling chamber are heavier than air and settle downward through the lower exit into the collection vessel, while the exhaust gas rises (together with a minority of small particles of micronised material) and escapes into the atmosphere at low pressure and low velocity.

Procedure:

The micronizer is assembled. The venturi protrusion distance from input port is preferably adjusted to about 1.0 cm respectively (e.g. so that the narrow head of the venturi inlet is positioned below and slightly forward of the material inlet port) and is measured with a micro-caliper to make sure that it is inserted correctly. The ring (R) and venturi (V) pressures are adjusted according to the values specified in the experimental design (refer to experimental section below) by adjusting the valves on the pressure gauges on the micronizer. The setup is checked for leakage by observing if there is any fluctuation in the reading of the pressure gauges.

Note that the venturi (V) pressure is kept at least 2 bars greater than the ring (R) pressure to prevent regurgitation of material, e.g. outwardly from the material inlet port.

Balance performance is checked with calibration weights. Specified amount of the parent material (see section on experimental run) is weighed into a plastic weigh boat. The material is then fed into the micronizer using a vibrational spatula (e.g. V-shaped in cross-section) at a specified feed rate. The material feeding time and equipment pressures are monitored during the micronization process.

Upon completion of the micronising run, the nitrogen supply is shut off and the collection bag is tapped to allow particles to settle into the recovery/collection vessel at the bottom of the micronizer. The collection bag is removed and set aside. The micronised powder in the recovery vessel (collection vessel) and the cyclone (above the recovery vessel) are collected separately into different weighed+labelled collection vials. The weight of the micronised material is recorded. The micronizer is disassembled and residual PDE4 compound on the micronizer inner surface is rinsed with 70/30 isopropyl alcohol/water and collected into a flask. The micronizer is then thoroughly cleaned by rinsing and wiping with suitable solvent and dried before subsequent runs are performed.

Optional Experimental Parameters

Parent (unmicronised) material (Procedure 1): a compound of formula (I) or salt thereof Balance(s) Used: Sartorius analytical

| Procedure no. | Material input amount (g) | Venturi Pressure (V)/ring (R) Pressure (bar) | Intended feed-rate | Time needed to feed material (min + sec) | Actual feed-rate (g/min) |
|---|---|---|---|---|---|
| 1 | ca. 0.9 g | V = 8 to 10 bar<br>R = 5.5 to 6 bar | 180 to 200 mg/min | | procedure not carried out |

The above optional parameters can be varied using the skilled person's knowledge.

Results and/or Observations

% yield=[(Material from vessel+Material from cyclone)/Material input amount]×100 In general, very approximately 50-75% yields are achievable using this method, including material from collection vessel and material from inside walls of cyclone.

Procedure 1 includes possible parameters and conditions and has not been carried out.

Dry Powder Inhalable Compositions

For pharmaceutical compositions suitable and/or adapted for inhaled administration, it is preferred that the pharmaceutical composition is a dry powder inhalable composition. Such a composition can comprise a powder base such as lactose or starch, the compound of formula (I) or salt thereof (preferably in particle-size-reduced form, e.g. in micronised form), and optionally a performance modifier such as L-leucine, mannitol, trehalose and/or magnesium stearate. Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume)

of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. Most importantly, it is preferable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

In the dry powder inhalable composition, preferably, the compound of formula (I) or salt thereof is present in about 0.1% to about 70% (e.g. about 1% to about 50%, e.g. about 5% to about 40%, e.g. about 20 to about 30%) by weight of the composition.

An illustrative non-limiting example of a dry powder inhalable composition follows:

Dry Powder Formulation Example—Dry Powder Lactose Blend Preparation

Using a size-reduced e.g. micronised form of the compound of formula (I) or salt thereof (e.g. as prepared in the Micronisation Example above), the dry powder blend is prepared by mixing the required amount of the compound/salt (e.g. 10 mg, 1% w/w) with inhalation-grade lactose containing 10% fines (e.g. 990 mg, 99% w/w) in a Teflon™ (polytetrafluoroethene) pot in a Mikro-dismembrator ball-mill (but without a ball bearing) at ¾ speed (ca. 2000-2500 rpm) for about 4 hours at each blend concentration. The Mikro-dismembrator (available from B. Braun Biotech International, Schwarzenberger Weg 73-79, D-34212 Melsungen, Germany; www.bbraunbiotech.com) comprises a base with an upwardly-projecting and sidewardly-vibratable arm to which is attached the Teflon™ pot. The vibration of the arm achieves blending.

Other blends: 10% w/w compound/salt (50 mg)+90% w/w lactose (450 mg, inhalation-grade lactose containing 10% fines).

Serial dilution of the 1% w/w blend can achieve e.g. 0.1% and 0.3% w/w blends.

Dry Powder Inhalation Devices

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose, e.g. of the dry powder composition, can be administered by inhalation via a device such as the DISKUS™ device, marketed by GlaxoSmithKline. The DISKUS™ inhalation device is usually substantially as described in GB 2,242,134 A. In such device at least one container for the pharmaceutical composition in powder form (the at least one container preferably being a plurality of sealed dose containers mounted longitudinally in a strip or ribbon) is defined between two members peelably secured to one another; the device comprises: means defining an opening station for the said at least one container; means for peeling the members apart at the opening station to open the container; and an outlet, communicating with the opened container, through which a user can inhale the pharmaceutical composition in powder form from the opened container.

Unit Dose Form and Dosing Regimens

Preferably the composition is in unit dose form such as a tablet or capsule for oral administration, e.g. for oral administration to a human.

In the pharmaceutical composition, a or each dosage unit for oral or parenteral administration preferably contains from 0.01 to 3000 mg, more preferably 0.5 to 1000 mg, of a compound of the formula (I) or a pharmaceutically acceptable salt thereof, calculated as the free base. A or each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

A pharmaceutically acceptable compound or salt of the invention is preferably administered to a mammal (e.g. human) in a daily oral or parenteral dose of 0.001 mg to 50 mg per kg body weight per day (mg/kg/day), for example 0.01 to 20 mg/kg/day or 0.03 to 10 mg/kg/day or 0.1 to 2 mg/kg/day, of the compound of the formula (I) or a pharmaceutically acceptable salt thereof, calculated as the free base.

A pharmaceutically acceptable compound or salt of the invention is preferably administered to a mammal (e.g. human) in a daily nasal or inhaled dose of: 0.0001 to 5 mg/kg/day or 0.0001 to 1 mg/kg/day, e.g. 0.001 to 1 mg/kg/day or 0.001 to 0.3 mg/kg/day or 0.001 to 0.1 mg/kg/day or 0.005 to 0.3 mg/kg/day, of the compound of the formula (I) or a pharmaceutically acceptable salt thereof, calculated as the free base.

The pharmaceutically acceptable compounds or salts of the invention is preferably administered in a daily dose (for an adult patient) of, for example, an oral or parenteral dose of 0.01 mg to 3000 mg per day or 0.5 to 1000 mg per day e.g. 2 to 500 mg per day, or a nasal or inhaled dose of 0.001 to 300 mg per day or 0.001 to 50 mg per day or 0.01 to 30 mg per day or 0.01 to 5 mg per day or 0.02 to 2 mg per day, of the compound of the formula (I) or a pharmaceutically acceptable salt thereof, calculated as the free base.

Combinations

The compounds, salts and/or pharmaceutical compositions according to the invention may also be used in combination with another therapeutically active agent, for example, a β2 adrenoreceptor agonist, an anti-histamine, an anti-allergic or an anti-inflammatory agent.

The invention thus provides, in a further aspect, a combination comprising a compound of formula (I) or a pharmaceutically acceptable salt thereof together with another therapeutically active agent, for example, a $\beta_2$-adrenoreceptor agonist, an anti-histamine, an anti-allergic, an anti-inflammatory agent or an antiinfective agent.

Preferably, the $\beta_2$-adrenoreceptor agonist is salmeterol (e.g. as racemate or a single enantiomer such as the R-enantiomer), salbutamol, formoterol, salmefamol, fenoterol or terbutaline, or a salt thereof (e.g. pharmaceutically acceptable salt thereof), for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 12-24 hour period such as salmeterol or formoterol. Preferably, the $\beta_2$-adrenoreceptor agonist is for inhaled administration, e.g. once per day and/or for simultaneous inhaled administration; and more preferably the $\beta_2$-adrenoreceptor agonist is in particle-size-reduced form e.g. as defined herein. Preferably, the β₂-adrenoreceptor agonist combination is for treatment and/or prophylaxis of COPD or asthma. Salmeterol or a pharmaceutically acceptable salt thereof, e.g. salmeterol xinofoate, is preferably administered to humans at an inhaled dose of 25 to 50 micrograms twice per day (measured as the free base). The combination with a β₂-adrenoreceptor agonist can be as described in WO 00/12078.

Preferred long acting β₂-adrenoreceptor agonists include those described in WO 02/066422A, WO 03/024439, WO 02/070490 and WO 02/076933.

Especially preferred long-acting β₂-adrenoreceptor agonists include compounds of formula (XX) (described in WO 02/066422):

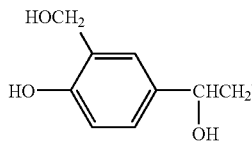 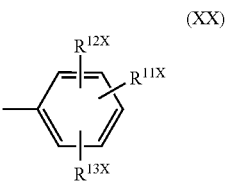

(XX)

or a salt or solvate thereof, wherein in formula (XX):

$m^X$ is an integer of from 2 to 8;

$n^X$ is an integer of from 3 to 11, with the proviso that $m^X + n^X$ is 5 to 19, $R^{11X}$ is —XSO₂NR$^{16X}$R$^{17X}$ wherein X is —(CH₂)$_{p^X}$— or C$_{2-6}$ alkenylene;

$R^{16X}$ and $R^{17X}$ are independently selected from hydrogen, C$_{1-6}$alkyl, C$_{3-7}$cycloalkyl, C(O)NR$^{18X}$R$^{19X}$, phenyl, and phenyl (C$_{1-4}$alkyl)-, or $R^{16X}$ and $R^{17X}$, together with the nitrogen to which they are bonded, form a 5-, 6-, or 7-membered nitrogen containing ring, and $R^{16X}$ and $R^{17X}$ are each optionally substituted by one or two groups selected from halo, C$_{1-6}$alkyl, C$_{1-6}$haloalkyl, C$_{1-6}$alkoxy, hydroxy-substituted C$_{1-6}$alkoxy, —CO₂R$^{18X}$, —SO₂NR$^{18X}$R$^{19X}$, —CONR$^{18X}$R$^{19X}$, —NR$^{18X}$C(O)R$^{19X}$, or a 5-, 6- or 7-membered heterocylic ring;

$R^{18X}$ and $R^{19X}$ are independently selected from hydrogen, C$_{1-6}$alkyl, C$_{3-6}$cycloalkyl, phenyl, and phenyl (C$_{1-4}$alkyl)-; and $p^X$ is an integer of from 0 to 6, preferably from 0 to 4;

$R^{12X}$ and $R^{13X}$ are independently selected from hydrogen, C$_{1-6}$alkyl, C$_{1-6}$alkoxy, halo, phenyl, and C$_{1-6}$haloalkyl; and $R^{14X}$ and $R^{15X}$ are independently selected from hydrogen and C$_{1-4}$alkyl with the proviso that the total number of carbon atoms in $R^{14X}$ and $R^{15X}$ is not more than 4.

Preferred β₂-adrenoreceptor agonists disclosed in WO 02/066422 include:

3-(4-{[6-({(2R)-2-hydroxy-2-[4-hydroxy-3-(hydroxymethyl)-phenyl]ethyl}amino)hexyl]oxy}butyl)benzenesulfonamide and 3-(3-{[7-({(2R)-2-hydroxy-2-[4-hydroxy-3-hydroxymethyl)phenyl]ethyl}-amino)heptyl]oxy}propyl)benzenesulfonamide.

A preferred β₂-adrenoreceptor agonist disclosed in WO 03/024439 is:

4-{(1R)-2-[(6-{2-[(2,6-dichlorobenzyl)oxy]ethoxy}hexyl)amino]-1-hydroxyethyl}-2-(hydroxymethyl)phenol.

A combination of a compound of formula (I) or salt together with an anti-histamine is preferably for oral administration (e.g. as a combined composition such as a combined tablet), and can be for treatment and/or prophylaxis of allergic rhinitis. Examples of anti-histamines include methapyrilene, or H1 antagonists such as cetirizine, loratadine (e.g. Clarityn™), desloratadine (e.g. Clarinex™) or fexofenadine (e.g. Allegra™).

The invention also provides, in a further aspect, a combination comprising a compound of formula (I) or a pharmaceutically acceptable salt thereof together with an anticholinergic compound, e.g. a muscarinic (M) receptor antagonist in particular an M₁, M₂, M₁/M₂, or M₃ receptor antagonist, more preferably a M₃ receptor antagonist, still more preferably a M₃ receptor antagonist which selectively antagonizes (e.g. antagonizes 10 times or more strongly) the M₃ receptor over the M₁ and/or M₂ receptor. For combinations of anticholinergic compounds/muscarinic (M) receptor antagonist with PDE4 inhibitors, see for example WO 03/011274 A2 and WO 02/069945 A2/US 2002/0193393 A1 and US 2002/052312 A1, and some or all of these publications give examples of anticholinergic compounds/muscarinic (M) receptor antagonists which may be used with the compounds of formula (I) or salts, and/or suitable pharmaceutical compositions. For example, the muscarinic receptor antagonist can comprise or be an ipratropium salt (e.g. ipratropium bromide), an oxitropium salt (e.g. oxitropium bromide), or more preferably a tiotropium salt (e.g. tiotropium bromide); see e.g. EP 418 716 A1 for tiotropium.

The anticholinergic compound or muscarinic (M) receptor antagonist, e.g. M₃ receptor antagonist, is preferably for inhaled administration, more preferably in particle-size-reduced form e.g. as defined herein. More preferably, both the muscarinic (M) receptor antagonist and the compound of formula (I) or the pharmaceutically acceptable salt thereof are for inhaled administration. Preferably, the anticholinergic compound or muscarinic receptor antagonist and the compound of formula (I) or salt are for simultaneous administration. The muscarinic receptor antagonist combination is preferably for treatment and/or prophylaxis of COPD.

Other suitable combinations include, for example, a combination comprising a compound of formula (I) or a pharmaceutically acceptable salt thereof together with another anti-inflammatory agent such as an anti-inflammatory corticosteroid; or a non-steroidal anti-inflammatory drug (NSAID) such as a leukotriene antagonist (e.g. montelukast), an iNOS inhibitor, a tryptase inhibitor, a elastase inhibitor, a beta-2 integrin antagonist, a adenosine 2a agonist, a CCR3 antagonist, or a 5-lipoxogenase inhibitor; or an antiinfective agent (e.g. an antibiotic or an antiviral). An iNOS inhibitor is preferably for oral administration. Suitable iNOS inhibitors (inducible nitric oxide synthase inhibitors) include those disclosed in WO 93/13055, WO 98/30537, WO 02/50021, WO 95/34534 and WO 99/62875. Suitable CCR3 inhibitors include those disclosed in WO 02/26722.

In a combination comprising a compound of formula (I) or a pharmaceutically acceptable salt thereof together with an anti-inflammatory corticosteroid (which is preferably for treatment and/or prophylaxis of asthma, COPD or allergic rhinitis), then preferably the anti-inflammatory corticosteroid is fluticasone, fluticasone propionate (e.g. see U.S. Pat. No. 4,335,121), beclomethasone, beclomethasone 17-propionate ester, beclomethasone 17,21-dipropionate ester, dexamethasone or an ester thereof, mometasone or an ester thereof, ciclesonide, budesonide, flunisolide, or a compound as described in WO 02/12266 A1 (e.g. as claimed in any of claims 1 to 22 therein), or a pharmaceutically acceptable salt of any of the above. If the anti-inflammatory corticosteroid is a compound as described in WO 02/12266 A1, then preferably it is Example 1 therein {which is 6α,9α-difluoro-17α-[(2-furanylcarbonyl)oxy]-11β-hydroxy-16α-methyl-3-oxo-androsta-1,4-diene-17β-carbothioic acid S-fluoromethyl ester} or Example 41 therein {which is 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester}, or a pharmaceutically acceptable salt thereof. The anti-inflammatory corticosteroid is preferably for intranasal or inhaled administration. Fluticasone propionate is preferred and is preferably for inhaled administration to a human either (a) at a dose of 250 micrograms once per day or (b) at a dose of 50 to 250 micrograms twice per day.

Also provided is a combination comprising a compound of formula (I) or a pharmaceutically acceptable salt thereof together with $\beta_2$-adrenoreceptor agonist and an anti-inflammatory corticosteroid, for example as described in WO 03/030939 A1. Preferably this combination is for treatment and/or prophylaxis of asthma, COPD or allergic rhinitis. The $\beta_2$-adrenoreceptor agonist and/or the anti-inflammatory corticosteroid can be as described above and/or as described in WO 03/030939 A1. Most preferably, in this "triple" combination, the $\beta_2$-adrenoreceptor agonist is salmeterol or a pharmaceutically acceptable salt thereof (e.g. salmeterol xinafoate) and the anti-inflammatory corticosteroid is fluticasone propionate.

The combinations referred to above may conveniently be presented for use in the form of a pharmaceutical composition and thus a pharmaceutical composition comprising a combination as defined above together with one or more pharmaceutically acceptable carriers and/or excipients represent a further aspect of the invention.

The individual compounds of such combinations may be administered either sequentially or simultaneously in separate or combined pharmaceutical composition.

In one embodiment, the combination as defined herein can be for simultaneous inhaled administration and is disposed in a combination inhalation device. Such a combination inhalation device is another aspect of the invention. Such a combination inhalation device can comprise a combined pharmaceutical composition for simultaneous inhaled administration (e.g. dry powder composition), the composition comprising all the individual compounds of the combination, and the composition being incorporated into a plurality of sealed dose containers mounted longitudinally in a strip or ribbon inside the inhalation device, the containers being rupturable or peel-openable on demand; for example such inhalation device can be substantially as described in GB 2,242,134 A (DISKUS™) and/or as described above. Alternatively, the combination inhalation device can be such that the individual compounds of the combination are administrable simultaneously but are stored separately (or wholly or partly stored separately for triple combinations), e.g. in separate pharmaceutical compositions, for example as described in PCT/EP03/00598 filed on 22 Jan. 2003, published as WO 03/061743 (e.g. as described in the claims thereof e.g. claim 1).

The invention also provides a method of preparing a combination as defined herein,
the method comprising either
(a) preparing a separate pharmaceutical composition for administration of the individual compounds of the combination either sequentially or simultaneously, or
(b) preparing a combined pharmaceutical composition for administration of the individual compounds of the combination simultaneously,
wherein the pharmaceutical composition comprises the combination together with one or more pharmaceutically acceptable carriers and/or excipients.

The invention also provides a combination as defined herein, prepared by a method as defined herein.

Biological Test Methods

PDE 3, PDE 4B, PDE 4D, PDE 5, PDE 6 Primary Assay Methods

The activity of the compounds can be measured in the assay methods shown below. Preferred compounds of the invention are selective PDE4 inhibitors, i.e. they inhibit PDE4 (e.g. PDE4B and/or PDE4D, preferably PDE4B) more strongly than they inhibit PDE3 and/or more strongly than they inhibit PDE5 and/or more strongly than they inhibit PDE6.

PDE Enzyme Sources and Literature References

Human recombinant PDE4B, in particular the 2B splice variant thereof (HSPDE4B2B), is disclosed in WO 94/20079 and also M. M. McLaughlin et al., "A low Km, rolipram-sensitive, cAMP-specific phosphodiesterase from human brain: cloning and expression of cDNA, biochemical characterisation of recombinant protein, and tissue distribution of mRNA", *J. Biol. Chem.*, 1993, 268, 6470-6476. For example, in Example 1 of WO 94/20079, human recombinant PDE4B is described as being expressed in the PDE-deficient yeast *Saccharomyces cerevisiae* strain GL62, e.g. after induction by addition of 150 uM $CuSO_4$, and 100,000×g supernatant fractions of yeast cell lysates are described for use in the harvesting of PDE4B enzyme.

Human recombinant PDE4D (HSPDE4D3A) is disclosed in P. A. Baecker et al., "Isolation of a cDNA encoding a human rolipram-sensitive cyclic AMP phoshodiesterase (PDE $IV_D$)", *Gene*, 1994, 138, 253-256.

Human recombinant PDE5 is disclosed in K. Loughney et al., "Isolation and characterisation of cDNAs encoding PDE5A, a human cGMP-binding, cGMP-specific 3',5'-cyclic nucleotide phosphodiesterase", *Gene*, 1998, 216, 139-147.

PDE3 can be purified from bovine aorta, e.g. as described by H. Coste and P. Grondin, "Characterisation of a novel potent and specific inhibitor of type V phosphodiesterase", *Biochem. Pharmacol.*, 1995, 50, 1577-1585.

PDE6 can be purified from bovine retina, e.g. as described by: P. Catty and P. Deterre, "Activation and solubilization of the retinal cGMP-specific phosphodiesterase by limited proteolysis", *Eur. J. Biochem.*, 1991, 199, 263-269; A. Tar et al. "Purification of bovine retinal cGMP phosphodiesterase", *Methods in Enzymology*, 1994, 238, 3-12; and/or D. Srivastava et al. "Effects of magnesium on cyclic GMP hydrolysis by the bovine retinal rod cyclic GMP phosphodiesterase", *Biochem. J.*, 1995, 308, 653-658.

Inhibition of PDE 3, PDE 4B, PDE 4D, PDE 5 or PDE 6 Activity: Radioactive Scintillation Proximity Assay (SPA)

The ability of compounds to inhibit catalytic activity at PDE4B or 4D (human recombinant), PDE3 (from bovine aorta), PDE5 (human recombinant) or PDE6 (from bovine retina) is determined by Scintillation Proximity Assay (SPA) in 96-well format. Test compounds (as a solution in DMSO, preferably about 2 microliter (ul) volume of DMSO solution) are preincubated at ambient temperature (room temperature, e.g. 19-23° C.) in Wallac Isoplates (code 1450-514) with PDE enzyme in 50 mM Tris-HCl buffer pH 7.5, 8.3 mM $MgCl_2$, 1.7 mM EGTA, 0.05% (w/v) bovine serum albumin for 10-30 minutes (usually 30 minutes). The enzyme concentration is adjusted so that no more than 20% hydrolysis of the substrate defined below occurs in control wells without compound, during the incubation. For the PDE3, PDE4B and PDE4D assays, [5',8-$^3$H]Adenosine 3',5'-cyclic phosphate (Amersham Pharmacia Biotech, code TRK.559; or Amersham Biosciences UK Ltd, Pollards Wood, Chalfont St Giles, Buckinghamshire HP8 4SP, UK) is added to give 0.05 uCi per well and ~10 nM final concentration. For the PDE5 and PDE6 assays, [8-$^3$H]Guanosine 3',5'-cyclic phosphate (Amersham Pharmacia Biotech, code TRK.392) is added to give 0.05 uCi per well and ~36 nM final concentration. Plates containing assay mixture, preferably approx. 100 ul volume of assay mixture, are mixed on an orbital shaker for 5 minutes and incubated at ambient temperature for 1 hour. Phosphodiesterase SPA beads (Amersham Pharmacia Biotech, code RPNQ 0150) are added (~1 mg per well) to terminate the assay. Plates are sealed and shaken and allowed to stand at ambient temperature for 35 minutes to 1 hour (preferably 35 minutes) to allow the beads to settle. Bound radioactive product is measured using a WALLAC TRILUX 1450 Microbeta scintillation counter. For inhibition curves, 10 concentrations (1.5 nM-30 uM) of each compound are assayed. Curves are analysed using ActivityBase and XLfit (ID Business Solutions Limited, 2 Ocean Court, Surrey Research Park, Guildford, Surrey GU2 7QB, United Kingdom) Results are expressed as $pIC_{50}$ values.

In an alternative to the above radioactive SPA assay, PDE4B or PDE4D inhibition can be measured in the following Fluorescence Polarisation (FP) assay:

Inhibition of PDE4B or PDE4D Activity: Fluorescence Polarisation (FP) Assay

The ability of compounds to inhibit catalytic activity at PDE4B (human recombinant) or PDE4D (human recombinant) is determined by IMAP Fluorescence Polarisation (FP) assay (IMAP Explorer kit, available from Molecular Devices Corporation, Sunnydale, Calif., USA; Molecular Devices code: R8062) in 384-well format. The IMAP FP assay is able to measure PDE activity in an homogenous, non-radioactive assay format. The FP assay uses the ability of immobilised trivalent metal cations, coated onto nanoparticles (tiny beads), to bind the phosphate group of Fl-AMP that is produced on the hydrolysis of fluorescein-labelled (Fl) cyclic adenosine mono-phosphate (Fl-cAMP) to the non-cyclic Fl-AMP form. Fl-cAMP does not bind. Binding of Fl-AMP product to the beads (coated with the immobilised trivalent cations) slows the rotation of the bound Fl-AMP and leads to an increase in the fluorescence polarisation ratio of parallel to perpendicular light. Inhibition of the PDE reduces/inhibits this signal increase.

Test compounds (small volume, e.g. ca. 0.5 to 1 ul, preferably ca. 0.5 ul, of solution in DMSO) are preincubated at ambient temperature (room temperature, e.g. 19-23° C.) in black 384-well microtitre plates (supplier: NUNC, code 262260) with PDE enzyme in 10 mM Tris-HCl buffer pH 7.2, 10 mM $MgCl_2$, 0.1% (w/v) bovine serum albumin, and 0.05% $NaN_3$ for 10-30 minutes. The enzyme level is set by experimentation so that reaction is linear throughout the incubation. Fluorescein adenosine 3',5'-cyclic phosphate (from Molecular Devices Corporation, Molecular Devices code: R7091) is added to give about 40 nM final concentration (final assay volume usually ca. 20-40 ul, preferably ca. 20 ul). Plates are mixed on an orbital shaker for 10 seconds and incubated at ambient temperature for 40 minutes. IMAP binding reagent (as described above, from Molecular Devices Corporation, Molecular Devices code: R7207) is added (60 ul of a 1 in 400 dilution in binding buffer of the kit stock solution) to terminate the assay. Plates are allowed to stand at ambient temperature for 1 hour. The Fluorescence Polarisation (FP) ratio of parallel to perpendicular light is measured using an Analyst™ plate reader (from Molecular Devices Corporation). For inhibition curves, 10 concentrations (1.5 nM-30 uM) of each compound are assayed. Curves are analysed using ActivityBase and XLfit (ID Business Solutions Limited, 2 Ocean Court, Surrey Research Park, Guildford, Surrey GU2 7QB, United Kingdom). Results are expressed as $pIC_{50}$ values.

In the FP assay, all reagents are dispensed using Multidrop™ (available from Thermo Labsystems Oy, Ratastie 2, PO Box 100, Vantaa 01620, Finland).

For a given PDE4 inhibitor, the PDE4B (or PDE4D) inhibition values measured using the SPA and FP assays can differ slightly. However, in a regression analysis of 100 test compounds (not necessarily compounds of the invention), the $pIC_{50}$ inhibition values measured using SPA and FP assays have been found generally to agree within 0.5 log units, for PDE4B and PDE4D (linear regression coefficient 0.966 for PDE4B and 0.971 for PDE4D; David R. Mobbs et al., "Comparison of the IMAP Fluorescence Polarisation Assay with the Scintillation Proximity Assay for Phosphodiesterase Activity", poster presented at 2003 Molecular Devices UK & Europe User Meeting, 2 Oct. 2003, Down Hall, Harlow, Essex, United Kingdom).

Biological Data obtained for some of the Examples (PDE4B and/or PDE5 inhibitory activity, either as one reading or as an average of ca. 2-6 readings) are as follows, based on current measurements only. In each of the SPA and FP assays, absolute accuracy of measurement is not possible, and the readings given are accurate only up to about ±0.5 of a log unit, depending on the number of readings made and averaged:

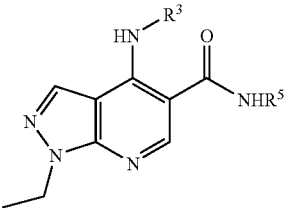

| NHR³ (connection point underlined) | Example numbers | PDE4B pIC$_{50}$ (± about 0.5) | PDE5 pIC$_{50}$ (± about 0.5) | PDE4B to PDE5 Selectivity (PDE4B/PDE5 EMR ratio, not log scale) |
|---|---|---|---|---|
| 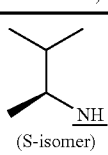<br>(S-isomer) | 6 to 49, 51 | 6.7 to 8.2 | <4.52 to 5.4 | ≧155 to ≧2951 |
| 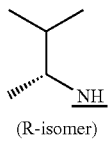<br>(R-isomer) | 1 to 5 | 7.2 to 8.1 | 5.1 to 6.0 | 62 to 182 |
|  | 53 to 57 | 7.0 to 7.8 | <4.52 to 5.4 | 240 to 550 |

PDE4B and PDE5 inhibition Biological Data for some specific Examples are as follows:

| Example no. and structure | PDE4B pIC$_{50}$ (± about 0.5) | PDE5 pIC$_{50}$ (± about 0.5) | Selectivity (PDE4B/PDE5 EMR ratio, not log scale) |
|---|---|---|---|
| Example 1, R¹ = Et, R² = H,<br>NHR³ =  (R-isomer), R⁵ = benzyl | 7.8 | 6.0 | 66 |
| Example 2, R¹ = Et, R² = H,<br>NHR³ = 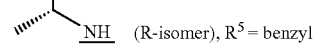 (R-isomer), R⁵ = 4-fluorophenyl | 7.2 | 5.1 | 135 |
| Example 38, R¹ = Et, R² = H,<br>NHR³ =  (S-isomer), R⁵ = benzyl | 7.7 | 5.0 | 501 |
| Example 39, R¹ = Et, R² = H,<br>NHR³ = 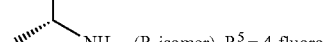 (S-isomer), R⁵ = 4-fluorophenyl | 7.2 | <4.52 | ≧468 |

| Example no. and structure | PDE4B pIC$_{50}$ (± about 0.5) | PDE5 pIC$_{50}$ (± about 0.5) | Selectivity (PDE4B/PDE5 EMR ratio, not log scale) |
| --- | --- | --- | --- |
| Example 51, R$^1$ = Et, R$^2$ = H, NHR$^3$ = 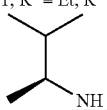 (S-isomer), R$^5$ = 2-ethylbutyl | 8.1 | 5.4 | 437 |
| Example 53, R$^1$ = Et, R$^2$ = H, NHR$^3$ = t-butylamino, R$^5$ = benzyl | 7.8 | 5.4 | 240 |
| Example 54, R$^1$ = Et, R$^2$ = H, NHR$^3$ = t-butylamino, R$^5$ = 4-fluorophenyl | 7.0 | <4.52 | ≧309 |
| Comparative Examples 58, 59 and 60, R$^1$ = Et, R$^2$ = H, NHR$^3$ = sec-butylamino (R—, S—, or racemic), R$^5$ = benzyl | 7.2 to 7.8 | 5.5 to 6.2 | 11 to 55 |
| Comparative Example 60 ( = Ex. 1 of U.S. Pat. No. 3,979,399), R$^1$ = Et, R$^2$ = H, NHR$^3$ = n-butylamino, R$^5$ = n-butyl | 6.8 | 6.4 | 2 |
| Comparative Example 61 ( = Ex. 19 of U.S. Pat. No. 3,979,399), R$^1$ = isopropyl, R$^2$ = H, NHR$^3$ = sec-butylamino, R$^5$ = phenyl | 6.7 | 5.3 | 21 |

The Examples have been tested for PDE4B inhibition using the radioactive SPA assay or the FP assay. All or substantially all of the Examples tested have PDE4B inhibitory activities in the range of pIC$_{50}$=about 6.7 (±about 0.5) to about 8.2 (±about 0.5).

Emnesis: Some known PDE4 inhibitors can cause emesis and/or nausea to greater or lesser extents (e.g. see Z. Huang et al., *Current Opinion in Chemical Biology*, 2001, 5: 432-438, see especially pages 433-434 and refs cited therein). Therefore, it would be preferable, but not essential, if a PDE4 inhibitory compound or salt of the invention were to cause only limited or manageable emetic side-effects. Emetic side-effects can for example be measured by the emetogenic potential of the compound or salt when administered to ferrets; for example one can measure the time to onset, extent, frequency and/or duration of vomiting, retching and/or writhing in ferrets after oral or parenteral administration of the compound or salt. See for example In vivo Assay 4 hereinafter for a measurement method for anti-inflammatory effect, emetic side-effects and therapeutic index (TI) in the ferret. See also for example A. Robichaud et al., "Emesis induced by inhibitors of [PDE IV] in the ferret", *Neuropharmacology*, 1999, 38, 289-297, erratum *Neuropharmacology*, 2001, 40, 465-465. However, optionally, emetic side-effects and therapeutic index (TI) in rats can be conveniently measured by monitoring the pica feeding behaviour of rats after administration of the compound or salt of the invention (see In Vivo Assay 2 below).

Other side effects: Some known PDE4 inhibitors can cause other side effects such as headache and other central nervous system (CNS-) mediated side effects; and/or gastrointestinal (GI) tract disturbances. Therefore, it would be preferable but not essential if a particular PDE4 inhibitory compound or salt of the invention were to cause only limited or manageable side-effects in one or more of these side-effect categories.

In Vivo Biological Assays

The in vitro enzymatic PDE4B inhibition assay described above should be regarded as being the primary test of biological activity. However, additional in vivo biological tests, which are optional and which are not an essential measure of efficacy or side-effects, are described below.

In Vivo Assay 1. LPS-Induced Pulinonary Neutrophilia in Rats: Effect of Orally Administered PDE4 Inhibitors Pulmonary neutrophil influx has been shown to be a significant component to the family of pulmonary diseases like chronic obstructive pulmonary disease (COPD) which can involve chronic bronchitis and/or emphysema (G. F. Filley, *Chest.* 2000; 117(5); 251s-260s). The purpose of this neutrophilia model is to study the potentially anti-inflammatory effects in vivo of orally administered PDE4 inhibitors on neutrophilia induced by inhalation of aerosolized lipopolysaccharide (LPS), modelling the neutrophil inflammatory component(s) of COPD. See the literature section below for scientific background.

Male Lewis rats (Charles River, Raleigh, N.C., USA) weighing approximately 300-400 grams are pretreated with either (a) test compound suspended in 0.5% methylcellulose (obtainable from Sigma-Aldrich, St Louis, Mo., USA) in water or (b) vehicle only, delivered orally in a dose volume of 10 ml/kg. Generally, dose response curves are generated using the following doses of PDE4 inhibitors: 10.0, 2.0, 0.4, 0.08 and 0.016 mg/kg. Thirty minutes following pretreatment, the rats are exposed to aerosolized LPS (Serotype *E. Coli* 026:B6 prepared by trichloroacetic acid extraction, obtainable from Sigma-Aldrich, St Louis, Mo., USA), generated from a nebulizer containing a 100 μg/ml LPS solution. Rats are exposed to the LPS aerosol at a rate of 4 L/min for 20 minutes. LPS exposure is carried out in a closed chamber with internal dimensions of 45 cm length×24 cm width×20 cm height. The nebulizer and exposure chamber are contained in a certified fume hood. At 4 hours-post LPS exposure the rats are euthanized by overdose with pentobarbital at 90 mg/kg, administered intraperitoneally. Bronchoalveolar lavage (BAL) is performed through a 14 gauge blunt needle into the exposed trachea. Five, 5 ml washes are performed to collect a total of 25 ml of BAL fluid. Total cell counts and leukocyte differentials are performed on BAL fluid in order to calculate neutrophil influx into the lung. Percent neutrophil inhibition at each dose (cf. vehicle) is calculated and a variable slope, sigmoidal dose-response curve is generated, usually using Prism Graph-Pad. The dose-response curve is used to calculate an ED50 value (in mg per kg of body weight) for inhibition by the PDE4 inhibitor of the LPS-induced neutrophilia.

Alternative method: In an alternative embodiment of the procedure, a single oral dose of 10 mg/kg or 1.0 mg/kg of the PDE4 inhibitor (or vehicle) is administered to the rats, and percent neutrophil inhibition is calculated and reported for that specific dose.

Literature:

Filley G. F. Comparison of the structural and inflammatory features of COPD and asthma. *Chest.* 2000; 117(5) 251s-260s.

Howell R E, Jenkins L P, Fielding L E, and Grimes D. Inhibition of antigen-induced pulmonary eosinophilia and neutrophilia by selective inhibitors of phosphodiesterase types 3 and 4 in brown Norway rats. *Pulmonary Pharmacology.* 1995; 8: 83-89.

Spond J, Chapman R, Fine J, Jones H, Kreutner W, Kung T T, Minnicozzi M. Comparison of PDE 4 inhibitors, Rolipram and SB 207499 (Ariflo™), in a rat model of pulmonary neutrophilia. *Pulmonary Pharmacology and Therapeutics.* 2001; 14:157-164.

Underwood D C, Osborn R R, Bochnowicz S, Webb E F, Rieman D J, Lee J C, Romanic A M, Adams J L, Hay D W P, and Griswold D E. SB 239063, a p 38 MAPK inhibitor, reduces neutrophilia, inflammatory cytokines, MMP-9, and fibrosis in lung. *Am J Physiol Lung Cell Mol Physiol.* 2000; 279: L895-L902.

In Vivo Assay 2. Rat Pica Model of Emesis

Background: Selective PDE4 inhibitors have been shown to inhibit inflammation in various in vitro and in vivo models by increasing intracellular levels of cAMP of many immune cells (e.g. lymphocytes, monocytes). However, a side effect of some PDE4 inhibitors in many species is emesis. Because many rat models of inflammation are well characterized, they have been used in procedures (see e.g. In Vivo Assay 1 above) to show beneficial anti-inflammatory effects of PDE 4 inhibitors. However rats have no emetic response (they have no vomit reflex), so that the relationship between beneficial anti-inflammatory effects of PDE 4 inhibitors and emesis is difficult to study directly in rats.

However, in 1991, Takeda et al. (see Literature section below) demonstrated that the pica feeding response is analogous to emesis in rats. Pica feeding is a behavioural response to illness in rats wherein rats eat non-nutritive substances such as earth or in particular clay (e.g. kaolin) which may help to absorb toxins. Pica feeding can be induced by motion and chemicals (especially chemicals which are emetic in humans), and can be inhibited pharmacologically with drugs that inhibit emesis in humans. The Rat Pica Model, In Vivo Assay 2, can determine the level of pica response of rats to PDE 4 inhibition at pharmacologically relevant doses in parallel to in vivo anti-inflammatory Assays in (a separate set of) rats (e.g. In Vivo Assay 1 above).

Anti-inflammatory and pica assays in the same species together can provide data on the "therapeutic index" (TI) in the rat of the compounds/salts of the invention. The Rat TI can for example be calculated as the ratio of a) the potentially-emetic Pica Response ED50 dose from Assay 2 to b) the rat anti-inflammatory ED50 dose (e.g. measured by rat neutrophilia-inhibition in eg In Vivo Assay 1), with larger TI ratios possibly indicating lower emesis at many anti-inflammatory doses. This might allow a choice of a non-emetic or minimal-emetic pharmaceutical dose of the compounds or salts of the invention which has an anti-inflammatory effect. It is recognised however that achieving a low-emetic PDE4 inhibitory compound is not essential to the invention.

Procedure: On the first day of the experiment, the rats are housed individually in cages without bedding or "enrichment". The rats are kept off of the cage floor by a wire screen. Pre-weighed food cups containing standard rat chow and clay pellets are placed in the cage. The clay pellets, obtainable from Languna Clay Co, City of Industry, Calif., USA, are the same size and shape as the food pellets. The rats are acclimated to the clay for 72 hours, during which time the cups and food and clay debris from the cage are weighed daily on an electronic balance capable of measuring to the nearest 0.1 grams. By the end of the 72 hour acclimation period the rats generally show no interest in the clay pellets.

At the end of 72 hours the rats are placed in clean cages and the food cups weighed. Rats that are still consuming clay regularly are removed from the study. Immediately prior to the dark cycle (the time when the animals are active and should be eating) the animals are split into treatment groups and dosed orally with a dose of the compound/salt of the invention (different doses for different treatment groups) or with vehicle alone, at a dose volume of 2 ml/kg. In this oral dosing, the compound/salt is in the form of a suspension in 0.5% methylcellulose (obtainable Sigma-Aldrich, St. Louis, Mo., USA) in water. The food and clay cups and cage debris are weighed the following day and the total clay and food consumed that night by each individual animal is calculated.

A dose response is calculated by first converting the data into quantal response, where animals are either positive or negative for the pica response. A rat is "pica positive" if it consumes greater than or equal to 0.3 grams of clay over the mean of is usually calculated using logistic regression performed by the Statistica software statistical package. A Pica Response ED50 value in mg per kg of body weight can then be calculated.

The Pica Response ED50 value can be compared to the neutrophilia-inhibition ED50 values for the same compound administered orally to the rat (measurable by In Vivo Assay 1 above), so that a Therapeutic Index (TI) in rats can be calculated thus:

$$\text{Rat Therapeutic index } (TI)(50/50) = \frac{\text{Pica Response } ED50 \text{ value}}{\text{rat neutrophilia-inhibition } ED50 \text{ value}}$$

In general, the Therapeutic Index (TI) calculated this way is often substantially different to, and for example can often be substantially higher than, the TI (D20/D50) calculated in the ferret (see In vivo Assay 4 below).

Literature:

Beavo J A, Contini, M., Heaslip, R. J. Multiple cyclic nucleotide phosphodiesterases. *Mol Pharmacol.* 1994; 46:399-405.

Spond J, Chapman R, Fine J, Jones H, Kreutner W, Kung T T, Minnicozzi M. Comparison of PDE 4 inhibitors, Rolipram and SB 207499 (Ariflo™), in a rat model of pulmonary neutrophilia. *Pulmonary Pharmacology and Therapeudtics.* 2001; 14:157-164.

Takeda N, Hasegawa S, Morita M, and Matsunaga T. Pica in rats is analogous to emesis: an animal model in emesis research. *Pharmacology, Biochemistry and Behavior.* 1991; 45:817-821.

Takeda N, Hasegawa S, Morita M, Horii A, Uno A, Yamatodani A and Matsunaga T. Neuropharmacological mechanisms of emesis. I. Effects of antiemetic drugs on motion- and apomorphine-induced pica in rats. *Meth Find Exp Clin Pharmacol.* 1995; 17(9) 589-596.

Takeda N, Hasegawa S, Morita M, Horii A, Uno A, Yamatodani A and Matsunaga T. Neuropharmacological mechanisms of emesis. II. Effects of antiemetic drugs on cisplatin-induced pica in rats. *Meth Find Exp Clin Pharmacol.* 1995; 17(9) 647-652.

In Vivo Assay 3. LPS Induced Pulmonary Neutrophilia in Rats: Effect of Intratracheally Administered PDE4 Inhibitors This assay is an animal model of inflammation in the lung—specifically neutrophilia induced by lipopolysaccharide (LPS)—and allows the study of putative inhibition of such neutrophilia (anti-inflammatory effect) by intratracheally (i.t.) administered PDE4 inhibitors. The PDE4 inhibitors are preferably in dry powder or wet suspension form. I.t. administration is one model of inhaled administration, allowing topical delivery to the lung.

Animals: Male CD (Sprague Dawley Derived) rats supplied by Charles River, Raleigh, N.C., USA are housed in groups of 5 rats per cage, acclimatised after delivery for at least 7 days with bedding/nesting material regularly changed, fed on SDS diet R1 pelleted food given ad lib, and supplied with daily-changed pasteurised animal grade drinking water.

Device for dry powder administration: Disposable 3-way tap between dosing needle and syringe. A 3-way sterile tap (Vycon Ref 876.00) is weighed, the drug blend or inhalation grade lactose (vehicle control) is then added to the tap, the tap closed to prevent loss of drug, and the tap is re-weighed to determine the weight of drug in the tap. After dosing, the tap is weighed again to determine the weight of drug that had left the tap. The needle, a Sigma Z21934-7 syringe needle 19-gauge 152 mm (6 inches) long with luer hub, is cut by engineering to approximately 132 mm (5.2 inches), a blunt end is made to prevent them damaging the rat's trachea, and the needle is weighed prior to and after drug delivery to confirm that no drug is retained in the needles after dosing.

Device for wet suspension administration: This is the similar to the above but a blunt dosing needle, whose forward end is slightly angled to the needle axis, is used, with a flexible plastic portex canula inserted into the needle.

Drugs and Materials: Lipopolysaccharide (LPS) (Serotype:0127:B8) (L3129 Lot 61K4075) is dissolved in phosphate-buffered saline (PBS). PDE4 inhibitors are used in size-reduced (e.g. micronised) form, for example according to the Micronisation Example given above. For dry powder administration of the drug, the Dry Powder Formulation Example given above, comprising drug and inhalation-grade lactose, can be used. The inhalation-grade lactose usually used (Lot E98L4675 Batch 845120) has 10% fines (10% of material under 15 um particle size measured by Malvern particle size). Wet suspensions of the drug can be prepared by adding the required volume of vehicle to the drug; the vehicle used being a mixture of saline/tween (0.2% tween 80). The wet suspension is sonicated for 10 minutes prior to use.

Preparation, and dosing with PDE 4 inhibitor: Rats are anaesthetised by placing the animals in a sealed Perspex chamber and exposing them to a gaseous mixture of isoflourane (4.5%), nitrous oxide (3 liters·minute$^{-1}$) and oxygen (1 liter.minute$^{-1}$). Once anaesthetised, the animals are placed onto a stainless steel i.t. dosing support table. They are positioned on their back at approximately a 35° angle. A light is angled against the outside of the throat to highlight the trachea. The mouth is opened and the opening of the upper airway visualised. The procedure varies for wet suspension and dry powder administration of PDE4 inhibitors as follows:

Dosing with a Wet suspension: A portex cannula is introduced via a blunt metal dosing needle that has been carefully inserted into the rat trachea. The animals are intratracheally dosed with vehicle or PDE4 inhibitor via the dosing needle with a new internal canula used for each different drug group. The formulation is slowly (10 seconds) dosed into the trachea using a syringe attached to the dosing needle.

Dosing with a Dry Powder: The three-way tap device and needle are inserted into the rat trachea up to a pre-determined point established to be located approximately 1 cm above the primary bifurcation. Another operator holds the needle at the specified position whilst 2×4 ml of air is delivered through the three-way tap by depressing the syringes (ideally coinciding with the animal inspiring), aiming to expel the entire drug quantity from the tap. After dosing, the needle and tap are removed from the airway and the tap closed off to prevent any retained drug leaving the tap.

After dosing with either wet suspension or dry powder, the animals are then removed from the table and observed constantly until they have recovered from the effects of anaesthesia. The animals are returned to the holding cages and given free access to food and water; they are observed and any unusual behavioural changes noted.

Exposure to LPS: About 2 hours after i.t. dosing with vehicle control or the PDE4 inhibitor, the rats are placed into sealed Perspex containers and exposed to an aerosol of LPS (nebuliser concentration 150 µg·ml$^{-1}$) for 15 minutes. Aerosols of LPS are generated by a nebuliser (DeVilbiss, USA) and this is directed into the Perspex exposure chamber. Following the 15-minute LPS-exposure period, the animals are returned to the holding cages and allowed free access to both food and water.

[In an alternative embodiment, the rats can exposed to LPS less than 2 hours after i.t. dosing. In another alternative embodiment, the rats can exposed to LPS more than 2 hours (e.g. ca. 4 or ca. 6 hours) after i.t. dosing by vehicle or PDE4 inhibitor, to test whether or not the PDE4 inhibitor has a long duration of action (which is not essential).]

Bronchoalveolar lavage: 4 hours after LPS exposure the animals are killed by overdose of sodium pentobarbitone (i.p.). The trachea is cannulated with polypropylene tubing and the lungs are lavaged (washed out) with 3×5 mls of heparinised (25 units·ml$^{-1}$) phosphate buffered saline (PBS).

Neutrophil cell counts: The Bronchoalveolar lavage (BAL) samples are centrifuged at 1300 rpm for 7 minutes. The supernatant is removed and the resulting cell pellet resuspended in 1 ml PBS. A cell slide of the resuspension fluid is prepared by placing 100 µl of resuspended BAL fluid into cytospin holders and then is spun at 5000 rpm for 5 minutes. The slides are allowed to air dry and then stained with Leishmans stain (20 minutes) to allow differential cell counting. The total cells are also counted from the resuspension. From these two counts, the total numbers of neutrophils in the BAL are determined. For a measure of PDE4-inhibitor-induced inhibition of neutrophilia, a comparison of the neutrophil count in rats treated with vehicle and rats treated with PDE4 inhibitors is conducted.

By varying the dose of the PDE4 inhibitor used in the dosing step (e.g. 0.2 or 0.1 mg of PDE4 inhibitor per kg of body weight, down to e.g. 0.01 mg/kg), a dose-response curve can be generated.

In Vivo Assay 4. Evaluation of Therapeutic Index of Orally-administered PDE 4 inhibitors in the conscious ferret 1.1 Materials The following materials are used for these studies:

PDE4 inhibitors are prepared for oral (p.o.) administration by dissolving in a fixed volume (1 ml) of acetone and then adding cremophor to 20% of the final volume. Acetone is evaporated by directing a flow of nitrogen gas onto the solution. Once the acetone is removed, the solution is made up to final volume with distilled water. LPS is dissolved in phosphate buffered saline.

1.2 Animals

Male ferrets (*Mustela Pulorius* Furo, weighing 1-2 kg) are transported and allowed to acclimatise for not less than 7 days. The diet comprises SDS diet C pelleted food given ad lib with Whiskers™ cat food given 3 times per week. The animals are supplied with pasteurised animal grade drinking water changed daily.

1.3 Experimental Protocol(s)

1.3.1 Dosing with PDE4 Inhibitors

PDE4 inhibitors are administered orally (p.o.), using a dose volume of 1 ml/kg. Ferrets are fasted overnight but allowed free access to water. The animals are orally dosed with vehicle or PDE 4 inhibitor using a 15 cm dosing needle that is passed down the back of the throat into the oesophagus. After dosing, the animals are returned to holding cages fitted with perspex doors to allow observation, and given free access to water. The animals are constantly observed and any emetic episodes (retching and vomiting) or behavioural changes are recorded. The animals are allowed access to food 60-90 minutes after p.o. dosing.

1.3.2 Exposure to LPS

Thirty minutes after oral dosing with compound or vehicle control, the ferrets are placed into sealed perspex containers and exposed to an aerosol of LPS (30 μg/ml) for 10 minutes. Aerosols of LPS are generated by a nebuliser (DeVilbiss, USA) and this is directed into the perspex exposure chamber. Following a 10-minute exposure period, the animals are returned to the holding cages and allowed free access to water, and at a later stage, food. General observation of the animals continues for a period of at least 2.5 hours post oral dosing. All emetic episodes and behavioural changes are recorded.

1.3.3 Bronchoalveolar lavage and Cell Counts

Six hours after LPS exposure the animals are killed by overdose of sodium pentobarbitone administered intraperitoneally. The trachea is then cannulated with polypropylene tubing and the lungs lavaged twice with 20 ml heparinised (10 units/ml) phosphate buffered saline (PBS). The bronchoalveolar lavage (BAL) samples are centrifuged at 1300 rpm for 7 minutes. The supernatant is removed and the resulting cell pellet re-suspended in 1 ml PBS. A cell smear of re-suspended fluid is prepared and stained with Leishmans stain to allow differential cell counting. A total cell count is made using the remaining re-suspended sample. From this, the total number of neutrophils in the BAL sample is determined.

1.3.4 Pharmacodynamic Readouts

The following parameters are recorded:

a) % inhibition of LPS-induced pulmonary neutrophilia to determine the dose of PDE4 inhibitor which gives 50% inhibition (D50).

b) Emetic episodes—the number of vomits and retches are counted to determine the dose of PDE4 inhibitor that gives a 20% incidence of emesis (D20).

c) A therapeutic index (TI), using this assay, is then calculated for each PDE4 inhibitor using the following equation:

$$\text{Ferret Therapeutic index } (TI)(D20/D50) = \frac{D20 \text{ incidence of emesis in ferret}}{D50 \text{ inhibition of neutrophilia in ferret}}$$

It is noted that the Ferret Therapeutic index (TI) (D20/D50) calculated using this in vivo Assay 4 is often substantially different to, and for example is often substantially lower than, the Rat TI (50/50) calculated using the rat oral inflammation and pica feeding Assays 1+2.

The calculation of Ferret TI using the known PDE4 inhibitor roflumilast in this Assay 4 is:

D20 for emesis=about 0.46 mg/kg p.o.,

D50 for ferret neutroplilia=about 0.42 mg/kg p.o.,

Ferret TI=about 1.1.

All publications, including but not limited to patents and patent applications, cited in this specification are herein incorporated by reference as if each individual publication were specifically and individually indicated to be incorporated by reference herein as though fully set forth.

EXAMPLES

The various aspects of the invention will now be described by reference to the following examples. These examples are merely illustrative and are not to be construed as a limitation of the scope of the present invention. In this section, "Intermediates" represent syntheses of intermediate compounds intended for use in the synthesis of the "Examples".

Abbreviations used herein:

| | |
|---|---|
| EtOAc | ethyl acetate |
| DMF | dimethyl formamide |
| MeOH | methanol |
| HPLC | high pressure liquid chromatography |
| SPE | solid phase extraction |
| LCMS | liquid chromatography/mass spectroscopy |
| EDC | 1-(3-Dimethylaminopropyl)-3-ethylcarbodiimide hydrochloride |
| HATU | O-(7-Azabenzotriazol-1-yl)-N,N,N',N'-tetramethyluronium hexafluorophosphate |
| DIPEA | diisopropylethyl amine ($^i$Pr$_2$NEt) |
| $T_{RET}$ | retention time |
| Room temperature | this is usually in the range of about 20 to about 25° C. |

Machine Methods used herein:

LCMS (Liquid Chromatography/Mass Spectroscopy)

Waters ZQ mass spectrometer operating in positive ion electrospray mode, mass range 100-1000 amu.

UV wavelength: 215-330 nM

Column: 3.3 cm×4.61 mm ID, 3 μm ABZ+PLUS

Flow Rate: 3 ml/min

Injection Volume: 5 μl

Solvent A: 95% acetonitrile+0.05% formic acid

Solvent B: 0.1% formic acid+10 mMolar ammonium acetate

Gradient: 0% A/0.7 min, 0-100% A/3.5 min, 100% A/1.1 min, 100-0% A/0.2 min

Mass Directed Autoprep HPLC

The prep column used was a Supelcosil ABZplus (10 cm×2.12 cm) (usually 10 cm×2.12 cm×5 μm).

UV wavelength: 200-320 nM

Flow: 20 ml/min

Injection Volume: 1 ml; or more preferably 0.5 ml

Solvent A: 0.1% formic acid

Solvent B: 95% acetonitrile+5% formic acid; or more usually 99.95% acetonitrile+0.05% formic acid Gradient: 100% A/1 min, 100-80% A/9 min, 80-1% A/3.5 min, 1% A/1.4 min, 1-100% A/0.1 min Table of Intermediates

| Intermediate Number | Name |
|---|---|
| 1 | Ethyl 4-chloro-1-ethyl-1H-pyrazolo[3,4-b]pyridine-5-carboxylate |
| 2 | Ethyl 4-{[(1R)-1,2-dimethylpropyl]amino}-1-ethyl-1H-pyrazolo[3,4-b]pyridine-5-carboxylate |
| 3 | Ethyl 4-{[(1S)-1,2-dimethylpropyl]amino}-1-ethyl-1H-pyrazolo[3,4-b]pyridine-5-carboxylate |
| 4 | 4-{[(1R)-1,2-Dimethylpropyl]amino}-1-ethyl-1H-pyrazolo[3,4-b]pyridine-5-carboxylic acid |
| 5 | 4-{[(1S)-1,2-Dimethylpropyl]amino}-1-ethyl-1H-pyrazolo[3,4-b]pyridine-5-carboxylic acid |
| 6 | Ethyl 4-(tert-butylamino)-1-ethyl-1H-pyrazolo[3,4-b]pyridine-5-carboxylate |
| 7 | 4-(tert-Butylamino)-1-ethyl-1H-pyrazolo[3,4-b]pyridine-5-carboxylic acid |

Intermediate 1

Ethyl 4-chloro-1-ethyl-1H-pyrazolo[3,4-b]pyridine-5-carboxylate

Prepared from commercially available 5-amino-1-ethyl pyrazole as described by G. Yu et. al. in *J. Med Chem.*, 2001, 44, 1025-1027:

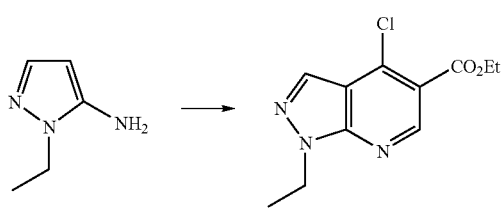

Intermediate 2

Ethyl 4-{[(1R)-1,2-dimethylpropyl]amino}-1-ethyl-1H-pyrazolo[3,4-b]pyridine-5-carboxylate

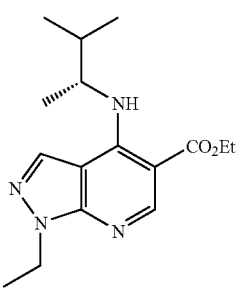

[(1R)-1,2-dimethylpropyl]amine (0.189 g, 2.17 mmol, commercially available from Lancaster Synthesis) was added to a stirred solution of Intermediate 1 (0.5 g, 1.97 mmol) and DIPEA (1.72 ml, 1.27 g, 9.85 mmol) in acetonitrile (10 ml). The resulting solution was heated at 85° C. under nitrogen. After 22 h, the reaction mixture was evaporated to dryness and the residual oil was distributed between dichloromethane (30 ml) and water (20 ml). The phases were separated by passage through a hydrophobic frit, and the organic phase was dried over anhydrous sodium sulphate and evaporated to afford Intermediate 2 as a colourless viscous oil (0.575 g). LCMS showed $MH^+$=305; $T_{RET}$=3.45 min.

Intermediate 3

Ethyl 4-{[(1S)-1,2-dimethylpropyl]amino}-1-ethyl-1H-pyrazolo[3,4-b]pyridine-5-carboxylate

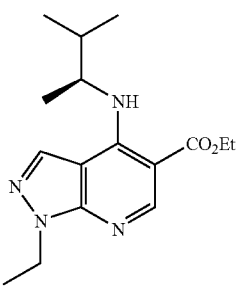

[(1S)-1,2-dimethylpropyl]amine (0.189 g, 2.17 mmol, commercially available from Lancaster Synthesis) was added to a stirred solution of Intermediate 1 (0.5 g, 1.97 mmol) and DIPEA (1.72 ml, 1.27 g, 9.85 mmol) in acetonitrile (10 ml). The resulting solution was heated at 85° C. under nitrogen. After 22 h, the reaction mixture was evaporated to dryness and the residual oil was distributed between dichloromethane (30 ml) and water (20 ml). The phases were separated by passage through a hydrophobic frit, and the organic phase was dried over anhydrous sodium sulphate and evaporated to afford Intermediate 3 as a colourless viscous oil (0.58 g). LCMS showed $MH^+$=305; $T_{RET}$=3.44 min.

Intermediate 4

(4-{[(1R)-1,2-dimethylpropyl]amino}-1-ethyl-1H-pyrazolo[3,4-b]pyridine-5-carboxylic acid

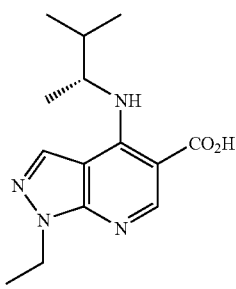

A solution of sodium hydroxide (0.298 g, 7.44 mmol) in water (2 ml) was added to a stirred solution of Intermediate 2 (0.565 g, 1.86 mmol) in ethanol (10 ml), and the resulting mixture was heated at 85° C. After 4 h, the reaction mixture was concentrated in vacuo to give a residual oil which was dissolved in water (10 ml) and adjusted to pH3 with 2M hydrochloric acid. After stirring at 0° C. for 20 min, the resulting precipitate was collected by filtration, washed with cooled water and dried in vacuo to afford Intermediate 4 as a white solid (0.411 g). LCMS showed $MH^+=277$; $T_{RET}=2.78$ min.

Intermediate 5

4-{[(1S)-1,2-dimethylpropyl]amino}-1-ethyl-1H-pyrazolo[3,4-b]pyridine-5-carboxylic acid

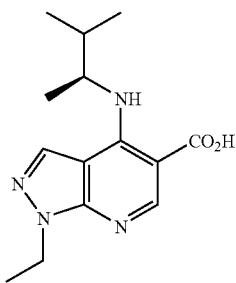

A solution of sodium hydroxide (0.298 g, 7.44 mmol) in water (2 ml) was added to a stirred solution of Intermediate 3 (0.566 g, 1.86 mmol) in ethanol (10 ml), and the resulting mixture was heated at 85° C. After 4 h, the reaction mixture was concentrated in vacuo to give a residual oil which was dissolved in water (10 ml) and adjusted to pH3 with 2M hydrochloric acid. After stirring at 0° C. for 30 min, the resulting precipitate was collected by filtration, washed with cooled water and dried in vacuo to afford Intermediate 5 as a white solid (0.357 g). LCMS showed $MH^+=277$; $T_{RET}=2.78$ min.

Intermediate 6

Ethyl 4-[(1,1-dimethylethyl)amino]-1-ethyl-1H-pyrazolo[3,4-b]pyridine-5-carboxylate

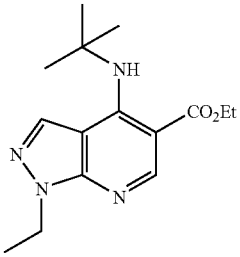

2-Methyl-2-propanol (0.228 ml, 2.17 mmol) was added to a stirred solution of Intermediate 1 (0.5 g, 1.97 mmol) and DIPEA (1.72 ml, 1.27 g, 9.85 mmol) in acetonitrile (10 ml). The resulting solution was heated at 85° C. under nitrogen. After 22 h, a further portion of 2-methyl-2-propanol (0.114 ml, 1.09 mmol) was added to the reaction mixture and stirring was continued at 85° C. After another 24 h a final portion of 2-methyl-2-propanol (0.228 ml, 2.17 mmol) was added to the reaction mixture and stirring was continued at 85° C. After a further 24 h, the reaction mixture was evaporated to dryness and the residual solid was distributed between dichloromethane (30 ml) and water (20 ml). The phases were separated by passage through a hydrophobic frit, and the organic phase was dried over anhydrous sodium sulphate and evaporated to give an off white solid (0.553 g). This solid was dissolved in dichloromethane (10 ml) and applied to a SPE cartridge (20 g, silica). The cartridge was eluted sequentially with a gradient of ethyl acetate-petroleum ether (1:16, then 1:8, 1:4, 1:2, 1:1 and 1:0). Fractions containing the desired material were concentrated in vacuo to afford Intermediate 6 as a white solid (0.456 g). LCMS showed $MH^+=291$; $T_{RET}=3.28$ min.

Intermediate 7

4-[(1,1-Dimethylethyl)amino]-1-ethyl-1H-pyrazolo[3,4-b]pyridine-5-carboxylic acid

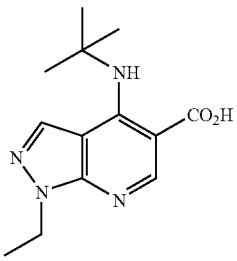

A solution of sodium hydroxide (0.245 g, 6.12 mmol) in water (1.5 ml) was added to a stirred solution of Intermediate 6 (0.446 g, 1.53 mmol) in ethanol (8 ml), and the resulting mixture was heated at 85° C. After 4 h, the reaction mixture was concentrated in vacuo to give a residual oil which was dissolved in water (8 ml) and adjusted to pH3 with 2M hydrochloric acid. After stirring at 0° C. for 20 min, the resulting precipitate was collected by filtration, washed with cooled water and dried in vacuo to afford Intermediate 7 as a white solid (0.33 g). LCMS showed $MH^+=263$; $T_{RET}=2.55$ min.

Intermediate 8

4-Chloro-1-ethyl-1H-pyrazolo[3,4-b]pyridine-5-carboxylic acid

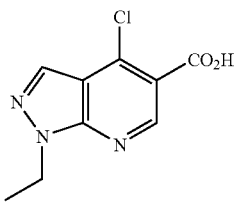

A solution of Intermediate 1 (5.0 g, 19.7 mmol) in dioxane (35 ml) was treated with potassium hydroxide (8.84 g, 158 mmol) as a solution in water (25 ml). The resulting mixture was stirred vigorously at 20° C. for 16 h, then diluted with water (175 ml), and acidified to pH3 with 5M hydrochloric acid. After stirring at 0° C. for 30 min, the resulting precipitate was collected by filtration, washed with cooled water and dried in vacuo over phosphorus pentoxide to afford Intermediate 8 as a white solid (4.33 g). LCMS showed MH$^+$=226; T$_{RET}$=2.56 min.

Intermediate 10

4-Chloro-1-ethyl-N-(phenylmethyl)-1H-pyrazolo[3,4-b]pyridine-5-carboxamide

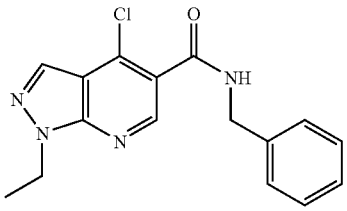

Intermediate 8 (4.32 g, 19.15 mmol) was treated with thionyl chloride (20 ml) and the resulting mixture was heated under reflux for 1 h. Excess thionyl chloride was removed in vacuo, and the residual solid was azeotroped with dichloromethane to afford Intermediate 9, presumed to be the acid chloride derivative of Intermediate 8, as an off-white solid (4.7 g).

Benzylamine (2.2 ml, 20.1 mmol) and diisopropylethylamine (5.0 ml, 28.7 mmol) were added to a stirred solution of Intermediate 9 (4.7 g) in dry tetrahydrofuran (50 ml) at 15° C. The resulting mixture was then stirred at 20° C. for 2.5 h. The reaction mixture was concentrated in vacuo, and the residual solid was partitioned between dichloromethane (150 ml) and water (75 ml). After separation of the phases, the organic phase was dried over anhydrous sodium sulphate and evaporated in vacuo to afford Intermediate 10 as a pale yellow solid (6.1 g). LCMS showed MH$^+$=315; T$_{RET}$=2.89 min.

Intermediate 11

Ethyl 4-chloro-1-ethyl-6-methyl-1H-pyrazolo[3,4-b]pyridine-5-carboxylate

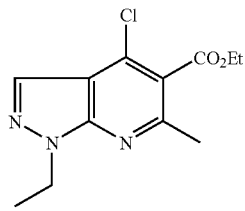

A mixture of 5-amino-1-ethylpyrazole (1.614 g, 14.5 mmol) and diethyl 2-(1-ethoxyethylidene)malonate (3.68 g, 16.0 mmol, as described by P. P. T. Sah, J. Amer. Chem. Soc., 1931, 53, 1836) was heated at 150° C. under Dean Stark conditions for 5 hours. Phosphorous oxychloride (25 ml) was carefully added to the mixture and the resulting solution was heated at 130° C. under reflux for 18 hours. The mixture was concentrated in vacuo, then the residual oil was carefully added, with cooling, to water (100 ml). The resulting mixture was extracted with DCM (3×100 ml) and the combined organic extracts were dried over anhydrous sodium sulphate and concentrated in vacuo. The residual oil was purified by Biotage chromatography (silica, 90 g) eluting with ethyl acetate-petrol (1:19). Fractions containing the desired product were combined and concentrated in vacuo to afford Intermediate 58 (1.15 g). LCMS showed MH$^+$=268; T$_{RET}$=3.18 min.

Intermediate 12

Intermediate 12 was synthesised according to the following reaction scheme:

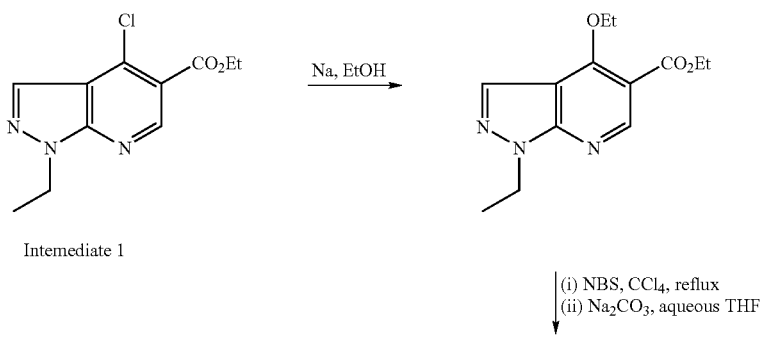

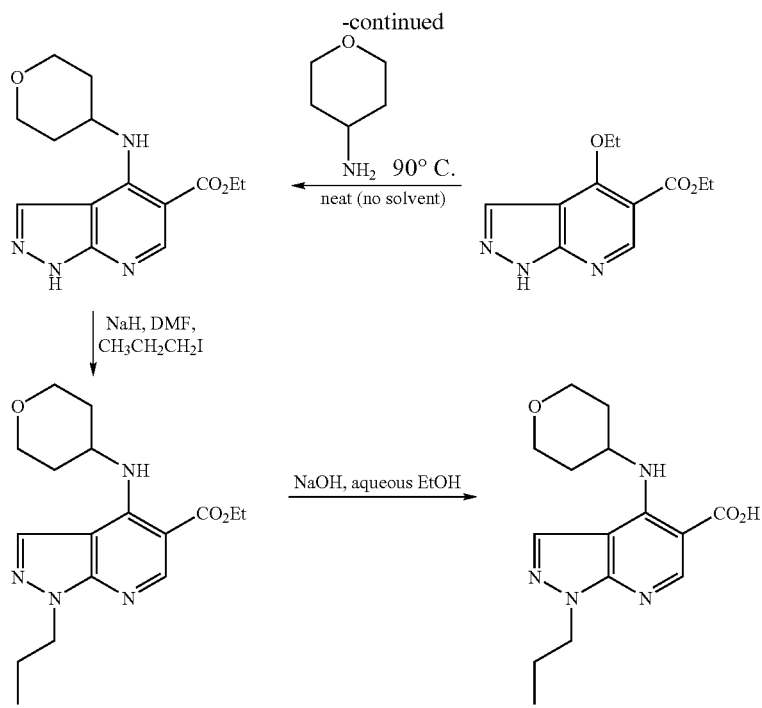

Intermediate 12

TABLE OF EXAMPLES

| Example Number | Name |
|---|---|
| 1 | N-Benzyl-4-{[(1R)-1,2-dimethylpropyl]amino}-1-ethyl-1H-pyrazolo[3,4-b]pyridine-5-carboxamide |
| 2 | 4-{[(1R)-1,2-Dimethylpropyl]amino}-1-ethyl-N-(4-fluorophenyl)-1H-pyrazolo[3,4-b]pyridine-5-carboxamide |
| 3 | 4-{[(1R)-1,2-Dimethylpropyl]amino}-1-ethyl-N-[4-(trifluoromethyl)benzyl]-1H-pyrazolo[3,4-b]pyridine-5-carboxamide |
| 4 | N-(2,3-Dihydro-1H-inden-2-yl)-4-{[(1R)-1,2-dimethylpropyl]amino}-1-ethyl-1H-pyrazolo[3,4-b]pyridine-5-carboxamide |
| 5 | 4-{[(1R)-1,2-Dimethylpropyl]amino}-1-ethyl-N-[4-(methylsulfonyl)benzyl]-1H-pyrazolo[3,4-b]pyridine-5-carboxamide |
| 6 | N-[4-(Difluoromethoxy)benzyl]-4-{[(1S)-1,2-dimethylpropyl]amino}-1-ethyl-1H-pyrazolo[3,4-b]pyridine-5-carboxamide |
| 7 | 4-{[(1S)-1,2-Dimethylpropyl]amino}-1-ethyl-N-[(2-methyl-1,3-thiazol-4-yl)methyl]-1H-pyrazolo[3,4-b]pyridine-5-carboxamide |
| 8 | N-[(5-Chloropyridin-2-yl)methyl]-4-{[(1S)-1,2-dimethylpropyl]amino}-1-ethyl-1H-pyrazolo[3,4-b]pyridine-5-carboxamide |
| 9 | N-(2-Chloro-6-fluorobenzyl)-4-{[(1S)-1,2-dimethylpropyl]amino}-1-ethyl-1H-pyrazolo[3,4-b]pyridine-5-carboxamide |
| 10 | 4-{[(1S)-1,2-Dimethylpropyl]amino}-1-ethyl-N-{1-[4-(methylsulfonyl)phenyl]ethyl}-1H-pyrazolo[3,4-b]pyridine-5-carboxamide |
| 11 | 4-{[(1S)-1,2-Dimethylpropyl]amino}-1-ethyl-N-[(6-methoxypyridin-3-yl)methyl]-1H-pyrazolo[3,4-b]pyridine-5-carboxamide |
| 12 | 4-{[(1S)-1,2-Dimethylpropyl]amino}-1-ethyl-N-{3-[(methylamino)carbonyl]benzyl}-1H-pyrazolo[3,4-b]pyridine-5-carboxamide |
| 13 | 4-{[(1S)-1,2-Dimethylpropyl]amino}-1-ethyl-N-[(1R)-1-phenylpropyl]-1H-pyrazolo[3,4-b]pyridine-5-carboxamide |
| 14 | 4-{[(1S)-1,2-Dimethylpropyl]amino}-N-(2,2-diphenylethyl)-1-ethyl-1H-pyrazolo[3,4-b]pyridine-5-carboxamide |
| 15 | N-[2-(Dimethylamino)benzyl]-4-{[(1S)-1,2-dimethylpropyl]amino}-1-ethyl-1H-pyrazolo[3,4-b]pyridine-5-carboxamide |
| 16 | 4-{[(1S)-1,2-Dimethylpropyl]amino}-1-ethyl-N-(4-fluorobenzyl)-1H-pyrazolo[3,4-b]pyridine-5-carboxamide |
| 17 | 4-{[(1S)-1,2-Dimethylpropyl]amino}-N-(diphenylmethyl)-1-ethyl-1H-pyrazolo[3,4-b]pyridine-5-carboxamide |
| 18 | 4-{[(1S)-1,2-Dimethylpropyl]amino}-1-ethyl-N-{4-[(methylamino)carbonyl]benzyl}-1H-pyrazolo[3,4-b]pyridine-5-carboxamide |
| 19 | Methyl 4-({[(4-{[(1S)-1,2-dimethylpropyl]amino}-1-ethyl-1H-pyrazolo[3,4-b]pyridin-5-yl)carbonyl]amino}methyl)benzoate |
| 20 | 4-{[(1S)-1,2-Dimethylpropyl]amino}-1-ethyl-N-(4-methoxyphenyl)-1H-pyrazolo[3,4-b]pyridine-5-carboxamide |
| 21 | 4-{[(1S)-1,2-Dimethylpropyl]amino}-1-ethyl-N-(4-hydroxybenzyl)-1H-pyrazolo[3,4-b]pyridine-5-carboxamide |
| 22 | 4-{[(1S)-1,2-Dimethylpropyl]amino}-1-ethyl-N-[3-(trifluoromethyl)benzyl]-1H-pyrazolo[3,4-b]pyridine-5-carboxamide |
| 23 | 4-{[(1S)-1,2-Dimethylpropyl]amino}-1-ethyl-N-(4-methoxybenzyl)-1H-pyrazolo[3,4-b]pyridine-5-carboxamide |
| 24 | N-(3,4-Difluorobenzyl)-4-{[(1S)-1,2-dimethylpropyl]amino}-1-ethyl-1H-pyrazolo[3,4-b]pyridine-5-carboxamide |
| 25 | N-(2,6-Difluorobenzyl)-4-{[(1S)-1,2-dimethylpropyl]amino}-1-ethyl-1H-pyrazolo[3,4-b]pyridine-5-carboxamide |
| 26 | 4-{[(1S)-1,2-Dimethylpropyl]amino}-1-ethyl-N-[(1R)-1-phenylethyl]-1H-pyrazolo[3,4-b]pyridine-5-carboxamide |
| 27 | N-(2,5-Difluorobenzyl)-4-{[(1S)-1,2-dimethylpropyl]amino}-1-ethyl-1H-pyrazolo[3,4-b]pyridine-5-carboxamide |
| 28 | 4-{[(1S)-1,2-Dimethylpropyl]amino}-1-ethyl-N-(3-fluorobenzyl)-1H-pyrazolo[3,4-b]pyridine-5-carboxamide |

| Example Number | Name |
|---|---|
| 29 | 4-{[(1S)-1,2-Dimethylpropyl]amino}-1-ethyl-N-[2-(trifluoromethyl)benzyl]-1H-pyrazolo[3,4-b]pyridine-5-carboxamide |
| 30 | N-(5-Chloro-2,3-dihydro-1H-inden-2-yl)-4-{[(1S)-1,2-dimethylpropyl]amino}-1-ethyl-1H-pyrazolo[3,4-b]pyridine-5-carboxamide |
| 31 | Methyl 3-({[(4-{[(1S)-1,2-dimethylpropyl]amino}-1-ethyl-1H-pyrazolo[3,4-b]pyridin-5-yl)carbonyl]amino}methyl)benzoate |
| 32 | N-[2-(Aminocarbonyl)benzyl]-4-{[(1S)-1,2-dimethylpropyl]amino}-1-ethyl-1H-pyrazolo[3,4-b]pyridine-5-carboxamide |
| 33 | 4-{[(1S)-1,2-Dimethylpropyl]amino}-1-ethyl-N-{4-[(methylsulfonyl)amino]benzyl}-1H-pyrazolo[3,4-b]pyridine-5-carboxamide |
| 34 | 4-{[(1S)-1,2-Dimethylpropyl]amino}-1-ethyl-N-{3-[(methylsulfonyl)amino]benzyl}-1H-pyrazolo[3,4-b]pyridine-5-carboxamide |
| 35 | 4-{[(1S)-1,2-Dimethylpropyl]amino}-1-ethyl-N-[4-(trifluoromethyl)benzyl]-1H-pyrazolo[3,4-b]pyridine-5-carboxamide |
| 36 | N-(2,3-Dihydro-1H-inden-2-yl)-4-{[(1S)-1,2-dimethylpropyl]amino}-1-ethyl-1H-pyrazolo[3,4-b]pyridine-5-carboxamide |
| 37 | 4-{[(1S)-1,2-Dimethylpropyl]amino}-1-ethyl-N-[4-(methylsulfonyl)benzyl]-1H-pyrazolo[3,4-b]pyridine-5-carboxamide |
| 38 | N-Benzyl-4-{[(1S)-1,2-dimethylpropyl]amino}-1-ethyl-1H-pyrazolo[3,4-b]pyridine-5-carboxamide |
| 39 | 4-{[(1S)-1,2-Dimethylpropyl]amino}-1-ethyl-N-(4-fluorophenyl)-1H-pyrazolo[3,4-b]pyridine-5-carboxamide |
| 40 | N-[2-(Aminosulfonyl)ethyl]-4-{[(1S)-1,2-dimethylpropyl]amino}-1-ethyl-1H-pyrazolo[3,4-b]pyridine-5-carboxamide |
| 41 | 4-{[(1S)-1,2-Dimethylpropyl]amino}-1-ethyl-N-[(6-oxo-1,6-dihydropyridin-3-yl)methyl]-1H-pyrazolo[3,4-b]pyridine-5-carboxamide |
| 42 | 4-{[(1S)-1,2-Dimethylpropyl]amino}-1-ethyl-N-{2-[(methylsulfonyl)amino]ethyl}-1H-pyrazolo[3,4-b]pyridine-5-carboxamide |
| 43 | 4-{[(1S)-1,2-Dimethylpropyl]amino}-1-ethyl-N-(tetrahydro-2H-pyran-4-yl)-1H-pyrazolo[3,4-b]pyridine-5-carboxamide |
| 44 | 4-{[(1S)-1,2-Dimethylpropyl]amino}-1-ethyl-N-[(1-methyl-1H-pyrazol-4-yl)methyl]-1H-pyrazolo[3,4-b]pyridine-5-carboxamide |
| 45 | 4-{[(1S)-1,2-Dimethylpropyl]amino}-1-ethyl-N-[3-(methylsulfonyl)benzyl]-1H-pyrazolo[3,4-b]pyridine-5-carboxamide |
| 46 | 4-{[(1S)-1,2-Dimethylpropyl]amino}-1-ethyl-N-(pyridin-3-ylmethyl)-1H-pyrazolo[3,4-b]pyridine-5-carboxamide |
| 47 | N-[3-(Aminocarbonyl)benzyl]-4-{[(1S)-1,2-dimethylpropyl]amino}-1-ethyl-1H-pyrazolo[3,4-b]pyridine-5-carboxamide |
| 48 | 4-{[(1S)-1,2-Dimethylpropyl]amino}-1-ethyl-N-(tetrahydrofuran-2-ylmethyl)-1H-pyrazolo[3,4-b]pyridine-5-carboxamide |
| 49 | N-{4-[(Dimethylamino)sulfonyl]benzyl}-4-{[(1S)-1,2-dimethylpropyl]amino}-1-ethyl-1H-pyrazolo[3,4-b]pyridine-5-carboxamide |
| 51 | 4-{[(1S)-1,2-Dimethylpropyl]amino}-1-ethyl-N-(2-ethylbutyl)-1H-pyrazolo[3,4-b]pyridine-5-carboxamide |
| 53 | 4-(tert-Butylamino)-1-ethyl-N-benzyl-1H-pyrazolo[3,4-b]pyridine-5-carboxamide |
| 54 | 4-(tert-Butylamino)-1-ethyl-N-(4-fluorophenyl)-1H-pyrazolo[3,4-b]pyridine-5-carboxamide |
| 55 | 4-(tert-Butylamino)-1-ethyl-N-[4-(trifluoromethyl)benzyl]-1H-pyrazolo[3,4-b]pyridine-5-carboxamide |
| 56 | 4-(tert-Butylamino)-N-(2,3-dihydro-1H-inden-2-yl)-1-ethyl-1H-pyrazolo[3,4-b]pyridine-5-carboxamide |
| 57 | 4-(tert-Butylamino)-1-ethyl-N-[4-(methylsulfonyl)benzyl]-1H-pyrazolo[3,4-b]pyridine-5-carboxamide |

Examples 1 to 5

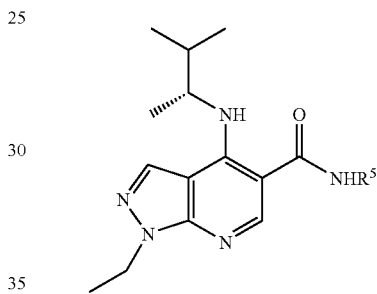

General Procedure

A mixture of Intermediate 4 (0.0675 mmol), HATU (0.0675 mmol) and DIPEA (0.203 mmol) in DMF (0.5 ml) was shaken intermittently at room temperature for 10 min. A solution of the amine $R^5NH_2$ (0.074 mmol) in DMF (0.4 ml) was then added and the mixture was stirred at room temperature. After 16 hours, volatiles were removed in a vacuum centrifuge. The residue was dissolved in chloroform (0.5 ml) and applied to a SPE cartridge (aminopropyl, 0.5 g). The cartridge was eluted successively with chloroform (1.5 ml) and EtOAc (1.5 ml). The fraction containing the desired product was concentrated in vacuo to afford the pure product.

| Example no. | NHR⁵ (connecting point underlined) | Source of Amine $R^5NH_2$ | MH+ ion | LC-MS Retention time (min) |
|---|---|---|---|---|
| 1 | benzyl-NH | Aldrich | 366 | 3.04 |
| 2 | 4-F-phenyl-NH | Aldrich | 370 | 3.31 |

-continued

| Example no. | NHR⁵ (connecting point underlined) | Source of Amine R⁵NH₂ | MH+ ion | LC-MS Retention time (min) |
|---|---|---|---|---|
| 3 | 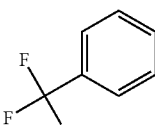 | Aldrich; or Meindl et al., J. Med. Chem., 1984, 27(9), 1111; or Org. Lett., 2002, 4(12), 2055 | 434 | 3.38 |
| 4 | 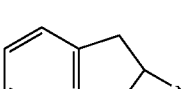 | TCI-America; or Aldrich; or Maybridge-Int | 392 | 3.19 |
| 5 | 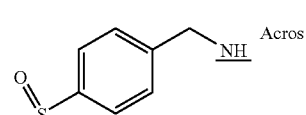 | Acros | 444 | 2.77 |

Examples 6 to 34

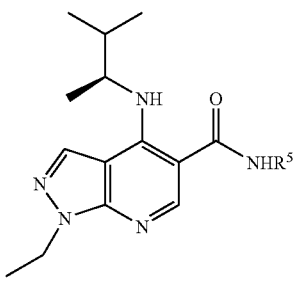

General Procedure

A mixture of Intermediate 5 (0.1 mmol), HATU (0.1 mmol) and DIPEA (0.4 mmol) in DMF (0.4 ml) was shaken at room temperature for 10 min. A solution of the amine R⁵NH₂ (0.1 mmol) in DMF (0.2 ml) was then added and the mixture agitated for several minutes to give a solution. The solution was stored at room temperature for 16 hours then concentrated in vacuo. The residue was dissolved in chloroform (0.5 ml) and applied to a SPE cartridge (aminopropyl, 0.5 g). The cartridge was eluted successively with chloroform (1.5 ml), EtOAc (1.5 ml) and EtOAc:MeOH (9:1, 1.5 ml). Fractions containing the desired product were concentrated in vacuo and the residue purified by mass directed autoprep HPLC.

| Example no. | NHR⁵ (connecting point underlined) | Source of Amine R⁵NH₂ | MH+ ion | LC-MS Retention time (min) |
|---|---|---|---|---|
| 6 | 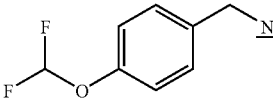 | Fluorochem Ltd; Apollo or WO 98/45268 | 432 | 3.54 |
| 7 | 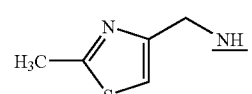 | MicroChemistry-RadaPharma | 387 | 3.04 |
| 8 | 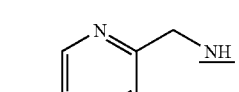 | Key Organics Ltd | 401 | 3.27 |
| 9 | 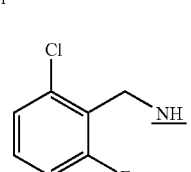 | Fluka | 418 | 3.6 |

-continued
| Example no. | NHR⁵ (connecting point underlined) | Source of Amine R⁵NH₂ | MH+ ion | LC-MS Retention time (min) |
|---|---|---|---|---|
| 10 | 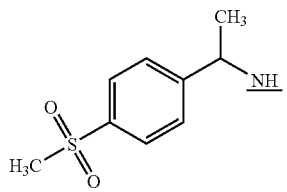 | Peakdale Molecular Ltd | 458 | 3.15 |
| 11 | 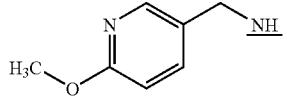 | WO 00/17163 | 397 | 3.19 |
| 12 | 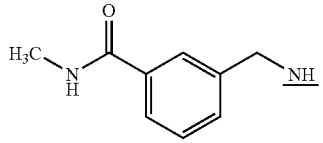 | Peakdale Molecular Ltd | 423 | 2.97 |
| 13 | 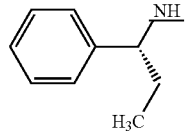 | Lancaster Synthesis Ltd | 394 | 3.62 |
| 14 | 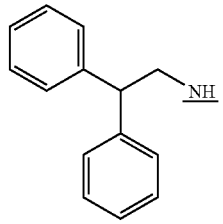 | Salor | 456 | 3.8 |
| 15 | 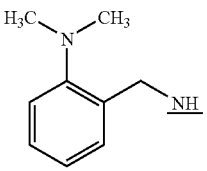 | J. Org. Chem., 2001, 66(6), 1999 | 409 | 2.81 |
| 16 | 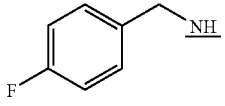 | Aldrich | 384 | 349 |
| 17 | 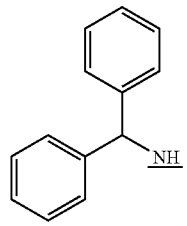 | Aldrich | 442 | 3.78 |

-continued
| Example no. | NHR⁵ (connecting point underlined) | Source of Amine R⁵NH₂ | MH+ ion | LC-MS Retention time (min) |
|---|---|---|---|---|
| 18 | 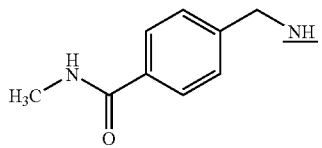 | WO 94/17035 | 423 | 2.94 |
| 19 | 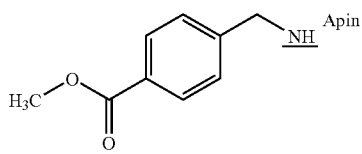 | Apin | 424 | 3.41 |
| 20 | 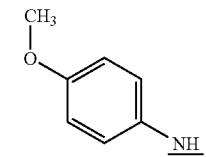 | Aldrich | 382 | 3.48 |
| 21 | 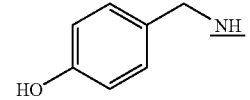 | Apin | 382 | 3.13 |
| 22 | 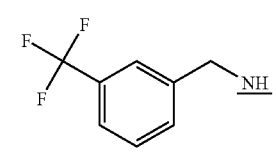 | Aldrich; or Meindl et al., J. Med. Chem., 1984, 27(9), 1111. | 434 | 3.7 |
| 23 | 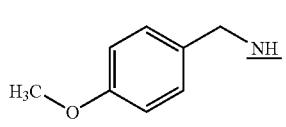 | Acros; or Aldrich; or Jung et al., Tetrahedron Lett., 2002, 43(48), 8735; or Meindl et al., J. Med. Chem., 1984, 27(9), 1111; or Org. Lett., 2002, 4, 2055 | 396 | 3.4 |
| 24 | 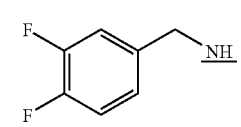 | Aldrich | 402 | 3.56 |
| 25 | 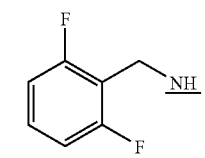 | Aldrich | 402 | 3.46 |
| 26 | 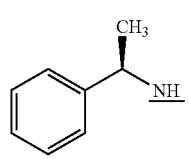 | Lancaster Synthesis Ltd | 380 | 3.5 |

-continued
| Example no. | NHR⁵ (connecting point underlined) | Source of Amine R⁵NH₂ | MH+ ion | LC-MS Retention time (min) |
|---|---|---|---|---|
| 27 | 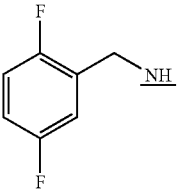 | Aldrich | 402 | 3.55 |
| 28 | 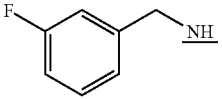 | Aldrich; or Meindl et al., J. Med. Chem., 1984, 27(9), 1111. | 384 | 3.5 |
| 29 | 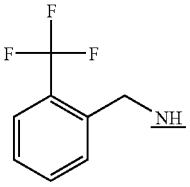 | Aldrich | 434 | 3.71 |
| 30 | 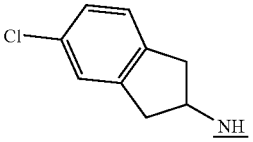 | J. Med. Chem., 2001, 44(26), 4628 | 426 | 3.84 |
| 31 | 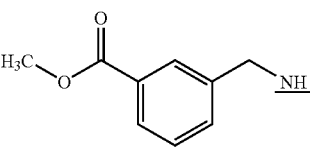 | Peakdale Molecular Ltd | 424 | 3.41 |
| 32 | 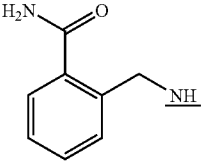 | J. Am. Chem. Soc., 1977, 99, 3075 | 409 | 2.94 |
| 33 | 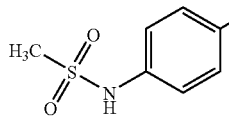 | Lis et al., J. Med. Chem., 1990, 33(10), 2883, see Scheme III and ref. 24 | 459 | 3.11 |
| 34 | 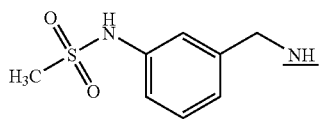 | J. Med. Chem., 1999, 42(14), 2504 | 459 | 3.13 |

Examples 35 to 39

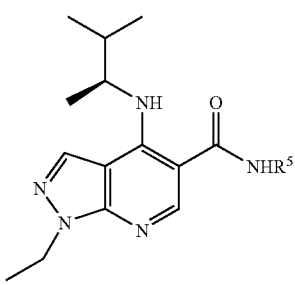

General Procedure

A mixture of Intermediate 5 (0.0675 mmol), HATU (0.0675 mmol) and DIPEA (0.203 mmol) in DMF (0.5 ml) was shaken intermittently at room temperature for 10 min. A solution of the amine $R^5NH_2$ (0.074 mmol) in DMF (0.4 ml) was then added and the mixture was stirred at room temperature. After 16 hours, volatiles were removed in a vacuum centrifuge. The residue was dissolved in chloroform (0.5 ml) and applied to a SPE cartridge (aminopropyl, 0.5 g). The cartridge was eluted successively with chloroform (1.5 ml) and EtOAc (1.5 ml). The fraction containing the desired product was concentrated in vacuo to afford the pure product.

Examples 40 to 49

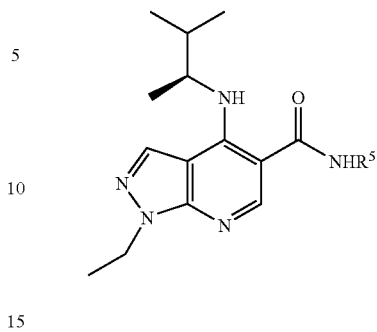

General Procedure

A mixture of Intermediate 5 (0.0675 mmol), HATU (0.0675 mmol) and DIPEA (0.203 mmol) in DMF (0.5 ml) was shaken intermittently at room temperature for 15 min. A solution of the amine $R^5NH_2$ (0.074 mmol) in DMF (0.4 ml) was then added and the mixture was stirred at room temperature. After 16 hours, volatiles were removed in a vacuum centrifuge. The residue was dissolved in chloroform (0.5 ml) and applied to a SPE cartridge (aminopropyl, 0.5 g). The cartridge was eluted successively with chloroform (1.5 ml), ethyl acetate-methanol (9:1, 1.5 ml) and methanol (1.5 ml). The fraction containing the desired product was concentrated in vacuo to afford the pure product.

| Example no. | $NHR^5$ (connecting point underlined) | Source of Amine $R^5NH_2$ | MH+ ion | LC-MS Retention time (min) |
|---|---|---|---|---|
| 35 | 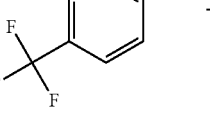 | Aldrich; or Meindl et al., J. Med. Chem., 1984, 27(9), 1111; or Org. Lett., 2002, 4(12), 2055 | 434 | 3.38 |
| 36 | 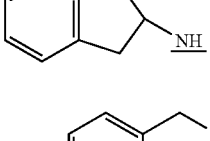 | TCI-America; or Aldrich; or Maybridge-Int | 392 | 3.19 |
| 37 | 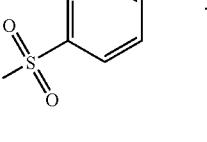 | Acros | 444 | 2.77 |
| 38 | 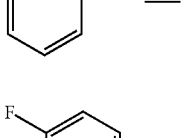 | Aldrich | 366 | 3.05 |
| 39 | 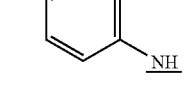 | Aldrich | 370 | 3.31 |

| Example no. | NHR⁵ (connecting point underlined) | Source of Amine R⁵NH₂ | MH+ ion | LC-MS Retention time (min) |
|---|---|---|---|---|
| 40 | 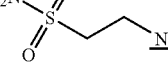 | Rare Chemicals GmbH | 383 | 2.71 |
| 41 | 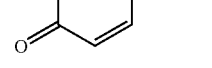 | MicroChemistry-RadaPharma | 383 | 2.68 |
| 42 | 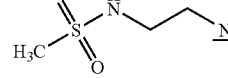 | Ultrafine(UFC Ltd) | 397 | 2.75 |
| 43 |  | Combi-Blocks | 360 | 2.92 |
| 44 |  | N.D. Zelinsky Institute Organic Chemistry | 370 | 2.85 |
| 45 | 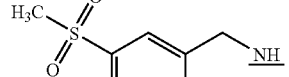 | Peakdale Molecular Ltd. | 444 | 3.13 |
| 46 | 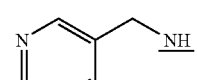 | Aldrich | 367 | 2.60 |
| 47 |  | Peakdale Molecular Ltd. | 409 | 2.92 |
| 48 | 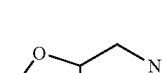 | Aldrich | 360 | 2.99 |
| 49 |  | J. Org. Chem., 1955, 20, 1657 | 473 | 3.35 |

Example 51

4-{[(1S)-1,2-Dimethylpropyl]amino}-1-ethyl-N-(2-ethylbutyl)-1H-pyrazolo[3,4-b]pyridine-5-carboxamide

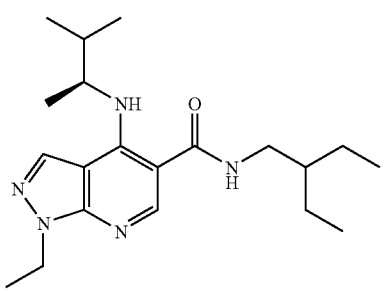

A mixture of Intermediate 5 (0.5 mmol), EDC (0.7 mmol) and DIPEA (0.5 mmol) in DMF (5 ml) was stirred at room temperature for 30 min. 2-Ethyl-n-butylamine (0.55 mmol) was then added, followed by DIPEA (0.5 mmol) and the mixture stirred for a further 18 hours. The solution was stored at room temperature for 48 hours then applied directly to a SPE cartridge (aminopropyl, 5 g) which was eluted with methanol. Fractions containing the desired product were concentrated in vacuo and the residue purified by chromatography using Biotage (silica, 10 g) eluting with a gradient of 10-100% ethyl acetate in cyclohexane to afford Example 51 (0.07 g) as a colourless oil. LCMS showed MH$^+$ 360; T$_{RET}$=3.61 min.

Examples 53 to 57

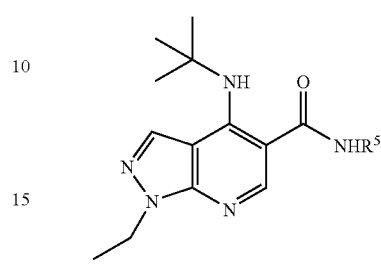

General Procedure

A mixture of Intermediate 7 (0.0675 mmol), HATU (0.0675 mmol) and DIPEA (0.203 mmol) in DMF (0.5 ml) was shaken intermittently at room temperature for 10 min. A solution of the amine R$^5$NH$_2$ (0.074 mmol) in DMF (0.4 ml) was then added and the mixture was stirred at room temperature. After 16 hours, volatiles were removed in a vacuum centrifuge. The residue was dissolved in chloroform (0.5 ml) and applied to a SPE cartridge (aminopropyl, 0.5 g). The cartridge was eluted successively with chloroform (1.5 ml) and EtOAc (1.5 ml). The fraction containing the desired product was concentrated in vacuo to afford the pure product.

| Example no. | NHR$^5$ (connecting point underlined) | Source of Amine R$^5$NH$_2$ | MH+ ion | LC-MS Retention time (min) |
|---|---|---|---|---|
| 53 | benzyl-NH | Aldrich | 352 | 2.89 |
| 54 | 4-fluorophenyl-NH | Aldrich | 356 | 3.14 |
| 55 | 4-(trifluoromethyl)benzyl-NH | Aldrich; or Meindl et al., J. Med. Chem., 1984, 27(9), 1111; or Org. Lett., 2002, 4(12), 2055 | 420 | 3.26 |
| 56 | indan-2-yl-NH | TCI-America; or Aldrich; or Maybridge-Int | 378 | 3.03 |
| 57 | 4-(methylsulfonyl)benzyl-NH | Acros | 430 | 2.63 |

Comparative Examples 58 to 60

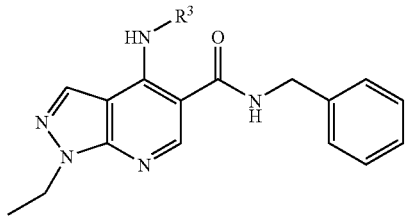

General Procedure

The amine $R^3NH_2$ (0.2 mmol) was added to a stirred solution of Intermediate 10 (0.1 mmol) and diisopropylethylamine (0.5 mmol) in acetonitrile (2 ml), and the resulting mixture was heated at 85° C. After 3 days at 85° C., the reaction mixture was concentrated in vacuo and the residue was distributed between dichloromethane (4 ml) and water (1 ml). The phases were separated by passage through a hydrophobic frit and the organic phase was evaporated to a yellow oil which was purified on a SPE cartridge (silica, 2 g) eluting with a gradient of ethyl acetate-cyclohexane (12.5-100%) to afford the pure product.

| Comparative Example no. | NHR³ (connecting point underlined) | Source of Amine R³NH₂ | MH+ ion | LC-MS Retention time (min) |
|---|---|---|---|---|
| 58 | | Aldrich | 352 | 3.19 |
| 59 | | Aldrich | 352 | 3.2 |
| 60 | | Aldrich | 352 | 3.2 |

Comparative Examples 60 and 61

Comparative Example 60

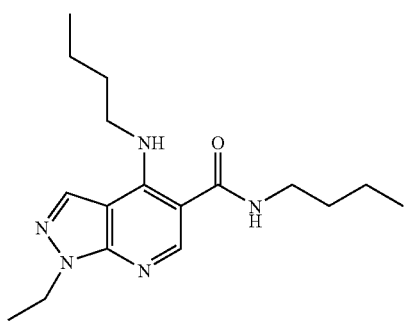

-continued

Comparative Example 61

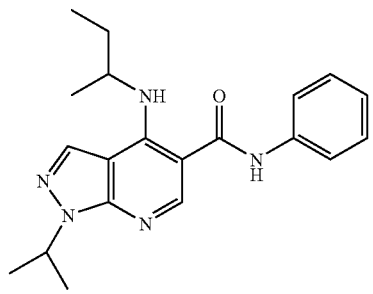

Comparative Example 60 is the free base version of Example 1 of U.S. Pat. No. 3,979,399 (E.R. Squibb & Sons).

Comparative Example 61 is the same as Example 19 of U.S. Pat. No. 3,979,399 (E.R. Squibb & Sons).

They can optionally be made according to the methods disclosed in U.S. Pat. No. 3,979,399.

The invention claimed is:

1. A compound of formula (I) or a salt thereof:

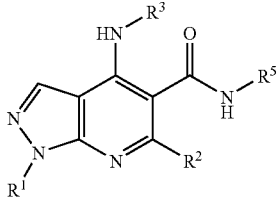

(I)

wherein:
$R^1$ is ethyl, n-propyl, isopropyl, $C_{1-2}$fluoroalkyl, or —$CH_2CH_2OH$;
$R^2$ is hydrogen, methyl, ethyl, n-propyl, isopropyl, $C_{1-2}$fluoroalkyl, cyclopropyl or (cyclopropyl)methyl-;
$NHR^3$ has the sub-formula (nhr3):

(nhr3)

wherein, in sub-formula (nhr3), the —NH— connection point of the $NHR^3$ group to the bicyclic ring system of formula (I) is underlined, and wherein
$R^{3a}$ is methyl or ethyl;
$R^{3b}$ is hydrogen, methyl or ethyl,
$R^{3c}$ is hydrogen, methyl or ethyl,
$R^{3d}$ is hydrogen, methyl or ethyl, and
$R^{3e}$ is hydrogen or methyl,
provided that:
(a) $R^{3b}$ is methyl or ethyl; and (b) $R^{3c}$ and $R^{3d}$ are independently methyl or ethyl;
and provided that:
(c) when $R^{3c}$ is ethyl and when $R^{3d}$ is ethyl and when $R^{3e}$ is methyl, then: $R^{3a}$ is methyl and $R^{3b}$ is hydrogen or methyl;

and wherein:

$R^5$ is $C_{3-8}$alkyl; $C_{3-8}$cycloalkyl optionally substituted by a $C_{1-2}$alkyl group; or —$(CH_2)_{n^4}$—$C_{3-8}$cycloalkyl optionally substituted, in the —$(CH_2)_{n^4}$- moiety or in the $C_{3-8}$cycloalkyl moiety, by a $C_{1-2}$alkyl group, wherein $n^4$ is 1, 2 or 3;

or $R^5$ is $C_{2-6}$alkyl substituted by one or two independent substituents $R^{11}$; wherein each substituent $R^{11}$, independently of any other $R^{11}$ substituent present, is: hydroxy; $C_{1-6}$alkoxy; phenyloxy; benzyloxy; —$NR^{12}R^{13}$; —$NR^{15}$—$C(O)R^{16}$; —$NR^{15}$—$C(O)$—$NH$—$R^{15}$; or —$NR^{15}$—$SO_2R^{16}$; and wherein any $R^{11}$ substituent which is OH, alkoxy or —$NR^{12}R^{13}$ is not substituted at the carbon atom, of any $R^5$ substituted alkyl, which is bonded to the nitrogen of $NHR^5$;

or $R^5$ is —$(CH_2)_{n^{12}}$—$SO_2$—$NR^{12}R^{13}$ or —$(CH_2)_{n^{12}}$—$SO_2R^{16}$; wherein $n^{12}$ is 2, 3 or 4;

or $R^5$ is —$(CH_2)_{n^{13}}$-Het wherein $n^{13}$ is 0, 1, 2, 3 or 4 and Het is a 4-, 5-, 6- or 7-membered saturated or partly-saturated heterocyclic ring containing one or two ring-hetero-atoms independently selected from O, S, and N; wherein any ring-hetero-atoms present are not bound to the —$(CH_2)_{n^{13}}$- moiety when $n^{13}$ is 1 and are not bound to the nitrogen of $NHR^5$ when $n^{13}$ is 0; wherein any ring-nitrogens which are present and which are saturated are present as $NR^{17}$; and wherein one or two of the carbon ring-atoms independently are optionally substituted by $C_{1-2}$alkyl;

or $R^5$ has the sub-formula (x), (xa), (y), (y1), (z) or (za):

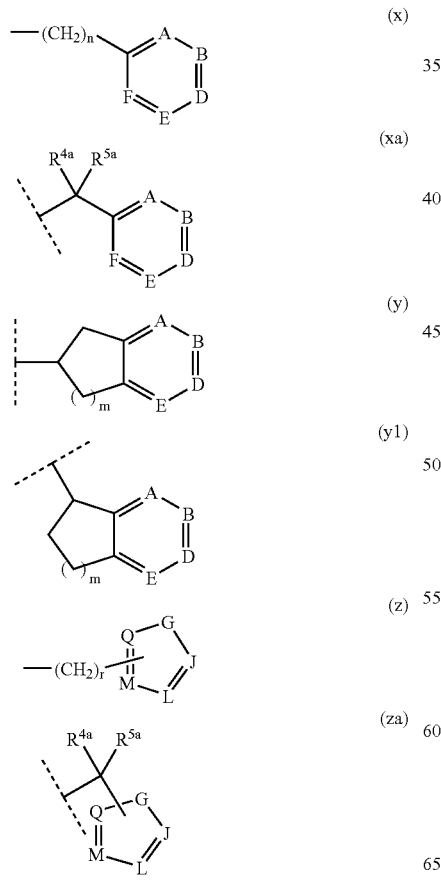

wherein in sub-formula (x), n=0, 1 or 2; in sub-formula (y) and (y1), m=1 or 2; and in sub-formula (z), r=0, 1 or 2;

wherein sub-formula (y) and (y1), independently, are optionally substituted by oxo at a ring carbon adjacent the 6-membered aromatic ring;

and wherein, in sub-formula (xa) and (za):

$R^{4a}$ is hydrogen; methyl, ethyl, n-propyl, isopropyl, $C_{1-2}$fluoroalkyl, cyclopropyl, —$CH_2OR^{4aa}$, —$CH(Me)OR^{4aa}$, or —$CH_2CH_2OR^{4aa}$, wherein $R^{4aa}$ is hydrogen, methyl, or $C_1$fluoroalkyl; and $R^{5a}$ is-hydrogen; $C_{1-8}$alkyl; $C_{1-3}$fluoroalkyl; $C_{3-8}$cycloalkyl optionally substituted by a $C_{1-2}$alkyl group; or —$(CH_2)_{n^{4a}}$—$C_{3-8}$cycloalkyl optionally substituted, in the —$(CH_2)_{n^{4a}}$- moiety or in the $C_{3-8}$-cycloalkyl moiety, by a $C_{1-2}$alkyl group, wherein $n^{4a}$ is 1 or 2;

or $R^{5a}$ is $C_{1-4}$alkyl substituted by one substituent $R^{11a}$; wherein $R^{11a}$ is: hydroxy (OH); $C_{1-6}$alkoxy; $C_{1-2}$fluoroalkoxy; phenyloxy; (monofluoro- or difluoro-phenyl)oxy; (monomethyl- or dimethyl-phenyl)oxy; benzyloxy; —$NR^{12}R^{13}$; —$NR^{15}$—$C(O)R^{16}$; —$NR^{15}$—$C(O)$—$NH$—$R^{15}$; or —$NR^{15}$—$S(O)_2R^{16}$;

or $R^{5a}$ is $C_{2-4}$alkyl substituted on different carbon atoms by two hydroxy substituents;

or $R^{5a}$ is —$(CH_2)_{n^{11a}}$—$C(O)R^{16}$; —$(CH_2)_{n^{11a}}$—$C(O)NR^{12}R^{13}$; —$CHR^{19a}$—$C(O)NR^{12}R^{13}$; —$(CH_2)_{n^{11a}}$—$C(O)OR^{16}$; —$(CH_2)_{n^{11a}}$—$C(O)OH$; —$CHR^{19a}$—$C(O)OR^{16}$; —$CHR^{19a}$—$C(O)OH$; —$(CH_2)_{n^{11a}}$—$S(O)_2$—$NR^{12}R^{13}$; —$(CH_2)_{n^{11a}}$—$S(O)_2R^{16}$; or —$(CH_2)_{n^{11a}}$—CN; wherein $n^{11a}$ is 0, 1, 2 or 3 wherein for each $R^{5a}$ group $n^{11a}$ is independent of the value of $n^{11a}$ in other $R^{5a}$ groups; and wherein $R^{19a}$ is $C_{1-2}$alkyl;

or $R^{5a}$ is —$(CH_2)_{n^{13a}}$-$Het^A$, wherein $n^{13a}$ is 0, 1 or 2 and $Het^A$ is a 4-, 5-, 6- or 7-membered saturated or unsaturated heterocyclic ring, other than —$NR^{12}R^{13}$, containing one or two ring-hetero-atoms independently selected from O, S, and N; wherein any ring-hetero-atoms present are not bound to the —$(CH_2)_{n^{13a}}$ moiety when $n^{13a}$ is 0; wherein any ring-nitrogens which are present and which are saturated and which are not connecting nitrogens are present as $NR^{17a}$; and wherein one or two of the carbon ring-atoms are independently optionally substituted by $C_{1-2}$alkyl;

or $R^{5a}$ is phenyl, —$CH_2$-Ph, —CHMe-Ph, —CHEt-Ph, $CMe_2$Ph, or —$CH_2CH_2$-Ph, wherein the phenyl ring is optionally substituted with one or two substituents independently selected from the group consisting of a halogen atom; $C_{1-4}$alkyl; $C_{1-2}$fluoroalkyl; $C_{1-4}$alkoxy; $C_{1-2}$fluoroalkoxy; cyclopropyl; cyclopropyloxy; —$C(O)$—$C_{1-4}$alkyl; —$C(O)OH$; —$C(O)$—$OC_{1-4}$alkyl; $C_{1-4}$alkyl-$S(O)_2$—; $C_{1-4}$alkyl-$S(O)_2$—$NR^{8a}$—; $R^{7a}R^{8a}N$—$S(O)_2$—; $R^{7a}R^{8a}N$—$C(O)$—; —$NR^{8a}$—$C(O)$—$C_{1-4}$alkyl; $R^{7a}R^{8a}N$; OH; nitro (—$NO_2$); and cyano (—CN);

or $R^{4a}$ and $R^{5a}$ taken together are —$(CH_2)_{p^1}$— or —$(CH_2)_{p^3}$—$X^5$—$(CH_2)_{p^4}$—, in which: $X^5$ is O or $NR^{17a}$; $p^1$=2, 3, 4, 5 or 6, and $p^3$ and $p^4$ independently are 1, 2 or 3 provided that if $p^3$ is 3 then $p^4$ is 1 or 2 and if $p^4$ is 3 then $p^3$ is 1 or 2;

provided that at least one of $R^{4a}$ and $R^{5a}$ is not hydrogen;

and wherein, in sub-formula (x) and in sub-formula (xa):

A is C—$R^{6A}$, nitrogen or nitrogen-oxide,

B is C—$R^{6B}$, nitrogen or nitrogen-oxide,

D is C—$R^{6D}$, nitrogen or nitrogen-oxide,

E is C—$R^{6E}$, nitrogen or nitrogen-oxide,

F is C—$R^{6F}$, nitrogen or nitrogen-oxide, wherein, $R^{6A}$, $R^{6B}$, $R^{6D}$, $R^{6E}$ and $R^{6F}$ independently are: hydrogen, a halogen atom; $C_{1-6}$alkyl; $C_{1-4}$fluoroalkyl; $C_{3-6}$cycloalkyl; $C_{1-4}$alkoxy; $C_{1-2}$fluoroalkoxy; $C_{3-6}$cycloalkyloxy; —C(O)$R^{16a}$; —C(O)O$R^{30}$; —S(O)$_2$—$R^{16a}$; $R^{16a}$—S(O)$_2$—N$R^{15a}$—; $R^7R^8$N—S(O)$_2$—; $C_{1-2}$alkyl-C(O)—$R^{15a}$N—S(O)$_2$—; $C_{1-2}$alkyl-S(O)—, Ph-S(O)—, $R^7R^8$N—CO—; —N$R^{15a}$—C(O)$R^{16a}$; $R^7R^8$N; nitro; OH; $C_{1-4}$alkoxymethyl; $C_{1-4}$alkoxyethyl; $C_{1-2}$alkyl-S(O)$_2$—CH$_2$—; $R^7R^8$N—S(O)$_2$—CH$_2$—; $C_{1-2}$alkyl-S(O)$_2$—N$R^{15a}$—CH$_2$—; —CH$_2$—OH; —CH$_2$CH$_2$—OH; —CH$_2$—N$R^7R^8$; —CH$_2$—CH$_2$—N$R^7R^8$; —CH$_2$—C(O)O$R^{30}$; —CH$_2$—C(O)—N$R^7R^8$; —CH$_2$—N$R^{15a}$—C(O)—$C_{1-3}$alkyl; —(CH$_2$)$_n^{14}$-Het$^1$ where $n^{14}$ is 0 or 1; cyano; Ar$^{5b}$; or phenyl, pyridinyl or pyrimidinyl wherein the phenyl, pyridinyl or pyrimidinyl independently are optionally substituted by one or two substituents selected from the group consisting of fluoro, chloro, $C_{1-2}$alkyl, $C_1$fluoroalkyl, $C_{1-2}$alkoxy and $C_1$fluoroalkoxy;

and two adjacent groups are selected from the group consisting of $R^{6A}$, $R^{6B}$, $R^{6D}$, $R^{6E}$ and $R^{6F}$, and are: —CH═CH—CH═CH$_2$—, —(CH$_2$)$_n^{14a}$— where $n^{14a}$ is 3, 4 or 5, —O—(CMe$_2$)—O—, —O—(CH$_2$)$_n^{14b}$—O— where $n^{14b}$ is 1 or 2; —CH═CH—N$R^{15b}$—; —N═CH—N$R^{15b}$—; —CH═N—N$R^{15b}$—; —N═N—N$R^{15b}$—; —CH═CH—O—; —N═CH—O—; —CH═CH—S—; or —N═CH—S—; wherein $R^{15b}$ is H or $C_{1-2}$alkyl;

provided that:

at least two of A, B, D, E and F are independently C—H, C—F, nitrogen, or nitrogen-oxide;

and no more than two of A, B, D, E and F are independently nitrogen or nitrogen-oxide, and no more than one of A, B, D, E and F is nitrogen-oxide;

and wherein, in sub-formula (z) and in sub-formula (za):

G is O or S or N$R^9$ wherein $R^9$ is hydrogen, $C_{1-4}$alkyl, or $C_{1-2}$fluoroalkyl;

J is C—$R^{6J}$, C-[connection point to formula (I)], or nitrogen,

L is C—$R^{6L}$, C-[connection point to formula (I)], or nitrogen,

M is C—$R^{6M}$, C-[connection point to formula (I)], or nitrogen,

Q is C—$R^{6Q}$, C-[connection point to formula (I)], or nitrogen, wherein, $R^{6J}$, $R^{6L}$, $R^{6M}$ and $R^{6Q}$ independently are:-hydrogen, a halogen atom; $C_{1-4}$alkyl; $C_{1-3}$fluoroalkyl; $C_{3-6}$cycloalkyl; $C_{1-4}$alkoxy; $C_{1-2}$fluoroalkoxy; $C_{3-6}$cycloalkyloxy; OH (including any tautomer thereof); or phenyl optionally substituted by one or two substituents independently selected from the group consisting of fluoro, chloro, $C_{1-2}$alkyl, $C_1$fluoroalkyl, $C_{1-2}$alkoxy and $C_1$fluoroalkoxy;

provided that:

at least two of J, L, M and Q are independently C—H, C—F, C—$C_{1-2}$alkyl, C-[connection point to formula (I)], or nitrogen;

and no more than three of J, L, M and Q are nitrogen;

and wherein:

$R^7$ and $R^8$ are independently hydrogen; $C_{1-4}$alkyl; $C_{3-6}$cycloalkyl; or phenyl optionally substituted by one or two substituents independently selected from the group consisting of: fluoro, chloro, $C_{1-2}$alkyl, $C_1$fluoroalkyl, $C_{1-2}$alkoxy and $C_1$fluoroalkoxy;

or $R^7$ and $R^8$ together are —(CH$_2$)$_n^6$— or —C(O)—(CH$_2$)$_n^7$— or —C(O)—(CH$_2$)$_n^{10}$—C(O)— or —(CH$_2$)$_n^8$—X$^7$—(CH$_2$)$_n^9$— or —C(O)—X$^7$—(CH$_2$)$_n^{10}$ in which: $n^6$ is 3, 4, 5 or 6, $n^7$ is 2, 3, 4, or 5, $n^8$ and $n^9$ and $n^{10}$ independently are 2 or 3, and $X^7$ is O or N$R^{14}$;

$R^{7a}$ is hydrogen or $C_{1-4}$alkyl;

$R^{8a}$ is hydrogen or methyl;

$R^{12}$ and $R^{13}$, independent of any other $R^{12}$ or $R^{13}$ independently are: H; $C_{1-4}$alkyl; $C_{3-6}$cycloalkyl; or phenyl optionally substituted by one or two substituents independently selected from the group consisting of fluoro, chloro, $C_{1-2}$alkyl, $C_1$fluoroalkyl, $C_{1-2}$alkoxy and $C_1$fluoroalkoxy;

or $R^{12}$ and $R^{13}$, independent of any other $R^{12}$ or $R^{13}$, together are —(CH$_2$)$_n^{6a}$— or —C(O)—(CH$_2$)$_n^{7a}$— or —C(O)—(CH$_2$)$_n^{10a}$—C(O)— or —(CH$_2$)$_n^{8a}$—X$^{12}$—(CH$_2$)$_n^{9a}$— or —C(O)—X$^{12}$—(CH$_2$)$_n^{10a}$— in which: $n^{6a}$ is 3, 4, 5 or 6, $n^{7a}$ is 2, 3, 4, or 5, $n^{8a}$ and $n^{9a}$ and $n^{10a}$ independently are 2 or 3 and $X^{12}$ is O or N$R^{14a}$;

$R^{14}$, $R^{14a}$ and $R^{17a}$, independent of any other $R^{14}$, $R^{14a}$ or $R^{17a}$, independently are: hydrogen; $C_{1-4}$alkyl; $C_{1-2}$fluoroalkyl; cyclopropyl; —C(O)—$C_{1-14}$alkyl; —C(O)N$R^{7a}R^{8a}$; or —S(O)$_2$—$C_{1-4}$alkyl;

$R^{15}$, independent of any other $R^{15}$, is hydrogen; $C_{1-4}$alkyl; $C_{3-6}$cycloalkyl; or phenyl optionally substituted by one or two substituents independently selected from the group consisting of: a halogen atom, $C_{1-2}$alkyl, $C_1$fluoroalkyl, $C_{1-2}$alkoxy and $C_1$fluoroalkoxy;

$R^{15a}$, independent of any other $R^{15a}$, is hydrogen or $C_{1-4}$alkyl;

$R^{16}$, independent of any other $R^{16}$, is: $C_{1-4}$alkyl; $C_{3-6}$cycloalkyl; $C_{3-6}$cycloalkyl-CH$_2$—; or phenyl or benzyl, wherein the phenyl and benzyl are independently optionally substituted by one or two substituents independently selected from the group consisting of fluoro, chloro, methyl, $C_1$fluoroalkyl, methoxy and $C_1$fluoroalkoxy;

$R^{16a}$, independent of any other $R^{16a}$, is: $C_{1-6}$alkyl; $C_{3-6}$cycloalkyl optionally substituted by one oxo, OH or $C_{1-2}$alkyl substituent; $C_{3-6}$cycloalkyl-CH$_2$—; pyridinyl optionally substituted on a ring carbon atom by one of: a halogen atom, $C_{1-2}$alkyl, $C_1$fluoroalkyl, $C_{1-2}$alkoxy or $C_1$fluoroalkoxy; Ar$^{5c}$; phenyl optionally substituted by one or two substituents independently selected from the group consisting of: a halogen atom, $C_{1-2}$alkyl, $C_1$fluoroalkyl, $C_{1-2}$alkoxy and $C_1$fluoroalkoxy; benzyl optionally substituted on its ring by one or two substituents independently selected from the group consisting of: a halogen atom, $C_{1-2}$alkyl, $C_1$fluoroalkyl, $C_{1-2}$alkoxy, $C_1$fluoroalkoxy; or a 4-, 5-, 6- or 7-membered saturated heterocyclic ring connected at a ring-carbon and containing one or two ring-hetero-atoms independently selected from the group consisting of O, S, and N; wherein any ring-nitrogens which are present are present as N$R^{27}$ where $R^{27}$ is H, $C_{1-2}$alkyl or —C(O)Me; and wherein the ring is optionally substituted at carbon by one $C_{1-2}$alkyl or oxo substituent, provided that any oxo substituent is substituted at a ring-carbon atom bonded to a ring-nitrogen;

$R^{17}$, independent of any other $R^{17}$, is hydrogen; $C_{1-4}$alkyl; $C_{1-2}$fluoroalkyl; $C_{3-6}$cycloalkyl; —(CH$_2$)$_p^6$—C(O)$R^{16}$ wherein $p^6$ is 0, 1, 2 or 3; —(CH$_2$)$_p^6$—C(O)N$R^{12}R^{13}$; —(CH$_2$)$_p^6$—C(O)O$R^{16}$; —(CH$_2$)$_p^6$—C(O)OH; —SO$_2R^{16}$; —C(O)—CH$_2$—N$R^{12}R^{13}$; —C(O)—CH$_2$—N$R^{15a}$—C(O)—$C_{1-3}$ alkyl; —C(O)—CH$_2$—O—$C_{1-3}$alkyl; or phenyl or benzyl wherein the phenyl or benzyl is optionally substituted on their ring by one or two substituents independently selected from the group consisting of: a halogen atom, $C_{1-2}$alkyl, $C_1$fluoroalkyl, $C_{1-2}$alkoxy and $C_1$fluoroalkoxy;

$R^{30}$, independent of any other $R^{30}$, is hydrogen, $C_{1-4}$alkyl or $C_{3-6}$cycloalkyl;

$Ar^{5b}$ and $Ar^{5c}$ independently are a 5-membered aromatic heterocyclic ring containing one O, S or $NR^{15a}$, the ring can optionally additionally contain one or two N atoms, and wherein the heterocyclic ring is optionally substituted on a ring carbon atom by a substituent selected from the group consisting of: halo, $C_{1-2}$alkyl, $C_1$fluoroalkyl, —$CH_2OH$, —$CH_2$—$OC_{1-2}$alkyl, OH, and —$CH_2$—$NR^{28}R^{29}$ wherein $R^{28}$ and $R^{29}$ independently are H or methyl; and $Het^1$, independent of any other $Het^1$, is a 4-, 5-, 6- or 7-membered saturated heterocyclic ring connected at a ring-carbon and containing one or two ring-hetero-atoms independently selected from the group consisting of O, S, and N; wherein any ring-nitrogens which are present are present as $NR^{31}$ where $R^{31}$ is H, $C_{1-2}$alkyl or —C(O)Me; and wherein the ring is optionally substituted at carbon by one $C_{1-2}$alkyl or oxo substituent, provided that any oxo substituent is substituted at a ring-carbon atom bonded to a ring-nitrogen.

2. A compound or salt as claimed in claim 1, wherein $R^1$ is ethyl or $C_2$fluoroalkyl.

3. A compound or salt as claimed in claim 1, wherein $R^1$ is ethyl.

4. A compound or salt as claimed in claim 1 wherein $R^2$ is hydrogen or methyl.

5. A compound or salt as claimed in claim 1 wherein $R^{3a}$ is methyl, $R^{3b}$ is hydrogen or methyl, and $R^{3e}$ is hydrogen.

6. A compound or salt as claimed in claim 1 wherein $R^{3b}$ is methyl or ethyl, $R^{3c}$ and $R^{3d}$ independently are-hydrogen or methyl, and $R^{3e}$ is-hydrogen.

7. A compound or salt as claimed in claim 6, wherein $R^3$ is t-butyl.

8. A compound or salt as claimed in claim 1 wherein $R^{3c}$ and $R^{3d}$ are independently methyl or ethyl, $R^{3a}$ is methyl, and $R^{3b}$ is hydrogen or methyl.

9. A compound or salt as claimed in claim 8, wherein $R^3$ is 1,2-dimethyl-propyl.

10. A compound or salt as claimed in claim 1 wherein $R^{3c}$ and $R^{3d}$ are independently methyl or ethyl, $R^{3b}$ is hydrogen and $NHR^3$ has the sub-formula (nhr3a):

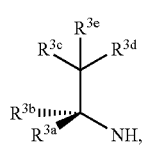

(nhr3a)

wherein sub-formula (nhr3a) means that more than 50% of the compound or salt present has the stereochemistry shown at the carbon atom bearing the $R^{3a}$ and $R^{3b}$ groups.

11. A compound or salt as claimed in claim 10 wherein $NHR^3$ has the sub-formula:

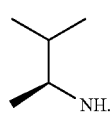

12. A compound or salt as claimed in claim 1 wherein $R^5$ is $C_{3-8}$alkyl; $C_{5-6}$cycloalkyl; ($C_{5-6}$cycloalkyl)methyl-; —$(CH_2)_{n^5}$—$R^{11}$ wherein $n^5$ is 2 or 3 or $R^{11}$ is —$NR^{15}$—$SO_2R^{16}$; or $R^5$ has the sub-formula (x), (xa), (y), (y1), (z) or (za).

13. A compound or salt as claimed in claim 12 wherein $R^5$ has the sub-formula (x), (xa), (y), (y1), (z) or (za).

14. A compound or salt as claimed in claim 13 wherein $R^5$ has the sub-formula (x), (xa), (y), or (z).

15. A compound or salt as claimed in claim 14 wherein $R^5$ has the sub-formula (x) or (xa).

16. A compound or salt as claimed in claim 1 wherein n=1, m=1 and r=1.

17. A compound or salt as claimed in claim 15 wherein:

$R^5$ is sub-formula (x) which is —$(CH_2)_n$—$Ar^X$, or sub-formula (xa) which is —$(CR^{4a}R^{5a})$—$Ar^X$, and $Ar^X$ is sub-formula (x1), (x2), (x3), (x4), (x5), (x6), (x7), (x8), (x9), (x10), (x11), (x12), (x13), (x14), (x15) or (x16):

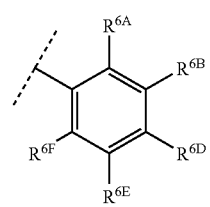
(x1)

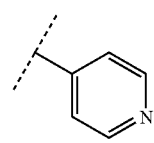
(x2)

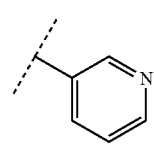
(x3)

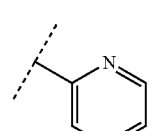
(x4)

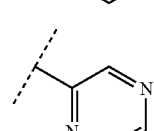
(x5)

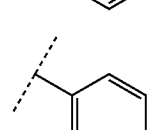
(x6)

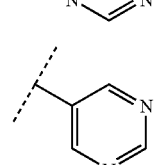
(x7)

-continued

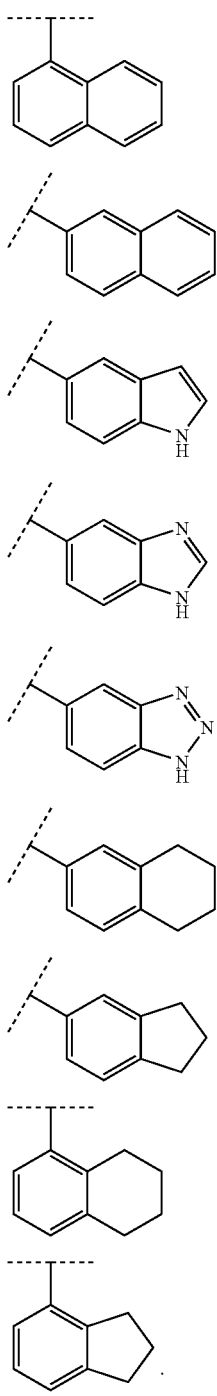

18. A compound or salt as claimed in claim 17 wherein $Ar^X$ has the sub-formula (x1).

19. A compound or salt as claimed in claim 1 wherein, in sub-formula (x) and in sub-formula (xa), $R^{6A}$, $R^{6B}$, $R^{6D}$, $R^{6E}$ and $R^{6F}$, independently of each other, are hydrogen, fluoro, chloro, bromo, iodo, methyl, ethyl, n-propyl, isopropyl, isobutyl, trifluoromethyl, —CH$_2$OH, methoxy, ethoxy, n-propoxy, isopropoxy, C$_1$fluoroalkoxy, nitro (—NO$_2$), OH, C$_{1-3}$alkylS(O)$_2$—, C$_{1-2}$alkylS(O)$_2$—NH—, —CONH$_2$, cyano (—CN), or C$_{1-2}$alkylS(O)$_2$—CH$_2$—.

20. A compound or salt as claimed in claim 19 wherein $R^{6A}$, $R^{6B}$, $R^{6D}$, $R^{6E}$ and $R^{6F}$, independently of each other, are: hydrogen, fluoro, chloro, bromo, methyl, ethyl, n-propyl, isopropyl, trifluoromethyl, —CH$_2$OH, methoxy, ethoxy, n-propoxy, difluoromethoxy, nitro (—NO$_2$), OH, MeS(O)$_2$—, Me-S(O)$_2$—NH— or Me-S(O)$_2$—CH$_2$—.

21. A compound or salt as claimed in claim 1 wherein $R^5$ is: benzyl, (monoalkyl-phenyl)methyl, [mono(fluoroalkyl)-phenyl]methyl, (monohalo-phenyl)methyl, (monoalkoxy-phenyl)methyl, [mono(fluoroalkoxy)-phenyl]methyl, [mono(N,N-dimethylamino)-phenyl]methyl, [mono(methyl-SO$_2$—NH-)-phenyl]methyl, [mono(methyl-SO$_2$-)-phenyl]methyl, (dialkyl-phenyl)methyl, (monoalkyl-monohalo-phenyl)methyl, [mono(fluoroalkyl)-monohalo-phenyl]methyl, (dihalo-phenyl)methyl, (dihalo-monoalkyl-phenyl)methyl, [dihalo-mono(hydroxymethyl)-phenyl]methyl, or (dialkoxy-phenyl)methyl.

22. A compound or salt as claimed in claim 21 wherein $R^5$ is:
(monoC$_{1-4}$alkyl-phenyl)methyl;
(monoC$_1$fluoroalkyl-phenyl)methyl;
(monoC$_{1-3}$alkoxy-phenyl)methyl;
[mono(C$_1$fluoroalkoxy)-phenyl]methyl;
(diC$_{1-2}$alkyl-phenyl)methyl;
(monoC$_{1-4}$alkyl-monohalo-phenyl)methyl;
(dihalo-phenyl)methyl;
(dihalo-monoC$_{1-2}$alkyl-phenyl)methyl; or
[dihalo-mono(hydroxymethyl)-phenyl]methyl.

23. A compound or salt as claimed in claim 1 which is:
N-benzyl-4-{[(1R)-1,2-dimethylpropyl]amino}-1-ethyl-1H-pyrazolo[3,4-b]pyridine-5-carboxamide,
4-{[(1R)-1,2-dimethylpropyl]amino}-1-ethyl-N-(4-fluorophenyl)-1H-pyrazolo[3,4-b]pyridine-5-carboxamide,
4-{[(1R)-1,2-dimethylpropyl]amino}-1-ethyl-N-[4-(trifluoromethyl)benzyl]-1H-pyrazolo[3,4-b]pyridine-5-carboxamide,
N-(2,3-dihydro-1H-inden-2-yl)-4-{[(1R)-1,2-dimethylpropyl]amino}-1-ethyl-1H-pyrazolo[3,4-b]pyridine-5-carboxamide,
4-{[(1R)-1,2-dimethylpropyl]amino}-1-ethyl-N-[4-(methylsulfonyl)benzyl]-1H-pyrazolo[3,4-b]pyridine-5-carboxamide,
N-[4-(difluoromethoxy)benzyl]-4-{[(1S)-1,2-dimethylpropyl]amino}-1-ethyl-1H-pyrazolo[3,4-b]pyridine-5-carboxamide,
4-{[(1S)-1,2-dimethylpropyl]amino}-1-ethyl-N-[(2-methyl-1,3-thiazol-4-yl)methyl]-1H-pyrazolo[3,4-b]pyridine-5-carboxamide,
N-[(5-chloropyridin-2-yl)methyl]-4-{[(1S)-1,2-dimethylpropyl]amino}-1-ethyl-1H-pyrazolo[3,4-b]pyridine-5-carboxamide,
N-(2-chloro-6-fluorobenzyl)-4-{[(1S)-1,2-dimethylpropyl]amino}-1-ethyl-1H-pyrazolo[3,4-b]pyridine-5-carboxamide,
4-{[(1S)-1,2-dimethylpropyl]amino}-1-ethyl-N-{1-[4-(methylsulfonyl)phenyl]ethyl}-1H-pyrazolo[3,4-b]pyridine-5-carboxamide,
4-{[(1S)-1,2-dimethylpropyl]amino}-1-ethyl-N-[(6-methoxypyridin-3-yl)methyl]-1H-pyrazolo[3,4-b]pyridine-5-carboxamide,
4-{[(1S)-1,2-dimethylpropyl]amino}-1-ethyl-N-{3-[(methylamino)carbonyl]benzyl}-1H-pyrazolo[3,4-b]pyridine-5-carboxamide,
4-{[(1S)-1,2-dimethylpropyl]amino}-1-ethyl-N-[(1R)-1-phenylpropyl]-1H-pyrazolo[3,4-b]pyridine-5-carboxamide, 4-{[(1S)-1,2-dimethylpropyl]amino}-N-(2,2-diphenylethyl)-1-ethyl-1H-pyrazolo[3,4-b]pyridine-5-carboxamide, N-[2-(dimethylamino)benzyl]-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-(4-fluorobenzyl)-1H-pyrazolo[3,4-b]pyridine-5-carboxamide, 4-{[(1S)-1,2-dimethylpropyl]amino}-N-(diphenylmethyl)-1-ethyl-1H-pyrazolo[3,4-b]pyridine-5-carboxamide, 4-{[(1S)-1,2-dimethylpropyl]amino}-1-ethyl-N-{4-[(methylamino)carbonyl]benzyl}-1H-pyrazolo[3,4-b]pyridine-5-carboxamide, methyl 4-({[(4-{[(1S)-1,2-dimethylpropyl]amino}-1-ethyl-1H-pyrazolo[3,4-b]pyridin-5-yl)carbonyl]amino}methyl)benzoate, 4-{[(1S)-1,2-dimethylpropyl]amino}-1-ethyl-N-(4-methoxyphenyl)-1H-pyrazolo[3,4-b]pyridine-5-carboxamide, 4-{[(1S)-1,2-dimethylpropyl]amino}-1-ethyl-N-(4-hydroxybenzyl)-1H-pyrazolo[3,4-b]pyridine-5-carboxamide, 4-{[(1S)-1,2-dimethylpropyl]amino}-1-ethyl-N-[3-(trifluoromethyl)benzyl]-1H-pyrazolo[3,4-b]pyridine-5-carboxamide, 4-{[(1S)-1,2-dimethylpropyl]amino}-1-ethyl-N-(4-methoxybenzyl)-1H-pyrazolo[3,4-b]pyridine-5-carboxamide, N-(3,4-difluorobenzyl)-4-{[(1S)-1,2-dimethylpropyl]amino}-1-ethyl-1H-pyrazolo[3,4-b]pyridine-5-carboxamide, N-(2,6-difluorobenzyl)-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-[(1R)-1-phenylethyl]-1H-pyrazolo[3,4-b]pyridine-5-carboxamide, N-(2,5-difluorobenzyl)-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-(3-fluorobenzyl)-1H-pyrazolo[3,4-b]pyridine-5-carboxamide, 4-{[(1S)-1,2-dimethylpropyl]amino}-1-ethyl-N-[2-(trifluoromethyl)benzyl]-1H-pyrazolo[3,4-b]pyridine-5-carboxamide, N-(5-chloro-2,3-dihydro-1H-inden-2-yl)-4-{[(1S)-1,2-dimethylpropyl]amino}-1-ethyl-1H-pyrazolo[3,4-b]pyridine-5-carboxamide, methyl 3-({[(4-{[(1S)-1,2-dimethylpropyl]amino}-1-ethyl-1H-pyrazolo[3,4-b]pyridin-5-yl)carbonyl]amino}methyl)benzoate, N-[2-(aminocarbonyl)benzyl]-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-{4-[(methylsulfonyl)amino]benzyl}-1H-pyrazolo[3,4-b]pyridine-5-carboxamide, 4-{[(1S)-1,2-dimethylpropyl]amino}-1-ethyl-N-{3-[(methylsulfonyl)amino]benzyl}-1H-pyrazolo[3,4-b]pyridine-5-carboxamide, 4-{[(1S)-1,2-dimethylpropyl]amino}-1-ethyl-N-[4-(trifluoromethyl)benzyl]-1H-pyrazolo[3,4-b]pyridine-5-carboxamide, N-(2,3-dihydro-1H-inden-2-yl)-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-[4-(methylsulfonyl)benzyl]-1H-pyrazolo[3,4-b]pyridine-5-carboxamide, N-benzyl-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-(4-fluorophenyl)-1H-pyrazolo[3,4-b]pyridine-5-carboxamide, N-[2-(aminosulfonyl)ethyl]-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-[(6-oxo-1,6-dihydropyridin-3-yl)methyl]-1H-pyrazolo[3,4-b]pyridine-5-carboxamide, 4-{[(1S)-1,2-dimethylpropyl]amino}-1-ethyl-N-{2-[(methylsulfonyl)amino]ethyl}-1H-pyrazolo[3,4-b]pyridine-5-carboxamide, 4-{[(1S)-1,2-dimethylpropyl]amino}-1-ethyl-N-(tetrahydro-2H-pyran-4-yl)-1H-pyrazolo[3,4-b]pyridine-5-carboxamide, 4-{[(1S)-1,2-dimethylpropyl]amino}-1-ethyl-N-[(1-methyl-1H-pyrazol-4-yl)methyl]-1H-pyrazolo[3,4-b]pyridine-5-carboxamide, 4-{[(1S)-1,2-dimethylpropyl]amino}-1-ethyl-N-[3-(methylsulfonyl)benzyl]-1H-pyrazolo[3,4-b]pyridine-5-carboxamide, 4-{[(1S)-1,2-dimethylpropyl]amino}-1-ethyl-N-(pyridin-3-ylmethyl)-1H-pyrazolo[3,4-b]pyridine-5-carboxamide, N-[3-(aminocarbonyl)benzyl]-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-(tetrahydrofuran-2-ylmethyl)-1H-pyrazolo[3,4-b]pyridine-5-carboxamide, N-{4-[(dimethylamino)sulfonyl]benzyl}-4-{[(1S)-1,2-dimethylpropyl]amino}-1-ethyl-1H-pyrazolo[3,4-b]pyridine-5-carboxamide, 4-{[(1S)-1,2-dimethylpropyl]amino}-1-ethyl-N-(2-ethylbutyl)-1H-pyrazolo[3,4-b]pyridine-5-carboxamide, 4-(tert-butylamino)-1-ethyl-N-benzyl-1H-pyrazolo[3,4-b]pyridine-5-carboxamide, 4-(tert-butylamino)-1-ethyl-N-(4-fluorophenyl)-1H-pyrazolo[3,4-b]pyridine-5-carboxamide, 4-(tert-butylamino)-1-ethyl-N-[4-(trifluoromethyl)benzyl]-1H-pyrazolo[3,4-b]pyridine-5-carboxamide, 4-(tert-butylamino)-N-(2,3-dihydro-1H-inden-2-yl)-1-ethyl-1H-pyrazolo[3,4-b]pyridine-5-carboxamide, or 4-(tert-butylamino)-1-ethyl-N-[4-(methylsulfonyl)benzyl]-1H-pyrazolo[3,4-b]pyridine-5-carboxamide.

24. A pharmaceutical composition comprising a compound of formula (I) or a pharmaceutically acceptable salt thereof as defined in claim 1 and one or more pharmaceutically acceptable carriers and/or excipients.

* * * * *